United States Patent
McLaren et al.

(10) Patent No.: US 11,878,119 B2
(45) Date of Patent: Jan. 23, 2024

(54) HEADGEAR WITH LOCK DISENGAGEMENT MECHANISM

(71) Applicant: Fisher & Paykel Healthcare Limited, Auckland (NZ)

(72) Inventors: Mark Arvind McLaren, Auckland (NZ); Brett John Huddart, Auckland (NZ); Jeroen Hammer, Auckland (NZ); Matthew Robert Geoff Slight, Auckland (NZ); Vitaly Kapelevich, Auckland (NZ); David Monroy Felix, Auckland (NZ); Mark Richard Tomlinson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 424 days.

(21) Appl. No.: 16/980,815

(22) PCT Filed: Mar. 14, 2019

(86) PCT No.: PCT/IB2019/052057
§ 371 (c)(1),
(2) Date: Sep. 14, 2020

(87) PCT Pub. No.: WO2019/175814
PCT Pub. Date: Sep. 19, 2019

(65) Prior Publication Data
US 2021/0008316 A1    Jan. 14, 2021

Related U.S. Application Data

(60) Provisional application No. 62/644,002, filed on Mar. 16, 2018.

(51) Int. Cl.
*A61M 16/06*    (2006.01)
*A61M 16/08*    (2006.01)

(52) U.S. Cl.
CPC .... *A61M 16/0622* (2014.02); *A61M 16/0694* (2014.02); *A61M 16/0816* (2013.01)

(58) Field of Classification Search
CPC .. A61M 2202/0208; A61M 2210/0625; A61M 2210/0618; A61M 16/0622; A61M 16/0694
See application file for complete search history.

(56) References Cited

U.S. PATENT DOCUMENTS 301,111 A    7/1884   Genese
472,238 A    4/1892   Van Orden
(Continued)

FOREIGN PATENT DOCUMENTS

CA     996301     9/1976
CA    1311662    12/1992
(Continued)

OTHER PUBLICATIONS cpap.com, InnoMed/Resp Care Bravo Nasal Pillow CPAP Mask with Headgear, (http://web.archive.org/web/*/https://www.cpap.com/productpage/bravo-nasal-interface/), downloaded Feb. 24, 2020, 5 pp.
(Continued)

*Primary Examiner* — Samchuan C Yao
*Assistant Examiner* — Tina Zhang
(74) *Attorney, Agent, or Firm* — Knobbe, Martens, Olson & Bear, LLP

(57) ABSTRACT

A respiratory mask system is provided comprising a respiratory mask and a head engaging portion, wherein the head engaging portion is configured to couple to the respiratory mask to engage a wearer's head via a disengageable mechanism. The disengageable mechanism may comprise a linking member attached to the head engaging portion, a disengagement member attached to the respiratory mask and
(Continued)

configured to receive the linking member, wherein the disengagement member is configured to be moveable between a first position and a second position, a control configured to allow a wearer of the mask to move the disengagement member towards the first position and one or more surfaces defined by the disengagement member and configured to exert a frictional force on the linking member.

23 Claims, 78 Drawing Sheets

(56) References Cited

U.S. PATENT DOCUMENTS

| | | | |
|---|---|---|---|
| 577,926 A | 3/1897 | Miller | |
| 718,470 A | 1/1903 | Jones | |
| 751,091 A | 2/1904 | Moran | |
| 770,013 A | 9/1904 | Linn | |
| 1,364,104 A | 1/1921 | Geer | |
| 1,635,545 A | 7/1927 | Drager | |
| 1,942,442 A | 1/1934 | Motsinger | |
| 2,199,690 A | 5/1940 | Bullard | |
| 2,296,150 A | 9/1942 | Dockson et al. | |
| 2,353,643 A | 7/1944 | Bulbulian | |
| 2,359,506 A | 10/1944 | Battley et al. | |
| 2,388,604 A | 11/1945 | Eisenbud | |
| 2,390,233 A | 12/1945 | Akerman et al. | |
| 2,508,050 A | 5/1950 | Valente | |
| 2,586,851 A | 2/1952 | Monro et al. | |
| 2,611,897 A | 9/1952 | Adams | |
| 2,661,514 A | 12/1953 | Ada | |
| 2,693,800 A | 11/1954 | Caldwell | |
| 2,738,788 A | 3/1956 | Matheson et al. | |
| 2,843,121 A | 7/1958 | Hudson | |
| 2,859,748 A | 11/1958 | Hudson | |
| 3,045,672 A | 7/1962 | Croasdaile | |
| 3,156,922 A | 11/1964 | Anderson | |
| 3,295,529 A | 1/1967 | Corrigall et al. | |
| 3,416,521 A | 12/1968 | Humphrey | |
| 3,457,564 A | 7/1969 | Holloway | |
| 3,490,452 A | 1/1970 | Greenfield | |
| 3,500,474 A | 3/1970 | Austin | |
| 3,530,031 A | 9/1970 | Loew | |
| 3,792,702 A | 2/1974 | Delest | |
| 3,834,682 A | 9/1974 | McPhee | |
| 3,850,171 A | 11/1974 | Ball et al. | |
| 3,887,968 A | 6/1975 | Lynam | |
| 3,972,321 A | 8/1976 | Proctor | |
| 3,990,757 A | 11/1976 | Gill | |
| 3,992,720 A | 11/1976 | Nicolinas | |
| 3,994,022 A | 11/1976 | Villari et al. | |
| 4,051,556 A | 10/1977 | Davenport et al. | |
| 4,062,068 A | 12/1977 | Davenport et al. | |
| 4,090,510 A | 5/1978 | Segersten | |
| D250,047 S | 10/1978 | Lewis et al. | |
| D250,131 S | 10/1978 | Lewis et al. | |
| 4,127,130 A | 11/1978 | Naysmith | |
| D252,322 S | 7/1979 | Johnson | |
| 4,167,185 A | 9/1979 | Lewis | |
| 4,201,205 A | 5/1980 | Bartholomew | |
| 4,266,540 A | 5/1981 | Panzik et al. | |
| 4,278,082 A | 7/1981 | Blackmer | |
| 4,288,891 A | 9/1981 | Boden | |
| 4,313,437 A | 2/1982 | Martin | |
| 4,328,605 A | 5/1982 | Hutchinson et al. | |
| 4,354,488 A | 10/1982 | Bartos | |
| 4,367,735 A | 1/1983 | Dali | |
| 4,402,316 A | 9/1983 | Gadberry | |
| 4,413,382 A | 11/1983 | Siegmann | |
| 4,437,462 A | 3/1984 | Piljay | |
| 4,453,292 A | 6/1984 | Bakker | |
| 4,458,373 A | 7/1984 | Maslow | |
| 4,477,928 A | 10/1984 | Graff | |
| 4,606,077 A | 8/1986 | Phillips | |
| D293,613 S | 1/1988 | Wingler | |
| 4,734,940 A | 4/1988 | Galet et al. | |
| 4,753,233 A | 6/1988 | Grimes | |
| 4,782,832 A | 11/1988 | Trimble et al. | |
| 4,817,596 A | 4/1989 | Gallet | |
| 4,848,334 A | 7/1989 | Bellm | |
| 4,853,275 A | 8/1989 | Tracy et al. | |
| 4,856,508 A | 8/1989 | Tayebi | |
| 4,915,105 A | 4/1990 | Lee | |
| 4,941,467 A | 7/1990 | Takata | |
| 4,944,310 A | 7/1990 | Sullivan | |
| 4,947,488 A | 8/1990 | Ashnioff | |
| D310,431 S | 9/1990 | Bellm | |
| 4,971,051 A | 11/1990 | Toffolon | |
| 4,986,269 A | 1/1991 | Hakkinen | |
| 5,010,925 A | 4/1991 | Atkinson et al. | |
| 5,016,625 A | 5/1991 | Hsu et al. | |
| 5,042,478 A | 8/1991 | Kopala et al. | |
| D320,677 S | 10/1991 | Kumagai et al. | |
| 5,052,084 A | 10/1991 | Braun | |
| D321,419 S | 11/1991 | Wallace | |
| 5,065,756 A | 11/1991 | Rapoport | |
| 5,074,297 A | 12/1991 | Venegas | |
| 5,094,236 A | 3/1992 | Tayebi | |
| 5,113,857 A | 5/1992 | Dickerman et al. | |
| 5,148,578 A | 9/1992 | Clarke et al. | |
| 5,148,802 A | 9/1992 | Sanders et al. | |
| 5,191,882 A | 3/1993 | Vogliano | |
| 5,231,979 A | 8/1993 | Rose | |
| 5,245,995 A | 9/1993 | Sullivan et al. | |
| D340,317 S | 10/1993 | Cole | |
| 5,269,296 A | 12/1993 | Landis et al. | |
| D354,128 S | 1/1995 | Rinehart | |
| D355,484 S | 2/1995 | Rinehart | |
| 5,388,743 A | 2/1995 | Silagy | |
| 5,438,979 A | 8/1995 | Johnson et al. | |
| 5,477,852 A | 12/1995 | Landis et al. | |
| 5,488,948 A | 2/1996 | Dubruille | |
| 5,513,634 A | 5/1996 | Jackson | |
| 5,529,062 A | 6/1996 | Byrd | |
| 5,533,506 A | 7/1996 | Wood | |
| 5,546,605 A | 8/1996 | Mallardi | |
| 5,551,419 A | 9/1996 | Froehlich et al. | |
| 5,566,395 A | 10/1996 | Nebeker | |
| 5,595,174 A | 1/1997 | Gwaltney | |
| 5,601,078 A | 2/1997 | Schaller et al. | |
| D378,610 S | 3/1997 | Reischel et al. | |
| 5,657,752 A | 8/1997 | Landis et al. | |
| 5,724,965 A | 3/1998 | Handke et al. | |
| 5,752,510 A | 5/1998 | Goldstein | |
| 5,755,578 A | 5/1998 | Contant et al. | |
| 5,774,901 A | 7/1998 | Minami | |
| 5,884,624 A | 3/1999 | Barnett et al. | |
| 5,921,239 A | 7/1999 | McCall et al. | |
| 5,941,245 A * | 8/1999 | Hannah | A62B 18/084 128/207.11 |
| 5,941,856 A | 8/1999 | Kovacs et al. | |
| 6,017,315 A | 1/2000 | Starr et al. | |
| 6,019,101 A | 2/2000 | Cotner et al. | |
| 6,044,844 A | 4/2000 | Kwok et al. | |
| 6,050,260 A | 4/2000 | Daniell et al. | |
| 6,119,694 A | 9/2000 | Correa et al. | |
| 6,192,886 B1 | 2/2001 | Rudolph | |
| D440,302 S | 4/2001 | Wolfe | |
| 6,256,798 B1 | 7/2001 | Egolf et al. | |
| 6,272,690 B1 | 8/2001 | Carey et al. | |
| 6,282,725 B1 | 9/2001 | Vanidestine, Jr. | |
| 6,298,850 B1 | 10/2001 | Argraves | |
| 6,338,342 B1 | 1/2002 | Fecteau et al. | |
| 6,347,631 B1 | 2/2002 | Hansen et al. | |
| D455,891 S | 4/2002 | Biedrzycki | |
| 6,418,928 B1 | 7/2002 | Bordewick et al. | |
| 6,422,238 B1 | 7/2002 | Lithgow | |
| 6,431,172 B1 | 8/2002 | Bordewick | |
| 6,435,181 B1 | 8/2002 | Jones, Jr. et al. | |
| 6,439,234 B1 | 8/2002 | Curti et al. | |
| 6,470,886 B1 | 10/2002 | Jestrabek-Hart | |
| 6,478,026 B1 | 11/2002 | Wood | |
| 6,491,034 B1 | 12/2002 | Gunaratnam et al. | |

(56) References Cited

U.S. PATENT DOCUMENTS

| | | | |
|---|---|---|---|
| 6,536,435 B1* | 3/2003 | Fecteau | A62B 18/084 |
| | | | 128/201.24 |
| 6,561,188 B1 | 5/2003 | Ellis | |
| 6,561,191 B1 | 5/2003 | Kwok | |
| 6,581,594 B1 | 6/2003 | Drew et al. | |
| 6,581,601 B2 | 6/2003 | Ziaee | |
| 6,588,424 B2 | 7/2003 | Bardel | |
| 6,631,718 B1 | 10/2003 | Lovell | |
| 6,637,434 B2 | 10/2003 | Noble | |
| 6,644,315 B2 | 11/2003 | Ziaee | |
| 6,651,658 B1 | 11/2003 | Hill et al. | |
| 6,659,102 B1 | 12/2003 | Sico | |
| 6,662,803 B2 | 12/2003 | Gradon et al. | |
| 6,679,257 B1 | 1/2004 | Robertson et al. | |
| 6,679,265 B2 | 1/2004 | Strickland et al. | |
| 6,772,761 B1 | 8/2004 | Rucker, Jr. | |
| 6,851,425 B2 | 2/2005 | Jaffre et al. | |
| 6,883,519 B2 | 4/2005 | Schmidtke et al. | |
| 6,886,564 B2 | 5/2005 | Sullivan et al. | |
| 6,892,729 B2 | 5/2005 | Smith et al. | |
| 6,907,882 B2 | 6/2005 | Ging et al. | |
| 6,951,218 B2 | 10/2005 | Gradon et al. | |
| 7,004,165 B1 | 2/2006 | Salcido | |
| D520,140 S | 5/2006 | Chaggares | |
| 7,036,508 B2 | 5/2006 | Kwok | |
| 7,062,795 B2 | 6/2006 | Skiba et al. | |
| 7,066,179 B2 | 6/2006 | Eaton et al. | |
| D526,094 S | 8/2006 | Chen | |
| 7,096,864 B1 | 8/2006 | Mayer et al. | |
| 7,096,867 B2 | 8/2006 | Smith et al. | |
| 7,201,169 B2 | 4/2007 | Wilkie et al. | |
| 7,207,333 B2 | 4/2007 | Tohara | |
| 7,210,481 B1 | 5/2007 | Lovell et al. | |
| 7,219,669 B1 | 5/2007 | Lovell et al. | |
| 7,225,811 B2 | 6/2007 | Ruiz et al. | |
| 7,318,437 B2 | 1/2008 | Gunaratnam et al. | |
| 7,353,826 B2 | 4/2008 | Sleeper et al. | |
| 7,353,827 B2 | 4/2008 | Geist | |
| 7,814,911 B2 | 10/2010 | Bordewick et al. | |
| 7,845,352 B2 | 12/2010 | Sleeper et al. | |
| 7,861,715 B2 | 1/2011 | Jones et al. | |
| 7,870,860 B2 | 1/2011 | McCormick et al. | |
| 7,896,003 B2 | 3/2011 | Matula et al. | |
| 7,913,692 B2 | 3/2011 | Kwok | |
| 7,967,014 B2 | 6/2011 | Heidmann | |
| 8,042,539 B2 | 10/2011 | Chandran et al. | |
| 8,047,893 B2 | 11/2011 | Fenske | |
| 8,074,651 B2 | 12/2011 | Bierman et al. | |
| 8,104,473 B2 | 1/2012 | Woodard et al. | |
| 8,132,270 B2 | 3/2012 | Lang et al. | |
| 8,136,524 B2 | 3/2012 | Ging et al. | |
| 8,297,285 B2 | 10/2012 | Henry et al. | |
| 8,371,302 B2 | 2/2013 | Ging et al. | |
| 8,443,807 B2 | 5/2013 | McAuley et al. | |
| D686,313 S | 7/2013 | Matula et al. | |
| 8,479,741 B2 | 7/2013 | McAuley et al. | |
| 8,505,538 B2 | 8/2013 | Amarasinghe | |
| 8,522,785 B2 | 9/2013 | Berthon-Jones et al. | |
| 8,573,201 B2 | 11/2013 | Rummery et al. | |
| 8,596,271 B2 | 12/2013 | Matula, Jr. et al. | |
| 8,596,274 B2 | 12/2013 | Hieber et al. | |
| 8,631,793 B2 | 1/2014 | Omura et al. | |
| 8,636,005 B2 | 1/2014 | Gradon et al. | |
| 8,636,007 B2 | 1/2014 | Rummery et al. | |
| 8,636,008 B2 | 1/2014 | Flory et al. | |
| 8,757,157 B2 | 6/2014 | Price et al. | |
| 8,783,257 B2 | 7/2014 | McAuley et al. | |
| 8,794,239 B2 | 8/2014 | Gunaratnam | |
| 8,857,435 B2 | 10/2014 | Matula, Jr. et al. | |
| 8,915,251 B2 | 12/2014 | Lubke et al. | |
| 8,997,742 B2 | 4/2015 | Moore et al. | |
| 9,032,955 B2 | 5/2015 | Lubke et al. | |
| 9,044,564 B2 | 6/2015 | Dravitzki et al. | |
| 9,138,555 B2 | 9/2015 | McAuley et al. | |
| 9,149,596 B2 | 10/2015 | Valcic et al. | |
| 9,265,909 B2 | 2/2016 | Ho et al. | |
| 9,302,065 B2 | 4/2016 | Smith et al. | |
| 9,320,866 B2 | 4/2016 | McAuley et al. | |
| 9,333,315 B2 | 5/2016 | McAuley et al. | |
| 9,339,622 B2 | 5/2016 | McAuley et al. | |
| 9,480,809 B2 | 11/2016 | Guney et al. | |
| 9,517,320 B2 | 12/2016 | Barlow et al. | |
| 9,550,038 B2 | 1/2017 | McAuley et al. | |
| 9,592,336 B2 | 3/2017 | Nielsen et al. | |
| 9,656,038 B2* | 5/2017 | Rummery | A61M 16/0633 |
| 9,744,385 B2 | 8/2017 | Henry | |
| 9,782,554 B2 | 10/2017 | Mazzone et al. | |
| 9,878,118 B2 | 1/2018 | Formica | |
| D810,277 S | 2/2018 | Amarasinghe | |
| 9,884,160 B2 | 2/2018 | McAuley | |
| 9,901,700 B2 | 2/2018 | McAuley et al. | |
| 9,925,349 B2 | 3/2018 | Jablonski | |
| 9,974,914 B2 | 5/2018 | McAuley | |
| 9,993,606 B2 | 6/2018 | Gibson et al. | |
| 10,039,665 B2 | 8/2018 | Blaszczykiewicz et al. | |
| 10,065,010 B2 | 9/2018 | Smith et al. | |
| 10,071,217 B2 | 9/2018 | Grashow | |
| 10,080,856 B2 | 9/2018 | McLaren | |
| 10,207,072 B2 | 2/2019 | Dunn et al. | |
| 10,279,138 B2 | 5/2019 | Ovzinsky | |
| 10,456,546 B2 | 10/2019 | McLaren et al. | |
| 10,646,680 B2 | 5/2020 | Huddart et al. | |
| 10,675,428 B2 | 6/2020 | Guney et al. | |
| 10,792,451 B2 | 10/2020 | Allan et al. | |
| 10,828,449 B2 | 11/2020 | Higgins et al. | |
| 10,828,452 B2 | 11/2020 | Huddart et al. | |
| 10,874,814 B2 | 12/2020 | Huddart et al. | |
| 2002/0005198 A1 | 1/2002 | Kwok et al. | |
| 2002/0020416 A1 | 2/2002 | Namey | |
| 2002/0046755 A1 | 4/2002 | Voss | |
| 2002/0052568 A1 | 5/2002 | Houser et al. | |
| 2002/0053347 A1 | 5/2002 | Ziaee | |
| 2002/0059935 A1 | 5/2002 | Wood | |
| 2002/0096178 A1 | 7/2002 | Ziaee | |
| 2002/0157668 A1 | 10/2002 | Bardel | |
| 2003/0005933 A1 | 1/2003 | Izuchukwu | |
| 2003/0051732 A1 | 3/2003 | Smith et al. | |
| 2003/0079749 A1 | 5/2003 | Strickland et al. | |
| 2003/0084903 A1 | 5/2003 | Fecteau et al. | |
| 2003/0111080 A1 | 6/2003 | Olsen et al. | |
| 2003/0121519 A1 | 7/2003 | Estes et al. | |
| 2003/0164170 A1 | 9/2003 | Drew et al. | |
| 2003/0172936 A1 | 9/2003 | Wilkie et al. | |
| 2003/0196656 A1 | 10/2003 | Moore | |
| 2003/0196659 A1 | 10/2003 | Gradon et al. | |
| 2003/0196664 A1 | 10/2003 | Jacobson | |
| 2003/0200970 A1 | 10/2003 | Stenzler et al. | |
| 2004/0067333 A1 | 4/2004 | Amarasinghe | |
| 2004/0211427 A1 | 10/2004 | Jones et al. | |
| 2004/0226566 A1 | 11/2004 | Gunaratnam et al. | |
| 2005/0011524 A1 | 1/2005 | Thomlinson et al. | |
| 2005/0016067 A1 | 1/2005 | Pettit | |
| 2005/0028822 A1 | 2/2005 | Sleeper et al. | |
| 2005/0033247 A1 | 2/2005 | Thompson | |
| 2005/0066976 A1 | 3/2005 | Wondka | |
| 2005/0076913 A1 | 4/2005 | Ho et al. | |
| 2005/0098183 A1 | 5/2005 | Nash et al. | |
| 2005/0150497 A1 | 7/2005 | Eifler et al. | |
| 2005/0161049 A1 | 7/2005 | Wright | |
| 2005/0199239 A1 | 9/2005 | Lang et al. | |
| 2005/0199242 A1 | 9/2005 | Matula et al. | |
| 2005/0205096 A1 | 9/2005 | Matula | |
| 2005/0235999 A1 | 10/2005 | Wood et al. | |
| 2006/0060200 A1 | 3/2006 | Ho et al. | |
| 2006/0081250 A1 | 4/2006 | Bordewick et al. | |
| 2006/0096596 A1 | 5/2006 | Occhialini et al. | |
| 2006/0107958 A1 | 5/2006 | Sleeper | |
| 2006/0113147 A1 | 6/2006 | Harris | |
| 2006/0118117 A1 | 6/2006 | Berthon-Jones et al. | |
| 2006/0124131 A1 | 6/2006 | Chandran | |
| 2006/0137690 A1 | 6/2006 | Gunaratnam et al. | |
| 2006/0174887 A1 | 8/2006 | Chandran et al. | |
| 2006/0174892 A1 | 8/2006 | Leksutin et al. | |
| 2006/0196510 A1 | 9/2006 | McDonald et al. | |

(56) References Cited

U.S. PATENT DOCUMENTS

| | | |
|---|---|---|
| 2006/0196511 A1 | 9/2006 | Lau et al. |
| 2006/0237018 A1 | 10/2006 | McAuley et al. |
| 2007/0000492 A1 | 1/2007 | Hansel et al. |
| 2007/0010786 A1 | 1/2007 | Casey et al. |
| 2007/0089749 A1 | 4/2007 | Ho et al. |
| 2007/0125385 A1 | 6/2007 | Ho et al. |
| 2007/0125387 A1 | 6/2007 | Zollinger et al. |
| 2007/0130663 A1 | 6/2007 | Lang et al. |
| 2007/0137653 A1 | 6/2007 | Wood |
| 2007/0163600 A1 | 7/2007 | Hoffman |
| 2007/0169777 A1 | 7/2007 | Amarasinghe et al. |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0235033 A1 | 10/2007 | Reier et al. |
| 2007/0295335 A1 | 12/2007 | Nashed |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0052806 A1 | 3/2008 | McDaniel |
| 2008/0053450 A1 | 3/2008 | Van Kerkwyk et al. |
| 2008/0060648 A1 | 3/2008 | Thornton et al. |
| 2008/0060653 A1 | 3/2008 | Hallet et al. |
| 2008/0060657 A1 | 3/2008 | McAuley et al. |
| 2008/0065015 A1 | 3/2008 | Fiser |
| 2008/0083412 A1 | 4/2008 | Henry et al. |
| 2008/0092906 A1 | 4/2008 | Gunaratnam et al. |
| 2008/0099024 A1 | 5/2008 | Gunaratnam et al. |
| 2008/0110464 A1 | 5/2008 | Davidson et al. |
| 2008/0134480 A1 | 6/2008 | Shiue |
| 2008/0196728 A1 | 8/2008 | Ho |
| 2008/0230068 A1 | 9/2008 | Rudolph |
| 2008/0230069 A1* | 9/2008 | Valcic ............... A61M 16/0683 128/207.11 |
| 2008/0264422 A1 | 10/2008 | Fishman |
| 2008/0302366 A1 | 12/2008 | McGinnis et al. |
| 2008/0314388 A1 | 12/2008 | Brambilla et al. |
| 2009/0000624 A1 | 1/2009 | Lee et al. |
| 2009/0014007 A1 | 1/2009 | Brambilla et al. |
| 2009/0032026 A1 | 2/2009 | Price et al. |
| 2009/0044808 A1 | 2/2009 | Guney et al. |
| 2009/0044809 A1 | 2/2009 | Welchel et al. |
| 2009/0120442 A1 | 5/2009 | Ho |
| 2009/0133697 A1 | 5/2009 | Kwok et al. |
| 2009/0145429 A1 | 6/2009 | Ging et al. |
| 2009/0173349 A1 | 7/2009 | Hernandez et al. |
| 2009/0178680 A1 | 7/2009 | Chang |
| 2009/0183739 A1 | 7/2009 | Wondka |
| 2009/0211583 A1 | 8/2009 | Carroll |
| 2009/0250060 A1 | 10/2009 | Hacke et al. |
| 2009/0320187 A1 | 12/2009 | Petzl et al. |
| 2010/0000538 A1 | 1/2010 | Edwards et al. |
| 2010/0000544 A1 | 1/2010 | Blaszczykiewicz et al. |
| 2010/0018534 A1 | 1/2010 | Veliss et al. |
| 2010/0037897 A1 | 2/2010 | Wood |
| 2010/0154798 A1 | 6/2010 | Henry et al. |
| 2010/0224199 A1 | 9/2010 | Smith et al. |
| 2010/0258132 A1 | 10/2010 | Moore |
| 2010/0258136 A1 | 10/2010 | Doherty et al. |
| 2010/0282265 A1 | 11/2010 | Melidis et al. |
| 2010/0307502 A1 | 12/2010 | Rummery et al. |
| 2010/0313532 A1 | 12/2010 | Stjernfelt et al. |
| 2010/0313891 A1 | 12/2010 | Veliss et al. |
| 2010/0319700 A1 | 12/2010 | Ng et al. |
| 2011/0048425 A1* | 3/2011 | Chang ............... A61M 16/0638 128/206.24 |
| 2011/0197341 A1 | 8/2011 | Formica |
| 2011/0220113 A1 | 9/2011 | Newman |
| 2011/0247628 A1 | 10/2011 | Ho |
| 2011/0259335 A1* | 10/2011 | Sullivan ............... A62B 18/084 128/207.18 |
| 2011/0265791 A1 | 11/2011 | Ging et al. |
| 2011/0265796 A1 | 11/2011 | Amarasinghe et al. |
| 2012/0067349 A1 | 3/2012 | Barlow et al. |
| 2012/0125339 A1 | 5/2012 | Ho et al. |
| 2012/0132209 A1 | 5/2012 | Rummery |
| 2012/0138063 A1 | 6/2012 | Eves et al. |
| 2012/0174355 A1 | 7/2012 | Fraze |
| 2012/0222680 A1 | 9/2012 | Eves et al. |
| 2012/0304999 A1 | 12/2012 | Swift et al. |
| 2013/0000648 A1 | 1/2013 | Madaus et al. |
| 2013/0139822 A1 | 6/2013 | Gibson |
| 2013/0152918 A1 | 6/2013 | Rummery et al. |
| 2013/0152937 A1 | 6/2013 | Jablonski |
| 2013/0160769 A1 | 6/2013 | Ng et al. |
| 2013/0220327 A1 | 8/2013 | Barlow et al. |
| 2013/0319421 A1 | 12/2013 | Hitchcock et al. |
| 2014/0026888 A1 | 1/2014 | Matula |
| 2014/0026890 A1 | 1/2014 | Haskard et al. |
| 2014/0083428 A1 | 3/2014 | Rothermel et al. |
| 2014/0102456 A1 | 4/2014 | Ovizinsky |
| 2014/0137870 A1 | 5/2014 | Barlow |
| 2014/0158726 A1 | 6/2014 | Malara |
| 2014/0166019 A1 | 6/2014 | Ho et al. |
| 2014/0190486 A1 | 7/2014 | Dunn et al. |
| 2014/0209098 A1 | 7/2014 | Dunn |
| 2014/0216452 A1 | 8/2014 | Miller et al. |
| 2014/0305439 A1 | 10/2014 | Chodkowski |
| 2014/0358054 A1 | 12/2014 | Capra |
| 2015/0000615 A1 | 1/2015 | Imran et al. |
| 2015/0005685 A1 | 1/2015 | Chetlapalli et al. |
| 2015/0028519 A1 | 1/2015 | Lang et al. |
| 2015/0033457 A1 | 2/2015 | Tryner et al. |
| 2015/0051000 A1 | 2/2015 | Henn |
| 2015/0090268 A1 | 4/2015 | Madaus et al. |
| 2015/0128953 A1 | 5/2015 | Formica et al. |
| 2015/0151070 A1 | 6/2015 | Capra et al. |
| 2015/0190262 A1 | 7/2015 | Capra et al. |
| 2015/0202397 A1 | 7/2015 | Pastoor |
| 2015/0217150 A1 | 8/2015 | Harris |
| 2015/0285337 A1 | 10/2015 | Dingley et al. |
| 2015/0290415 A1 | 10/2015 | Dunn |
| 2016/0022944 A1 | 1/2016 | Chodkowski et al. |
| 2016/0038707 A1 | 2/2016 | Allan et al. |
| 2016/0045700 A1 | 2/2016 | Amarasinghe |
| 2016/0082214 A1 | 3/2016 | Barlow et al. |
| 2016/0144146 A1* | 5/2016 | Huddart ............ A61M 16/0816 128/206.21 |
| 2016/0166793 A1 | 6/2016 | McLaren et al. |
| 2016/0178027 A1 | 6/2016 | Wetzel |
| 2016/0278463 A1 | 9/2016 | Stevenson |
| 2016/0375214 A1 | 12/2016 | Chodkowski et al. |
| 2017/0136269 A1 | 5/2017 | Jacotey et al. |
| 2017/0182276 A1 | 6/2017 | Hammer |
| 2017/0189636 A1 | 7/2017 | Gibson et al. |
| 2017/0216548 A1 | 8/2017 | Gerhardt |
| 2018/0214655 A1 | 8/2018 | Kooij et al. |
| 2018/0264218 A1 | 9/2018 | Chodkowski |
| 2018/0339123 A1 | 11/2018 | Smith et al. |
| 2019/0083734 A1 | 3/2019 | Hammer et al. |
| 2019/0111227 A1 | 4/2019 | Veliss et al. |
| 2019/0117026 A1 | 4/2019 | Felix et al. |
| 2019/0151592 A1* | 5/2019 | Bornholdt ......... A61M 16/0666 |
| 2020/0129720 A1 | 4/2020 | McLaren et al. |
| 2020/0171260 A1 | 6/2020 | McLaren et al. |
| 2020/0230343 A1 | 7/2020 | Sims et al. |
| 2020/0230344 A1 | 7/2020 | Huddart et al. |
| 2020/0338294 A1 | 10/2020 | McLaren et al. |
| 2021/0016041 A1 | 1/2021 | Huddart et al. |
| 2022/0126049 A1* | 4/2022 | Amarasinghe .... A61M 16/0875 |
| 2022/0331542 A1 | 10/2022 | McLaren et al. |

FOREIGN PATENT DOCUMENTS

| | | |
|---|---|---|
| CN | 2172538 | 7/1994 |
| CN | 1784250 | 6/2006 |
| CN | 1901963 A | 1/2007 |
| CN | 201033204 | 3/2008 |
| CN | 201171846 | 12/2008 |
| CN | 101432039 A | 5/2009 |
| CN | 100502972 C | 6/2009 |
| CN | 101516427 | 8/2009 |
| CN | 202822396 U | 3/2013 |
| DE | 895692 | 11/1953 |

(56) References Cited

FOREIGN PATENT DOCUMENTS

| | | |
|---|---|---|
| DE | 2706284 | 8/1978 |
| DE | 3122034 | 12/1982 |
| DE | 3907428 | 9/1990 |
| DE | 10254399 | 6/2004 |
| DE | 102006011151 | 9/2007 |
| EP | 0 350 322 | 1/1990 |
| EP | 0 401 307 | 8/1995 |
| EP | 0 879 565 | 11/1998 |
| EP | 0 982 049 | 3/2000 |
| EP | 1 187 650 | 12/2005 |
| EP | 2 130 563 | 12/2009 |
| EP | 2 327 443 | 6/2011 |
| EP | 2 517 757 | 10/2012 |
| EP | 2 022 528 | 3/2016 |
| EP | 2866870 B8 | 12/2021 |
| EP | 3967353 A1 | 6/2022 |
| FR | 2390116 | 3/1938 |
| FR | 2618340 | 11/1970 |
| FR | 825960 | 1/1989 |
| FR | 2658725 | 8/1991 |
| FR | 2749176 | 12/1997 |
| FR | 2804421 | 8/2001 |
| GB | 190224431 | 12/1902 |
| GB | 339522 | 12/1930 |
| GB | 826198 | 12/1959 |
| GB | 880824 | 10/1961 |
| GB | 1467828 | 3/1977 |
| GB | 2133275 | 7/1984 |
| GB | 2188236 | 9/1987 |
| GB | 1211268 | 4/2000 |
| GB | 2478305 | 9/2011 |
| GB | 2491227 | 11/2012 |
| GB | 2553475 | 3/2018 |
| JP | S46-12114 | 4/1971 |
| JP | 46-016719 | 6/1971 |
| JP | S55-89072 | 7/1980 |
| JP | 2004-016488 | 1/2004 |
| JP | 2003-053874 | 9/2004 |
| JP | 2009-125306 | 6/2009 |
| JP | 2010-090973 | 4/2010 |
| JP | 2000-102624 | 5/2013 |
| JP | 2018-127729 | 8/2018 |
| KR | 10-2011-0028950 | 3/2011 |
| NZ | 585295 | 12/2011 |
| TW | WO 08/148086 | 12/2008 |
| WO | WO 95/12432 | 5/1995 |
| WO | WO 97/32494 | 9/1997 |
| WO | WO 98/003225 | 1/1998 |
| WO | WO 98/018514 | 5/1998 |
| WO | WO 99/04842 | 2/1999 |
| WO | WO 99/058181 | 11/1999 |
| WO | WO 00/50122 | 8/2000 |
| WO | WO 00/069497 | 11/2000 |
| WO | WO 00/074758 | 12/2000 |
| WO | WO 01/041854 | 6/2001 |
| WO | WO 01/097892 | 12/2001 |
| WO | WO 02/44749 | 6/2002 |
| WO | WO 02/047749 | 6/2002 |
| WO | WO 02/074372 | 9/2002 |
| WO | WO 04/041341 | 5/2004 |
| WO | WO 04/073778 | 9/2004 |
| WO | WO 05/021075 | 3/2005 |
| WO | WO 05/032634 | 4/2005 |
| WO | WO 05/046776 | 5/2005 |
| WO | WO 05/051468 | 6/2005 |
| WO | WO 05/063328 | 7/2005 |
| WO | WO 05/118042 | 12/2005 |
| WO | WO 05/123166 | 12/2005 |
| WO | WO 06/130903 | 12/2006 |
| WO | WO 06/138416 | 12/2006 |
| WO | WO 07/022562 | 3/2007 |
| WO | WO 07/041786 | 4/2007 |
| WO | WO 07/068044 | 6/2007 |
| WO | WO 07/125487 | 11/2007 |
| WO | WO 07/147088 | 12/2007 |
| WO | WO 08/007985 | 1/2008 |
| WO | WO 08/060295 | 5/2008 |
| WO | WO 08/070929 | 6/2008 |
| WO | WO 08/106716 | 9/2008 |
| WO | WO 09/026627 | 3/2009 |
| WO | WO 09/038918 | 3/2009 |
| WO | WO 09/052560 | 4/2009 |
| WO | WO 09/059353 | 5/2009 |
| WO | WO 09/092057 | 7/2009 |
| WO | WO 09/108994 | 9/2009 |
| WO | WO 09/108995 | 9/2009 |
| WO | WO 09/139647 | 11/2009 |
| WO | WO 09/148956 | 12/2009 |
| WO | WO 10/066004 | 6/2010 |
| WO | WO 10/131189 | 11/2010 |
| WO | WO 10/139014 | 12/2010 |
| WO | WO 11/072739 | 6/2011 |
| WO | WO 11/077254 | 6/2011 |
| WO | WO 11/112401 | 9/2011 |
| WO | WO 12/07300 | 1/2012 |
| WO | WO 12/045127 | 4/2012 |
| WO | WO 12/069951 | 5/2012 |
| WO | WO 12/071300 | 5/2012 |
| WO | WO 12/143822 | 10/2012 |
| WO | WO 12/177152 | 12/2012 |
| WO | WO 13/006913 | 1/2013 |
| WO | WO 13/026091 | 2/2013 |
| WO | WO 13/026092 | 2/2013 |
| WO | WO 13/064930 | 5/2013 |
| WO | WO 14/020469 | 2/2014 |
| WO | WO 14/025267 | 2/2014 |
| WO | WO 14/031673 | 2/2014 |
| WO | WO 14/077708 | 5/2014 |
| WO | WO 2014/075141 | 5/2014 |
| WO | WO 14/110622 | 7/2014 |
| WO | WO 14/110626 | 7/2014 |
| WO | WO 14/129913 | 8/2014 |
| WO | WO 14/175753 | 10/2014 |
| WO | WO 2014/175752 | 10/2014 |
| WO | WO 15/033287 | 3/2015 |
| WO | WO 15/043229 | 4/2015 |
| WO | WO 15/070289 | 5/2015 |
| WO | WO 15/079396 | 6/2015 |
| WO | WO 15/083060 | 6/2015 |
| WO | WO 15/151019 | 10/2015 |
| WO | WO 15/187986 | 12/2015 |
| WO | WO 16/043603 | 3/2016 |
| WO | WO 17/030447 | 2/2017 |
| WO | WO 17/150990 | 9/2017 |
| WO | WO 17/158474 | 9/2017 |
| WO | WO 2017/158544 | 9/2017 |
| WO | WO 2017/160166 | 9/2017 |
| WO | WO 2017/216708 | 12/2017 |
| WO | WO 19/003094 | 1/2019 |

OTHER PUBLICATIONS

Pad A Cheek, LLC, Sleep apnea can make beautiful sleep elusive, (http://web.archive.org/web/20070701000000*/http://www.padacheek.com/;Wayback Machine), downloaded Feb. 24, 2020, 3 pp.

Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-series-cpap-humidifier-manual.pdf.

International Search Report and Written Opinion of PCT/IB2019/052057 dated Jun. 13, 2019 in 13 pages.

* cited by examiner

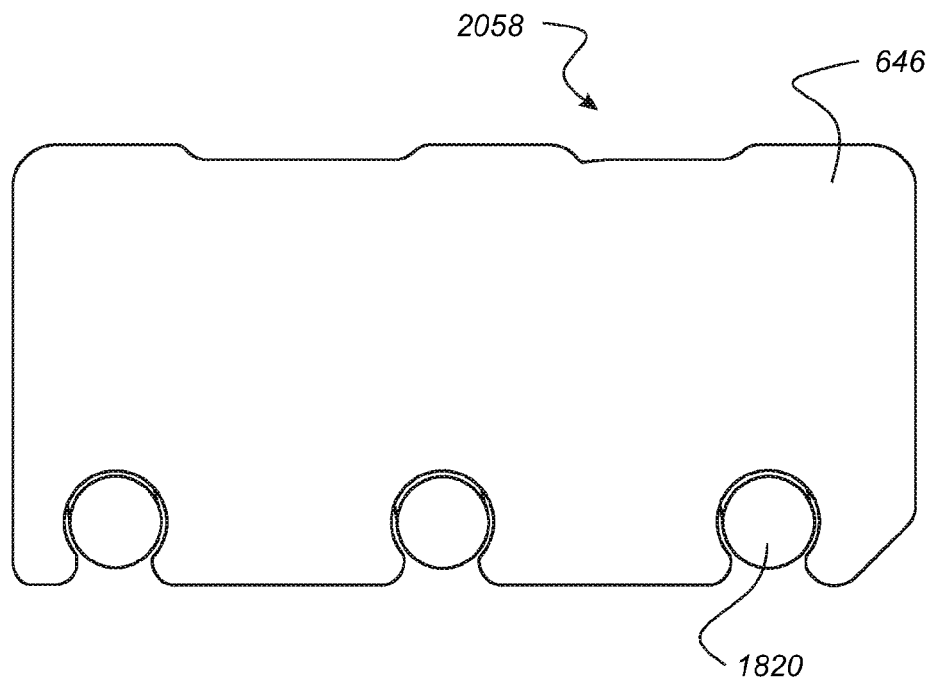
FIG. 51A
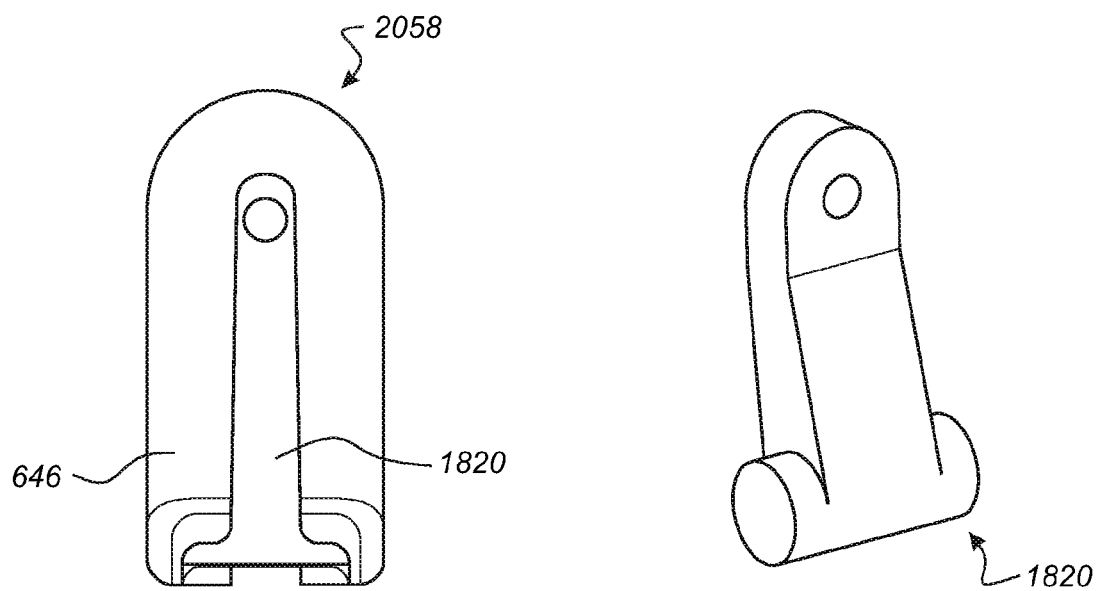
FIG. 51B
FIG. 51C

HEADGEAR WITH LOCK DISENGAGEMENT MECHANISM

BACKGROUND

Field

The present disclosure relates to respiratory therapy systems. In particular, the disclosure relates to interface assemblies for use in respiratory therapy and portions thereof.

Description of Related Art

Masks providing a substantially air-tight seal between a wearer and the mask are used in a variety of fields (e.g. gas masks, diving masks, respiratory therapy masks). Some of these masks use headgear including one or more straps to secure the mask against the face of the wearer.

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnea (OSA), a condition in which a patient's airway intermittently collapses, during sleep, preventing the patient from breathing for a period of time. The cessation of breathing, or apnea, results in the patient awakening. Repetitive and frequent apneas may result in the patient rarely achieving a full and restorative night's sleep.

CPAP therapy involves the delivery of a supply of continuous positive air pressure to the airway of the patient via a respiratory mask. The continuous positive pressure acts as a splint within the patient's airway, which secures the airway in an open position such that the patient's breathing and sleep are not interrupted.

Respiratory masks typically comprise a patient interface and a headgear, wherein the patient interface is configured to deliver the supply of continuous positive air pressure to the patient's airway via a seal or cushion that forms an airtight seal in or around the patient's nose and/or mouth. Respiratory masks are available in a range of styles including full-face, nasal, direct nasal and oral masks, which create an airtight seal with the nose and/or mouth. The seal or cushion is held in place on the patient's face by the headgear. In order to maintain an airtight seal, the headgear should provide support to the patient interface such that it is held in a stable position relative to the patient's face during use. Such respiratory masks may also be used to deliver NIV and other therapies.

SUMMARY

The systems, methods and devices described herein have innovative aspects, no single one of which is indispensable or solely responsible for their desirable attributes. Without limiting the scope of the claims, some of the advantageous features will now be summarized.

In some configurations, a headgear for a respiratory mask comprises at least one strap comprising a filament, a directional lock having an engaged configuration and a disengaged configuration with respect to the filament, and a disengaging member operable to hold the lock in the disengaged configuration.

In some configurations, the headgear further comprises an actuator configured to act on the disengaging member to cause the disengaging member to hold the lock in the disengaged configuration.

In some configurations, the actuator is selectively operable to act on the disengaging member. In some such configurations, the actuator is coupled to one of a movable bar or button or a handle.

In some configurations, the actuator is configured to automatically act on the disengaging member when a user pulls a mask away from the user's face. In some such configurations, the actuator comprises an arm coupled to the at least one strap and configured to be movable relative to the respiratory mask.

In some configurations, the disengaging member is normally biased away from holding the lock in its disengaged configuration.

In some configurations, the at least one strap comprises a first strap portion and a second strap portion, wherein the filament is attached to one of the first strap portion and the second strap portion and the first strap portion and the second strap portion are movable relative to one another to vary a length of the at least one strap.

In some configurations, the at least one strap extends between a head-engaging portion and a mask-engaging portion of the headgear.

In some configurations, a headgear for a respiratory mask comprises at least one strap comprising a filament, a directional lock configured to limit movement of the filament in a direction until a minimum force in said direction is applied to the filament, and a disengaging member that is operable to reduce the minimum force required to move the filament in said direction.

In some configurations, the disengaging member is normally biased away from a position in which the minimum force is reduced.

In some configurations, the minimum force of the directional lock is between about 2 Newtons and 8 Newtons. In some configurations, two or more directional locks with a minimum force between 2 Newtons and 8 Newtons may be combined to yield an overall minimum force between 4 and 16 Newtons, or between 16 and 32 Newtons.

In some configurations, the minimum force of the directional lock is between about 4 Newtons and 6 Newtons. In some configurations, two or more directional locks with a minimum force between 4 Newtons and 6 Newtons may be combined to yield an overall minimum force between 8 and 12 Newtons, or between 16 and 32 Newtons.

In some configurations, the headgear further comprises at least one strap that does not include a filament.

In some configurations, the headgear further comprises an actuator configured to operate the disengaging member.

In some configurations, the actuator is selectively operable to act on the disengaging member. In some such configurations, the actuator is coupled to one of a movable bar, a button or a handle.

In some configurations, the actuator is configured to automatically act on the disengaging member when a user pulls the mask away from the user's face. In some such configurations, the actuator comprises an arm coupled to the at least one strap and configured to be movable relative to the respiratory mask.

In some configurations, a mask assembly comprises any of the above-described headgear. The mask assembly further comprises a mask. The mask comprises a frame and a cushion module having a housing and a seal. The mask further comprises a connection arrangement configured to connect the cushion module to the frame. The connection arrangement comprises at least one protrusion located on one of the cushion module and the frame and at least one recess located on the other of the cushion module and the frame. The at least one protrusion is configured to engage the at least one recess to secure the cushion module to the frame.

In some configurations, the cushion module comprises a cylindrical wall defining an opening that receives a collar of the frame.

In some configurations, the at least one protrusion extends in a circumferential direction on the cylindrical wall and the at least one recess extends in a circumferential direction on the collar.

In some configurations, the cylindrical wall extends into a breathing chamber of the cushion module from an outer wall of the housing.

In some configurations, an alignment feature comprises a recess defined by one of the cushion module and the frame and a protrusion defined by the other of the cushion module and the frame. The protrusion is configured to engage the recess to facilitate rotational alignment of the cushion module relative to the frame.

In some configurations, the headgear comprises a yoke configured to connect the headgear to the mask.

In some configurations, the yoke comprises a central portion and at least one arm extending from the central portion. The at least one arm is configured to connect to the at least one strap of the headgear.

In some configurations, the frame comprises a lip and the yoke comprises at least one hooked connection finger configured to selectively engage the lip to secure the yoke to the frame.

In some configurations, the lip extends along a perimeter of the frame.

In some configurations, the lip extends from a front surface of the frame.

In some configurations, the at least one hooked connection finger is located adjacent a junction between the at least one arm and the central portion.

In some configurations, a recess is located adjacent to and configured to facilitate deflection of the at least one hooked connection finger.

In some configurations, a gap is located adjacent to and configured to facilitate deflection of the at least one hooked connection finger and/or to decouple movement of the at least one arm and the at least one hooked connection finger.

In some configurations, the gap extends entirely through a rear wall of the yoke.

In some configurations, the at least one strap comprises a plurality of straps and the at least one arm comprises a plurality of arms.

In some configurations, the number of straps is different than the number of arms.

In some configurations, a mask assembly includes a cushion module comprising a housing, a seal for sealing with a patient's face, an inlet opening to the cushion module and a plurality of exhaust vent holes located on the housing above the inlet opening. The mask assembly also includes a frame comprising at least one protrusion that engages the inlet opening of the cushion module to attach the frame to the cushion module. The frame has a conduit connector portion for connecting to a conduit through which respiratory gas is delivered. The conduit connector portion extends below the inlet opening when the frame is attached to the cushion module. A yoke is configured to attach to the frame. The yoke comprises a central portion that substantially aligns with the inlet opening of the cushion module when the yoke is attached to the frame and arms that extend laterally from the central portion.

In some configurations, an entirety of the central portion of the yoke is located below the plurality of exhaust vent holes when the yoke and the cushion module are attached to the frame.

In some configurations, an entirety of the yoke is located below the uppermost extent of the plurality of exhaust vent holes when the yoke and the cushion module are attached to the frame.

In some configurations, a maximum width of the frame is less than or equal to a maximum width of the central portion of the yoke.

In some configurations, the frame comprises a lip and the yoke comprises at least one hooked connection finger configured to selectively engage the lip to secure the yoke to the frame.

In some configurations, the lip extends along a perimeter of the frame.

In some configurations, the lip extends from a front surface of the frame.

In some configurations, the at least one hooked connection finger comprises a hooked connection finger located adjacent a junction between the each of the arms and the central portion.

In some configurations, a recess is located adjacent to and configured to facilitate deflection of the at least one hooked connection finger.

In some configurations, a gap is located adjacent to each of the hooked connection fingers and configured to facilitate deflection of the associated hooked connection finger and/or to decouple movement of each of the arms and the associated hooked connection finger.

In some configurations, the gap extends entirely through a rear wall of the yoke.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 51A is a side view of a non-disengageable lock.

FIG. 51B is a front view of a non-disengageable lock.

FIG. 51C is a perspective view of a washer of a non-disengageable lock.

DETAILED DESCRIPTION

Figure 1:
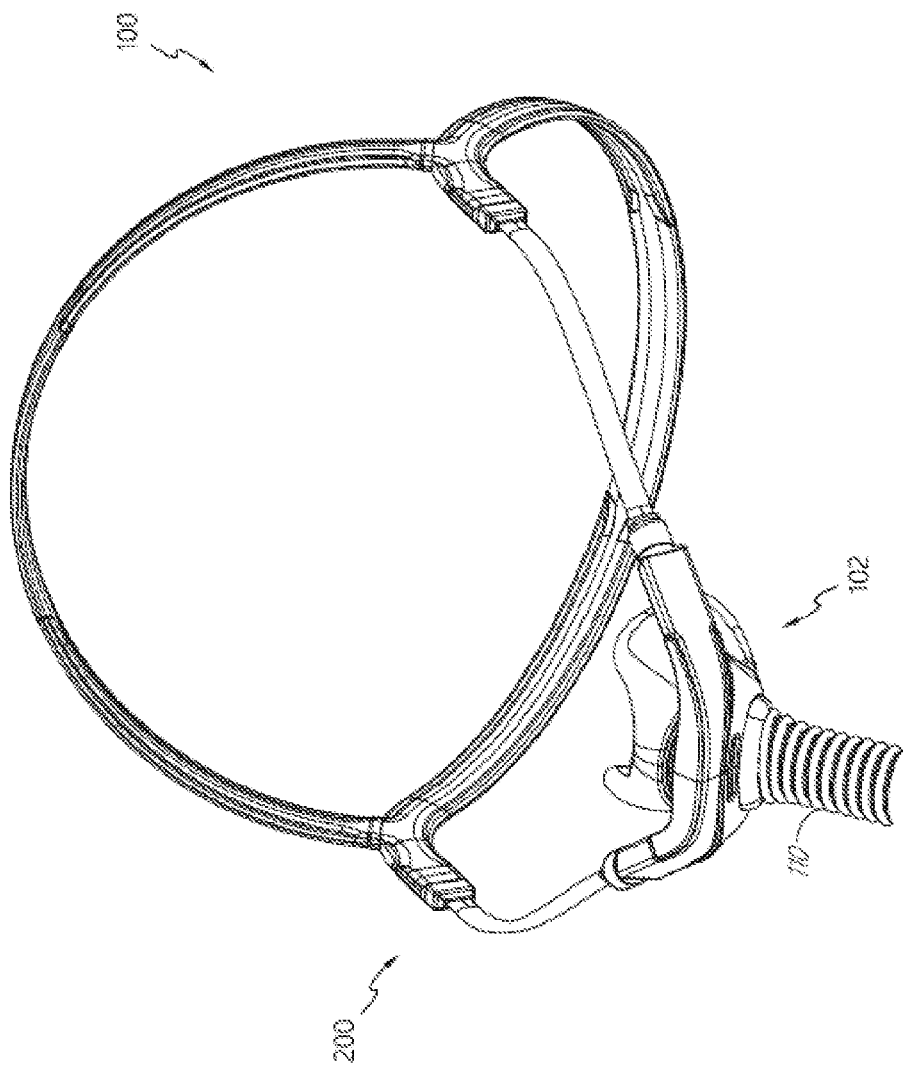
FIG. 1 is a perspective view of a mask assembly, including a headgear assembly, a seal assembly, and a frame assembly.
Figure 2:
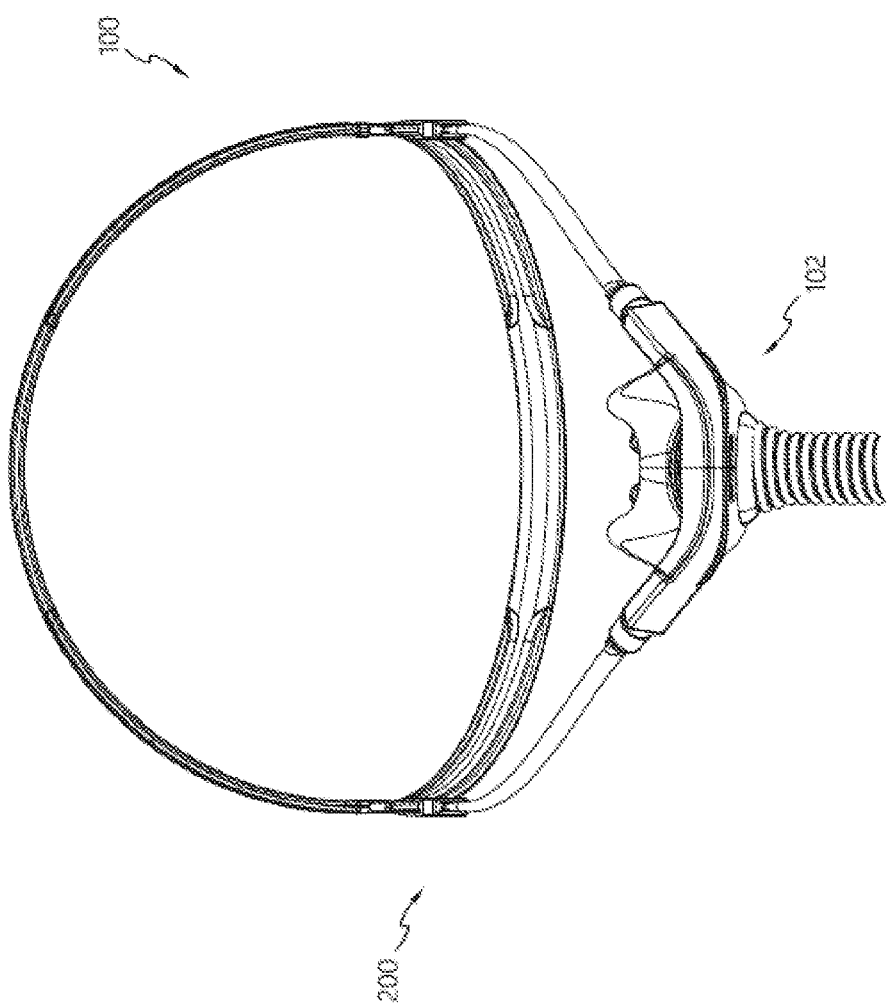
FIGS. 2, 3 and 4 are a front view, side view, and a rear perspective view, respectively, of the mask assembly of FIG. 1.
Figure 3:
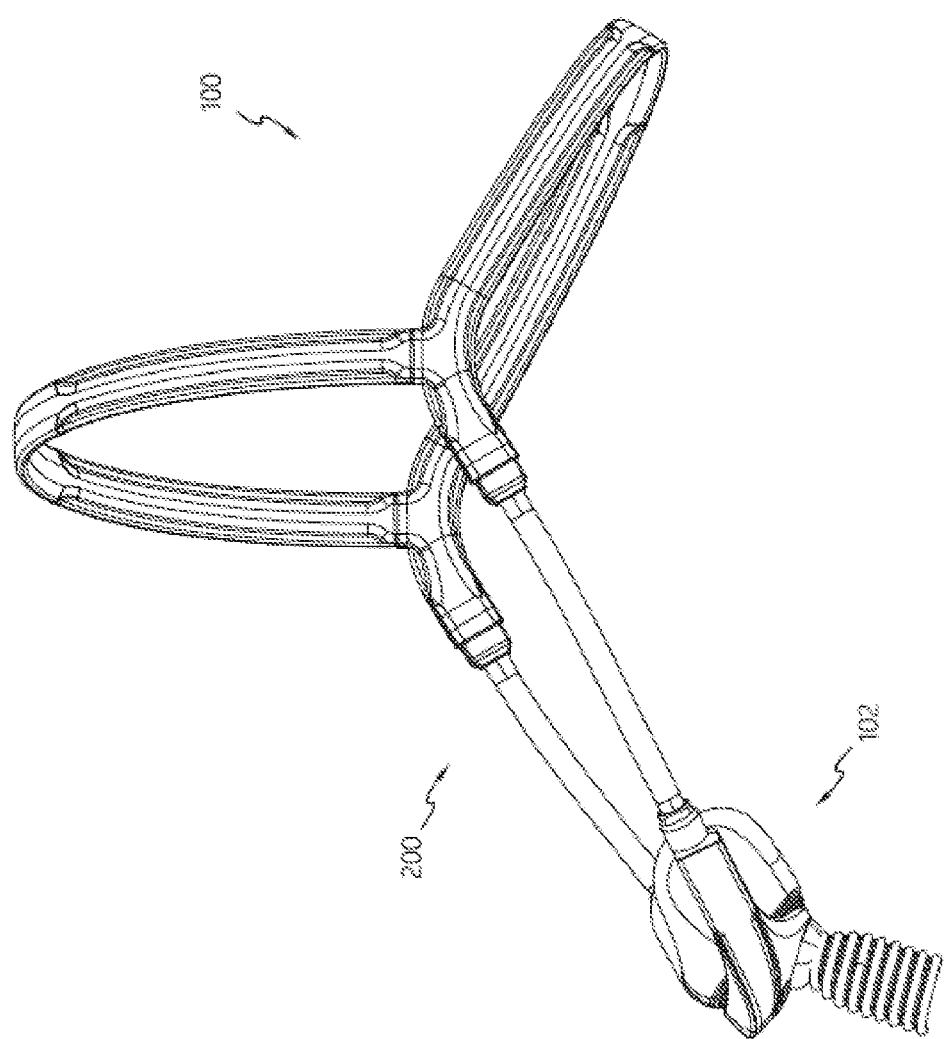
Figure 4:
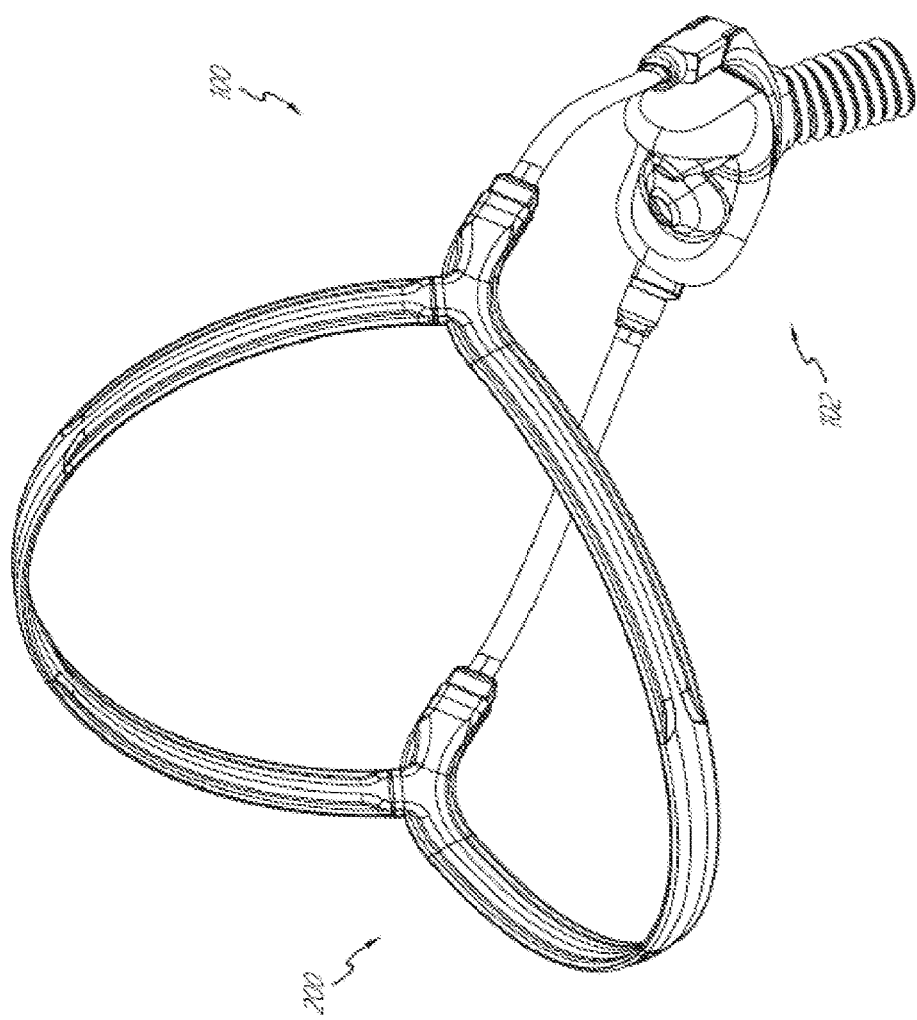
Figure 5:
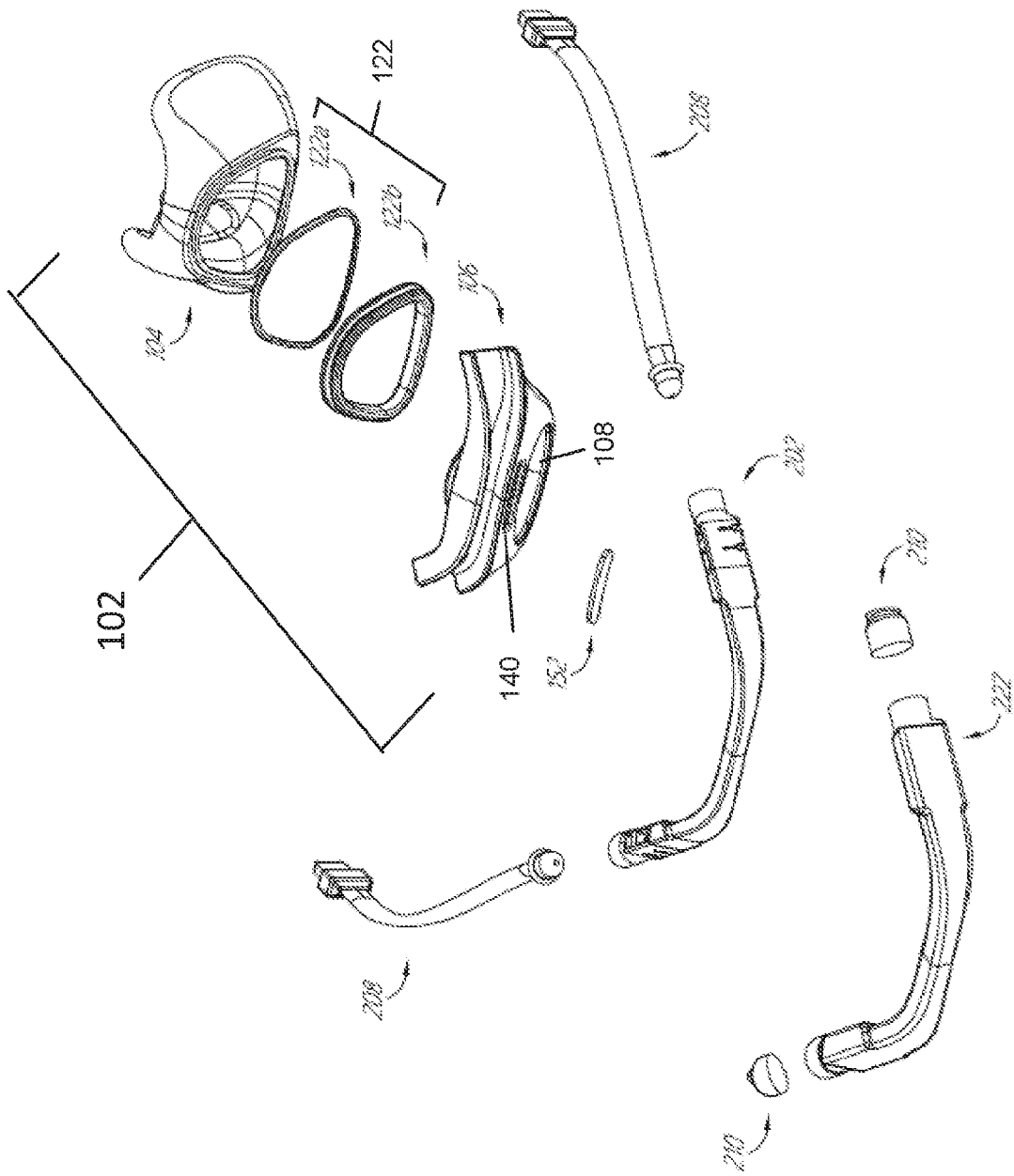
FIG. 5 is an exploded view of the seal assembly, frame assembly, and a front portion of the headgear assembly.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "horizontal," "vertical," "front," "back," "left," "right," "rear," and "side" describe the orientation and/or location of portions of the components or elements within a consistent but arbitrary frame of reference which is made clear by reference to the text and the associated drawings describing the components or elements under discussion, which in the context of a patient interface is often in an as-worn orientation with the user's head in an upright orientation. Moreover, terms such as "first," "second," "third," and so on may be used to describe separate components. Such terminology may include the words specifically mentioned above, derivatives thereof, and words of similar import.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavor in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

The present disclosure relates to a respiratory interface assembly or respiratory mask assembly incorporating one or more retention or lock arrangements configured to retain the interface assembly in an adjusted position (e.g., automatically adjusted), which may be a position that is sized to fit a particular user of the interface assembly, and a release arrangement (e.g., a manual release) configured to release the retention or lock arrangement(s) and permit the interface assembly to move from the adjusted position against little to no force—or a force that is less than (e.g., significantly less than) a retention or lock force of the retention or lock arrangement(s).

FIGS. 1 to 6 illustrate one example of a respiratory interface system or respiratory mask system 100 for the delivery of respiratory therapy to a patient. The mask system 100 may comprise an interface, such as a mask 102. In the illustrated arrangement, the mask 102 comprises a seal, or seal module, and a frame, as described in further detail herein. The illustrated mask system 100 also includes a headgear assembly 200 (which can be referred to simply as "headgear" herein). The mask 102 and headgear 200 may comprise a connection system to attach the headgear 200 to the mask 102. Various forms of connection systems may be used to attach the headgear 200 to the mask 102. Similarly, the mask 102 may be coupled to at least one and possibly multiple different types of headgear.

The mask 102 may comprise a seal 104 and a frame 106. The seal 104 can be configured for sealing around and/or underneath a patient's mouth and/or nose. In the illustrated arrangement, the seal 104 is a nasal seal configured to deliver the flow of breathing gases only to the user's nose. In particular, the illustrated seal 104 includes a pair of nasal pillows configured to create a seal with the user's nares and a secondary sealing portion that surrounds the nasal pillows and is configured to create a secondary seal with one or more of an underside of the user's nose, side portions of the user's nose and the user's upper lip. However, features of the present disclosure can be implemented with other mask systems having other types of mask seals, such as full-face seals, for example and without limitation. The frame 106 is configured for supporting the seal 104 and attaching the seal 104 to the headgear 200. The frame 106 may also comprise a gas inlet 108 (FIG. 5) configured to attach to a gas conduit 110 for delivering a flow of breathing gas to the patient via the mask 102. The seal 104 can include an attachment frame or clip 122, which in some arrangements can include a first portion 122*a* and a second portion 122*b* that capture a rim of the seal 104 between them. The clip 122 is configured to selectively connect to the frame 106, such as by a snap-fit, friction fit or other suitable arrangement. The frame 106 can include a vent 140, which is configured to exhaust gases from an interior of the seal 104. Optionally, the mask 102 can include a vent insert or diffuser 152 that covers the vent 140 to control the exhaust flow.

The headgear 200 of the respiratory mask system 100 is used to hold the mask 102 to the patient's face. The headgear 200 is typically attached to the mask 102 and wraps around the rear of the patient's head to hold the mask 102 in sealed contact with the patient's face.

In one form, the headgear assembly 200 may comprise a yoke or collector 202, which is configured to attach to the mask 102, as described in greater detail herein.

The yoke 202 may be configured to attach to straps of the headgear 200 such that the straps and yoke 202 cooperate to form a closed loop that surrounds the head of the user. In the illustrated embodiment, the headgear 200 comprises an assembly of straps, including a rear strap 204 configured to wrap behind a patient's head, an upper strap 206 configured to wrap over the top of a patient's head, and a pair of front straps 208 (FIG. 6) configured to extend along the patient's cheeks during use. In one form, each front strap 208 is attached to the rear strap 204 of the headgear assembly 200, e.g., to a free end 207 of the rear strap 204 or a connector coupled to the free end 207, by a rear connector 205. In another form, the rear strap 204 comprises side extensions that form front straps to extend along the patient's cheeks during use.

In one form, the headgear 200 can be adjustable (e.g. manually adjustable, automatically adjustable) and/or can incorporate one or more locks (e.g. directional locks 1800) that allow the headgear 200 to reduce in length with a relatively low amount of resistance and resist an increase in length of the headgear 200. In some configurations, a locking force of the directional locks 1800 can be overcome to allow lengthening of the headgear 200 for donning of the interface assembly 100. In some forms, the yoke 202 may form a collector for filaments used in an automatically adjustable headgear system. In this form, the yoke 202 may incorporate one or more directional locks 1800, each of which can comprise one or more lock elements, which can be referred to herein as lock washers or washers. The lock washers are configured to frictionally engage with the filament during elongation of the headgear 200, but allow relatively friction-free movement during retraction of the headgear 200. In some configurations, the headgear 200, or interface assembly 100, includes a release mechanism or arrangement that is configured to release or hold open the directional locks 1800 to allow for low-friction movement while a control or other actuator is operated by a user, and provide high-friction resistance if the control or actuator is not engaged.

The directional locks 1800 may be incorporated into the ends of the yoke/collector 202 and the body of the yoke/collector 202 may be substantially hollow to receive the filaments within the body. The headgear 200 or any portion thereof can be configured in accordance with any of the embodiments disclosed in Applicant's U.S. Publication No. 2016/0082217, U.S. application Ser. No. 14/856,193, filed Sep. 16, 2015, and PCT Publication No. WO2016/043603, the entireties of which are incorporated by reference herein.

Figure 6:
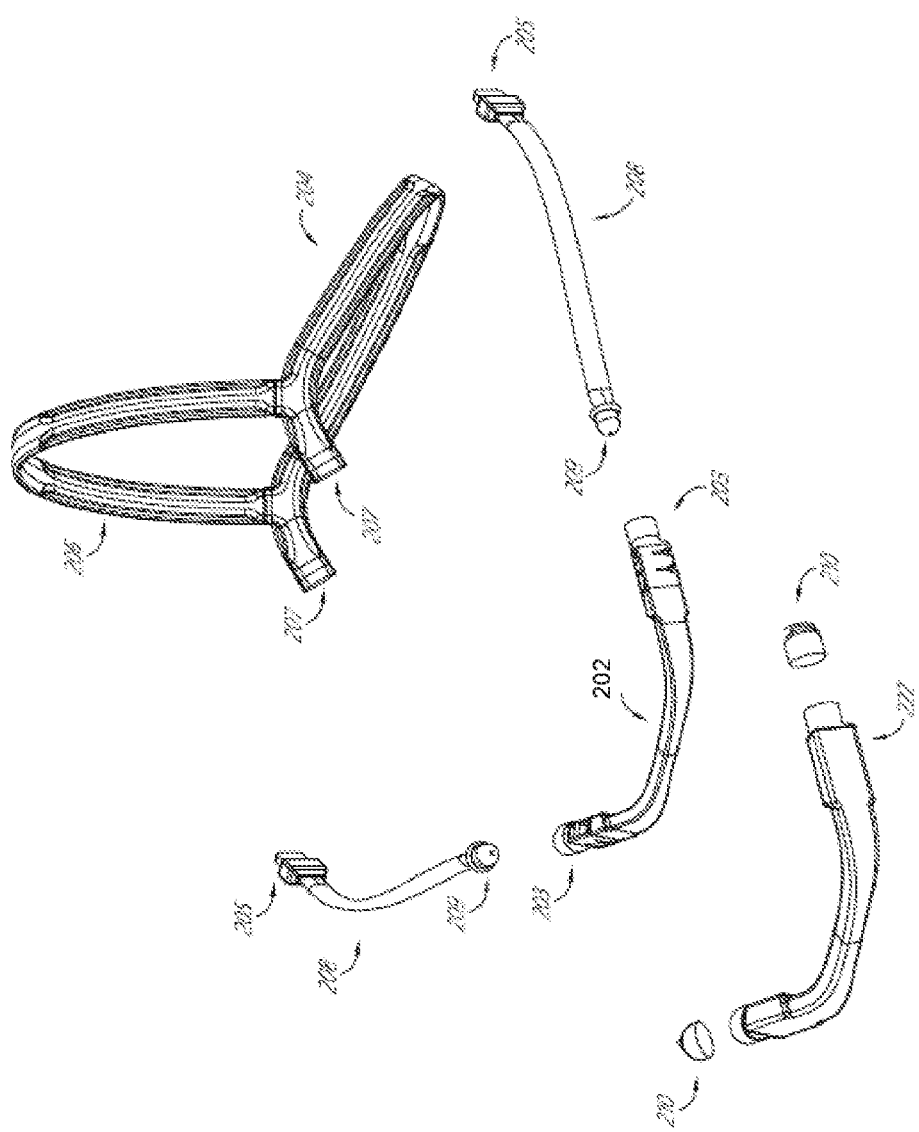
FIG. 6 is an exploded view of one form of headgear assembly.

With reference to FIG. 6, each front strap 208 may comprise a free end to which may be attached a connector 209. Each connector 209 may engage with a complementary strap connector 203 located on the yoke 202. Preferably, the yoke 202 is substantially elongate and comprises a strap connector 203 located at or near each end of the yoke 202. The connection between the front straps 208 and yoke 202 may be any suitable form of connection, such as a snap-fit connection, a screw and thread type connection, or a hooked connection. In one form, as shown in FIG. 6, each strap connector 203 comprises a cap 210 located at each end of the yoke 202. Each cap 210 may comprise an opening, such as an aperture or recess, configured to receive the connector 209 of the front strap 208 in a snap-fit arrangement to attach the yoke 202 to the front straps 208 of the headgear assembly 200.

As mentioned above, the yoke 202 may also be configured to attach to the frame 106 of the mask 102. In one form, the frame 106 may comprise a recessed region configured to receive at least a portion of the yoke 202 therein when the yoke 202 and frame 106 are attached together. A cover sleeve, or front portion 222 can be configured to facilitate the removable connection of the yoke 202 with the frame 106.

Figure 7:
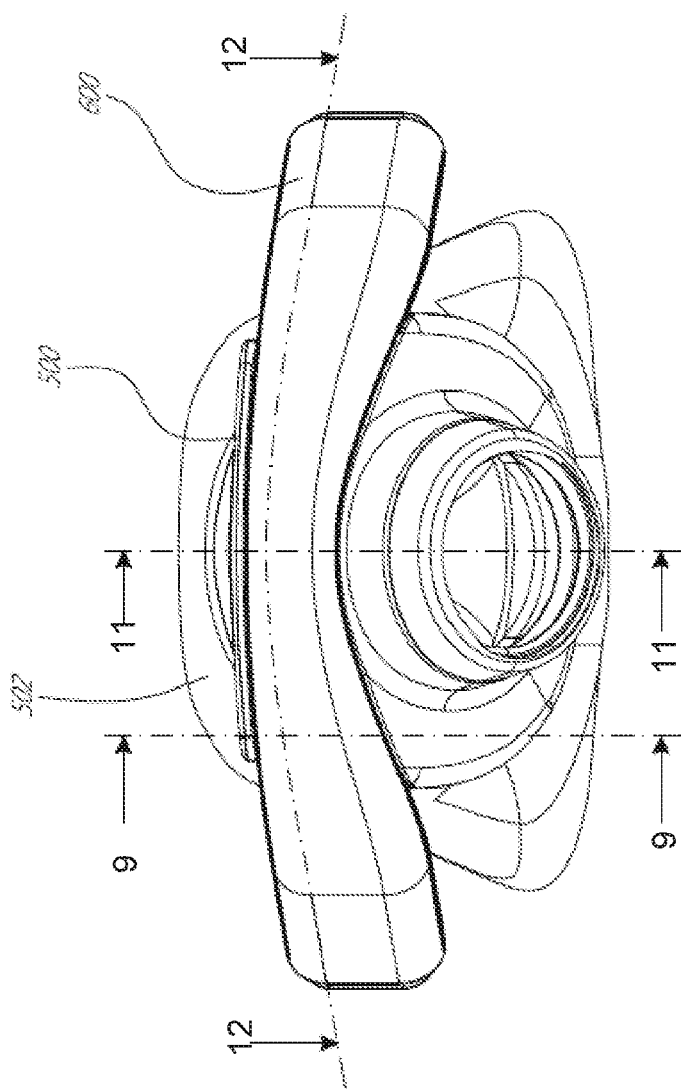
FIG. 7 is a front view of an example embodiment of an assembled frame, cushion, and yoke.
Figure 8:
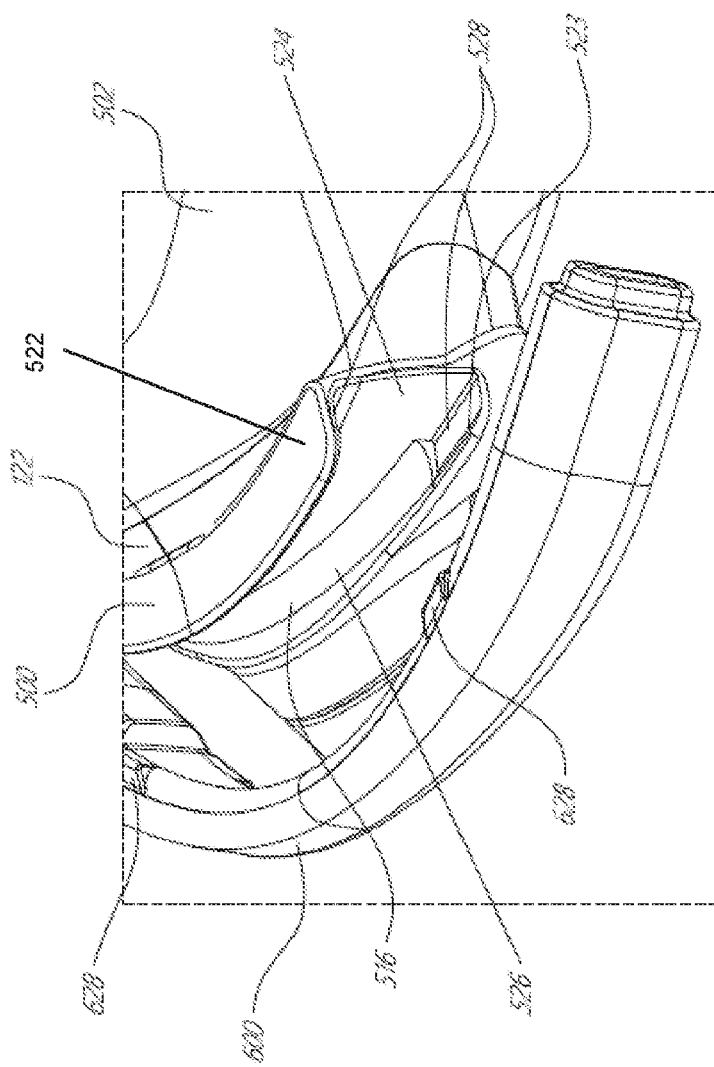
FIG. 8 is a partial perspective view of the yoke of FIG. 7 disconnected from the frame.
Figure 9:
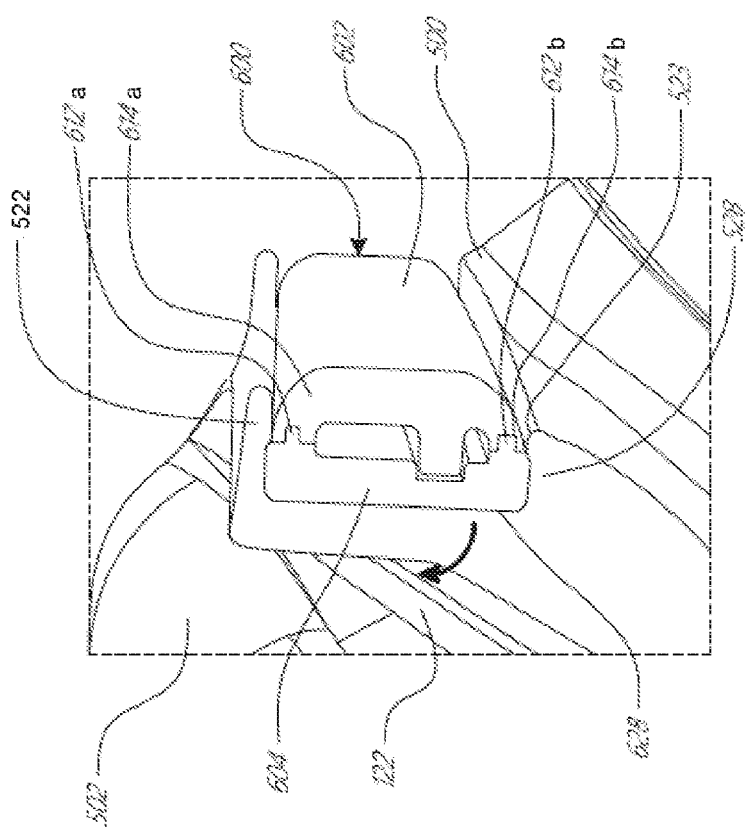
FIG. 9 is a section view of the assembled frame and yoke taken along line 9-9 in FIG. 7.

FIGS. 7 to 9 illustrate another example embodiment of a yoke 600 and cushion or seal 502 coupled to a frame 500. The yoke 600, seal 502, and/or frame 500 can be similar to the yoke 202, cushion or seal 104, and/or frame 106, respectively, except as otherwise described below. The frame 500 includes a yoke channel 516 configured to receive the yoke 600 in use. The yoke channel 516 is formed or defined by an upper wall 522, rear wall 524, and lower wall 526. The yoke 600 has increased asymmetry between upper and lower edges of the yoke 600, for example, compared to the yoke 202. In the illustrated embodiment, the upper edge of the yoke 600 is straighter than the lower edge. The asymmetry advantageously provides improved visual cues as to the correct orientation for assembly of the yoke 600 to the frame 500 and helps inhibit incorrect assembly.

As shown in FIG. 8, the yoke channel 516 includes connector recesses 528 in the upper 522 and lower 526 walls. In the illustrated embodiment, a connector recess 528 is positioned at, adjacent, or proximate each lateral end of the yoke channel 516. The connector recesses 528 at least partially define or form retention lips 523 at or along front edges of the yoke channel 516 (e.g., at or along front edges of internally facing surfaces of the upper wall 522 and lower wall 526). The yoke 600 includes connector protrusions 628 protruding rearwardly from upper, lower, and/or rear surfaces of the yoke 600. In the illustrated embodiment, the yoke 600 includes a connector protrusion 628 on each side of a center of the yoke 600. In the illustrated embodiment, the yoke 600 includes a yoke front 602 and yoke back 604 that are coupled together, as described in greater detail herein, and the connector protrusions 628 are formed in the yoke back 604. The connector recesses 528 are configured to receive the connector protrusions 628 when the frame 500 and yoke 600 are coupled together to form a snap-fit connection between the frame 500 and yoke 600. When the frame 500 and yoke 600 are coupled together, the retention lips 523 engage the yoke 600 forward of the connector protrusions 628 to contribute to the snap-fit connection and retain the yoke 600 in the yoke channel 516. In the illustrated embodiment, the connector protrusions 628 and connector recesses 528 have a square or rectangular profile, which inhibits the yoke 600 from rotating out of the yoke channel 516, for example, in the direction indicated by the arrow in FIG. 9.

Figure 10B:
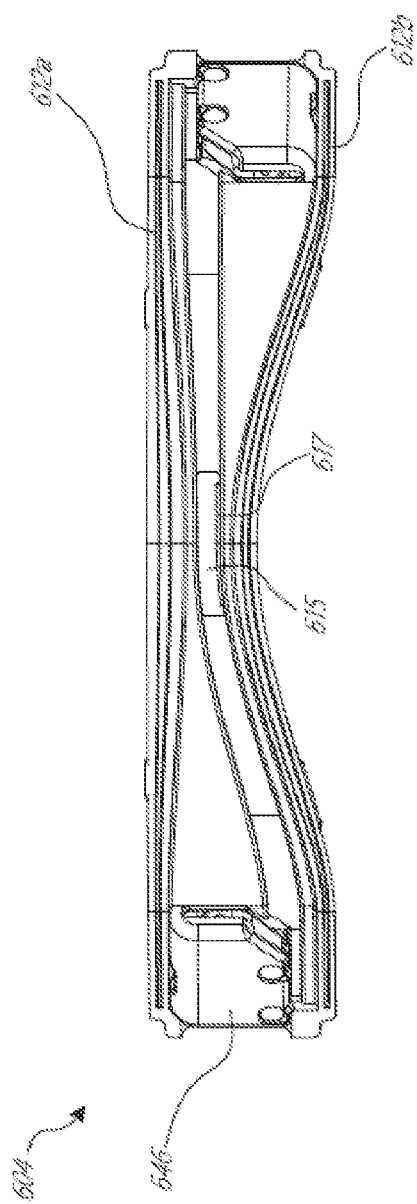
FIG. 10B is a front view of the yoke rear portion of FIG. 10A.
Figure 10C:
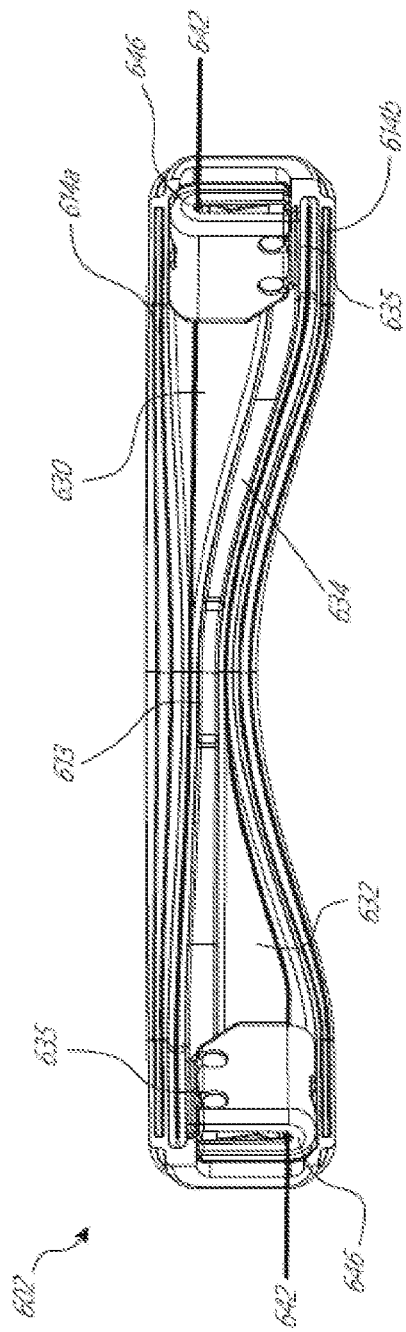
FIG. 10C is a rear view of a yoke front portion of the yoke of FIG. 7.
Figure 11:
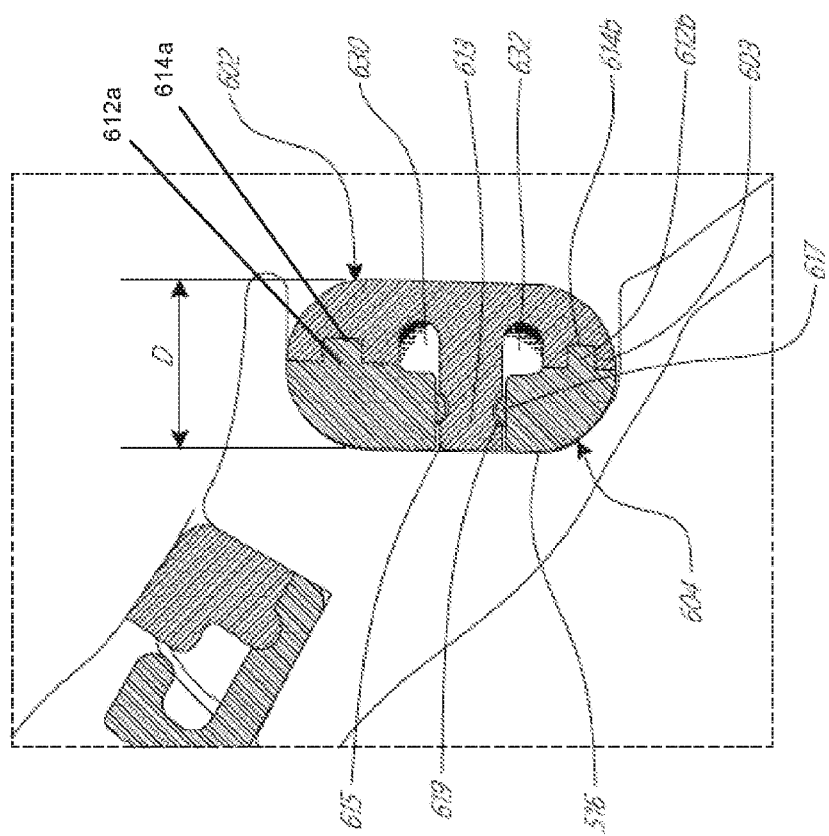
FIG. 11 is a section view of the assembled frame and yoke of FIG. 7 taken along line 11-11 in FIG. 7.

In some embodiments, the yoke 600 has an oval or substantially oval cross-section, for example, as shown in FIG. 11. This shape advantageously reduces the size or bulk of the yoke 600 and/or provides an improved aesthetic appearance. The lock washer housings 646, discussed in greater detail herein, can have a D-shaped, substantially D-shaped, U-shaped, or substantially U-shaped cross-section, for example as shown in FIGS. 10B and 10C, to allow for and/or contribute to the overall oval or substantially oval cross-section of the yoke 600. The washer housings 646 can be positioned in opposite vertical orientations relative to each other. In other words, one of the washer housings 646, e.g., the left washer housing 646 as shown in FIG. 10C, can be oriented as an upward-facing U-shape and the other washer housing 646, e.g., the right washer housing 646 in FIG. 10C, can be oriented as a downward-facing U-shape. This arrangement and orientation can advantageously help allow receptacles or collectors for the excess portion of the filaments used in an automatically adjustable headgear system, which can be referred to herein as line tracks 630, 632, to extend above and below the left and right washer housings 646, respectively, as discussed in greater detail herein. As shown in FIG. 11, in the illustrated embodiment, the yoke 600, or a central portion of the yoke 600, has a depth D that is the same as or similar to or corresponds to a depth of the yoke channel 516 such that the yoke 600 does not protrude, or does not substantially protrude, from the yoke channel 516. This advantageously reduces the overall size of the frame 500 and yoke 600 assembly.

Figure 10A:
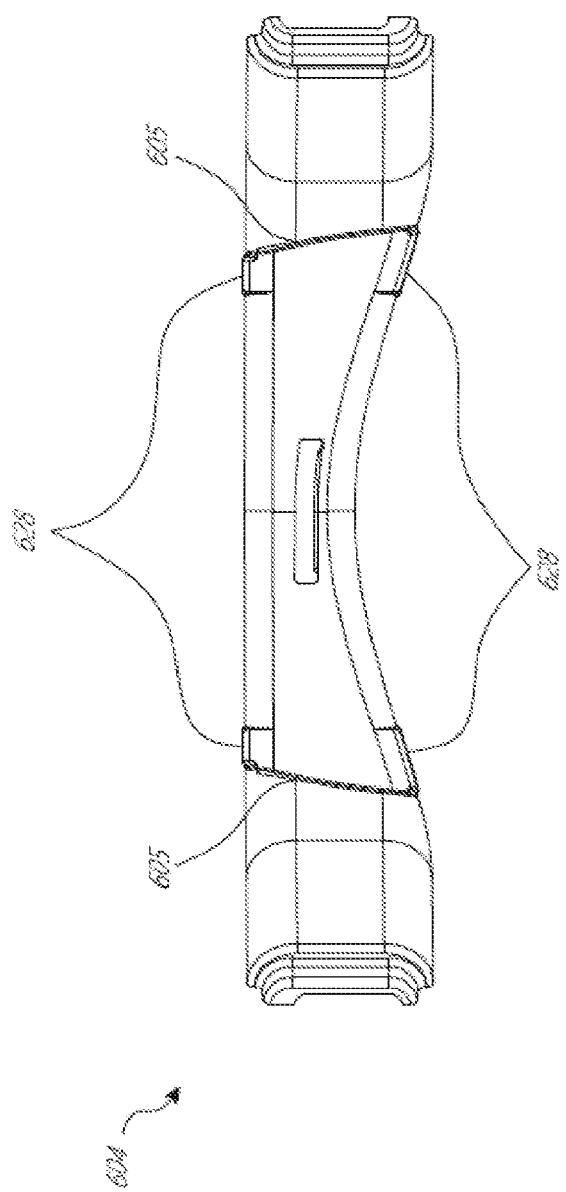
FIG. 10A is a rear view of a yoke rear portion of the yoke of FIG. 7.
Figure 12:
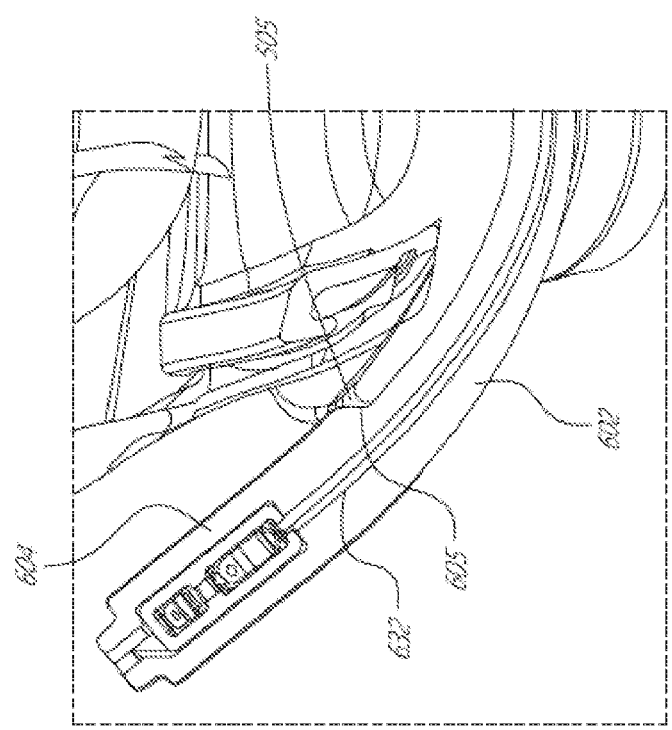
FIG. 12 is a section view of the assembled frame and yoke of FIG. 7 taken along line 12-12 in FIG. 7.
Figure 13:
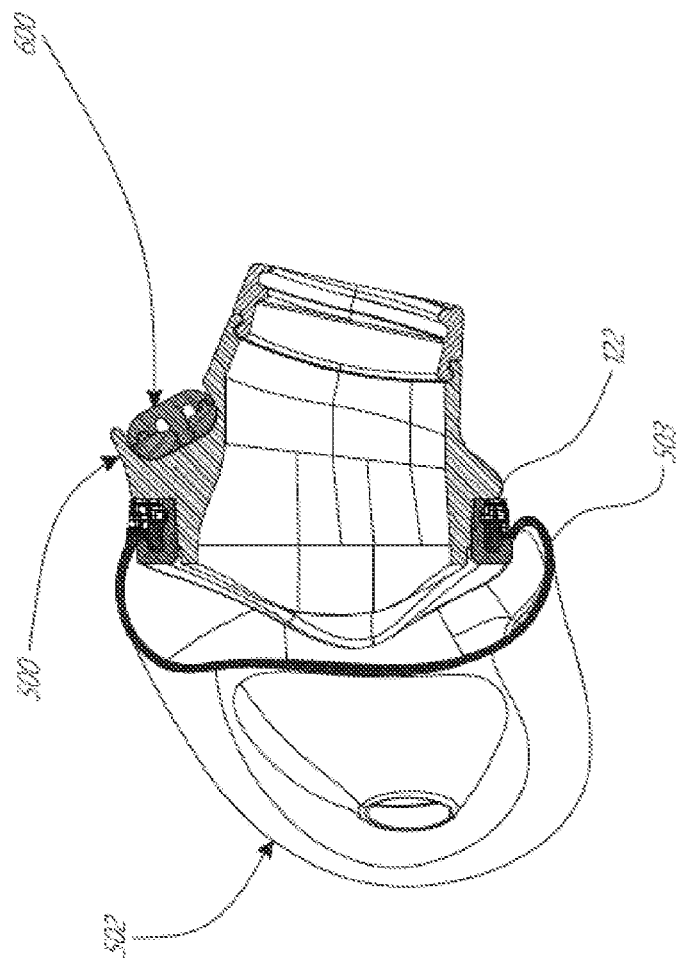
FIG. 13 is a section view of the cushion of FIG. 7.

As shown in FIGS. 10A and 12, in the illustrated embodiment, a rear or back surface of the yoke 600 includes a rearward step on each side or lateral end of the central portion of the yoke 600 such that the yoke 600 has a stepped depth. In other words, lateral portions of the yoke 600, which are positioned laterally outside of the yoke channel 516 when the yoke 600 is coupled to the frame 500, have a greater depth than the depth D of the central portion of the yoke 600, which is positioned in the yoke channel 516 when the yoke 600 is coupled to the frame 500. The steps form or define frame abutment surfaces 605 at the transitions between the central portion and lateral portions of the yoke 600. When the yoke 600 is coupled to the frame 500, each of the frame abutment surfaces 605 abuts or is positioned adjacent or proximate one of the lateral edges 505 of the frame 500 as shown in FIG. 12. The frame abutment surfaces 605 and lateral edges 505 help properly align the yoke 600 with the frame 500 during assembly. The frame abutment surfaces 605 and lateral edges 505 also or alternatively provide a more secure connection between the yoke 600 and frame 500. The reduced depth of the central portion of the yoke 600 advantageously reduces the overall size of the frame 500 and yoke 600 assembly.

Figure 14:
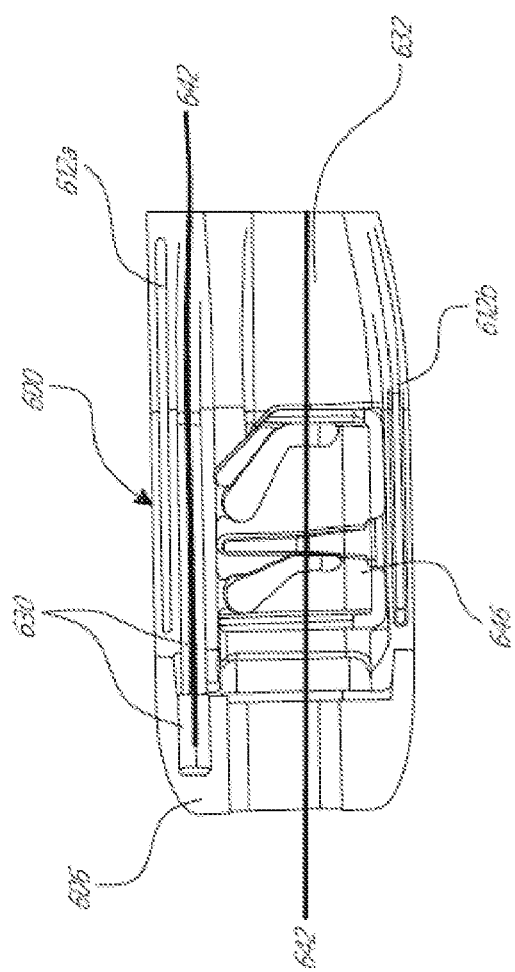
FIG. 14 is a partial section view of an alternative embodiment of the yoke showing components of a headgear adjustment mechanism.
Figure 16:
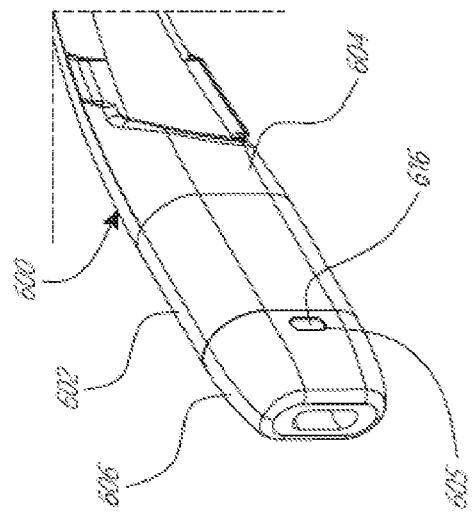
FIG. 16 is a partial rear perspective view of the assembled end cap and yoke of FIG. 15.

As shown in FIGS. 9-11, in the illustrated embodiment, the yoke 600 includes a yoke front 602 and a yoke back 604. The yoke 600 can also include two end caps 606 (as shown in FIG. 14), one at each lateral end of the yoke 600. In the illustrated embodiment, the yoke front 602 and yoke back 604 are formed as separate components that are coupled together. In the embodiment of FIGS. 9-11, a split line 603

(shown in FIG. 11) between the yoke front 602 and yoke back 604 is centered or generally centered. This can improve ease of manufacturing.

The yoke front 602 and yoke back 604 can be coupled together via a snap fit. In the illustrated embodiment, the yoke front 602 includes a yoke fastener 613 projecting rearwardly from a rear surface of the yoke front 602. In the illustrated embodiment, the yoke fastener 613 is positioned centrally or generally centrally in a vertical and/or lateral direction with respect to the yoke front 602 and is elongate in the lateral direction. The yoke back 604 includes a fastener aperture 615 that is sized, shaped, and positioned to receive the yoke fastener 613 to form a snap-fit connection when the yoke front 602 and yoke back 604 are coupled together. The central connection between the yoke front 602 and yoke back 604 via the yoke fastener 613 and fastener aperture 615 provides more rigidity to the connection between the yoke front 602 and yoke back 604 and/or provides support against or inhibits twisting between the yoke front 602 and yoke back 604. In some embodiments, the yoke front 602 instead includes the fastener aperture 615 and the yoke back 604 includes the yoke fastener 613. In some embodiments, the fastener aperture 615 includes one or more fastener bumps 617 extending along (e.g., laterally along) upper and/or lower edges of the fastener aperture 615 and protruding into the fastener aperture 615 from the upper and/or lower edges. The yoke fastener 613 includes one or more corresponding notches 619 (shown in FIG. 11) extending along (e.g., laterally along) upper and/or lower surfaces of the yoke fastener 613 that are sized, shaped, and positioned to receive the fastener bump(s) 617 to form a snap-fit connection. In some embodiments, the fastener aperture 615 includes one or more notches 619 and the yoke fastener 613 includes one or more fastener bumps 617.

Figure 22:
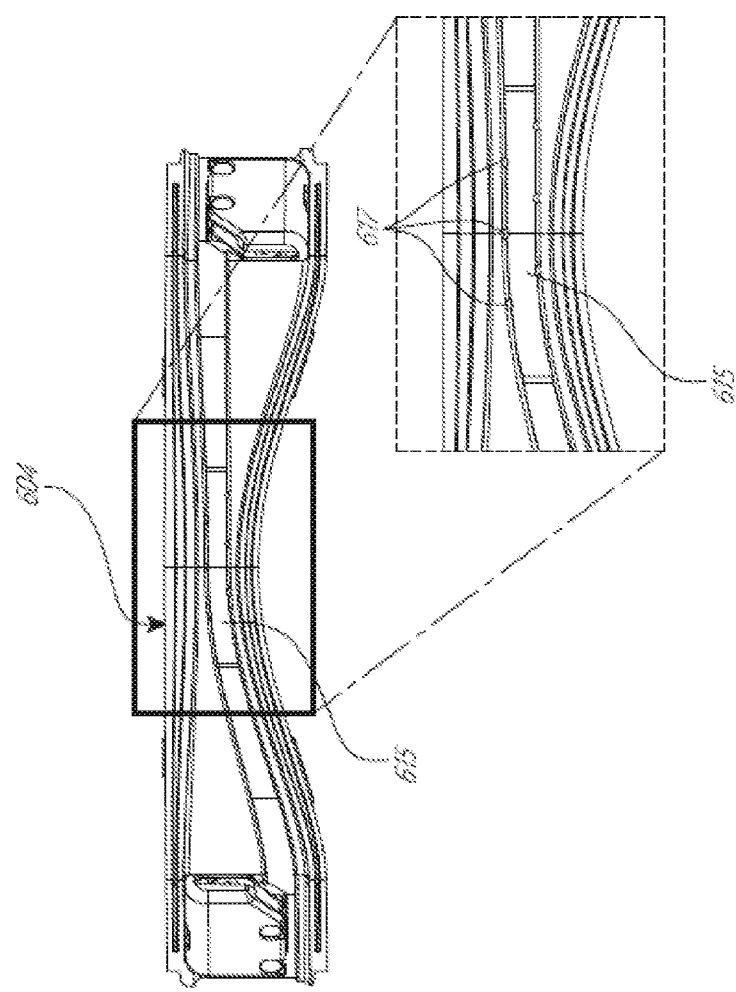
FIG. 22 is a front view of an alternative embodiment of a yoke back.
Figure 23:
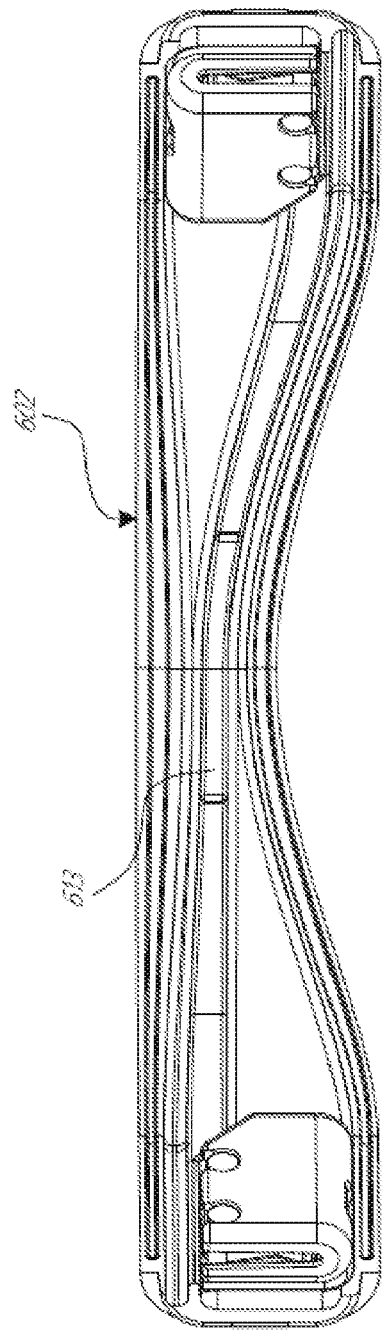
FIG. 23 is a rear view of an alternative embodiment of a yoke front configured to be coupled to the yoke back of FIG. 22.
Figure 24:
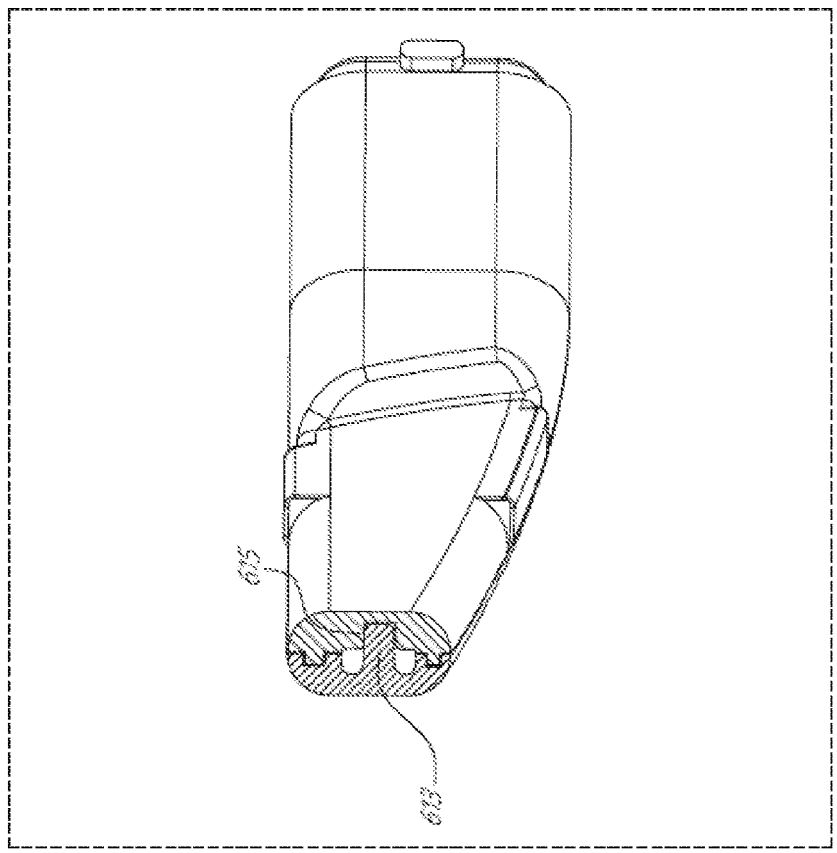
FIG. 24 is a section view of the yoke back of FIG. 22 and yoke front of FIG. 23 assembled together taken along line 24-24 in FIG. 21.

FIGS. 22-24 illustrate a variation of the yoke 600 in which the yoke back 604 includes a fastener recess 615' instead of a fastener aperture 615. The fastener recess 615' does not extend all the way through the thickness of the yoke back 604. The yoke front 602 includes a rearwardly-extending yoke fastener 613'. The fastener recess 615' is sized, shaped, and positioned to receive the yoke fastener 613' to form a friction fit or interference fit connection when the yoke front 602 and yoke back 604 are coupled together. In some such embodiments, the fastener recess 615' includes one or more interference bumps 617' on the upper and/or lower surfaces or edges of the fastener recess 615'. In the illustrated embodiment, the interference bumps 617' are elongate and extend an entire depth of the fastener recess 615'. The interference bumps 617' interfere with and help create a friction or interference fit between the fastener recess 615' and the yoke fastener 613' to help secure the yoke front 602 and yoke back 604 together. This configuration can advantageously allow for easier manufacturing, provide a neater finish (without an aperture in the yoke back 604), and/or inhibit the ingress of dirt or other debris into the line tracks 630, 632 (due to the lack of aperture, which allows the yoke 600 to be fully enclosed along its length), which can help maintain the function of the automatic headgear adjustment mechanism.

In the embodiment of FIGS. 9-11, the yoke back 604 includes an upper alignment bead 612a protruding forward from the yoke back 604 and extending along a length of the yoke back 604 adjacent or proximate the upper surface of the yoke back 604, and/or a lower alignment bead 612b protruding forward from the yoke back 604 and extending a length of the yoke back 604 adjacent or proximate the lower surface of the yoke back 604. The yoke front 602 includes an upper alignment groove 614a in a rear surface of the yoke front 602 extending along a length of the yoke front 602 adjacent or proximate the upper surface of the yoke front 602, and/or a lower alignment groove 614b in the rear surface of the yoke front 602 extending a length of the yoke front 602 adjacent or proximate the lower surface of the yoke front 602. The upper and/or lower alignment grooves 614a, 614b receive the upper and/or lower alignment beads 612a, 612b, respectively, when the yoke front 602 and yoke back 604 are coupled together. The alignment beads 612a, 612b and alignment grooves 614a, 614b help correctly align the yoke front 602 and yoke back 604. The alignment beads 612a, 612b and alignment grooves 614a, 614b can also or alternatively resist or support against torsion, e.g., between the yoke front 602 and yoke back 604. In some embodiments, the alignment beads 612a, 612b and alignment grooves 614a, 614b can be positively engaged with each other, for example, in the form of a friction fit or snap fit connection.

The end caps 606 can help secure the yoke front 602 and yoke back 604 together by clipping over or snap fitting over or onto the lateral ends of the yoke front 602 and yoke back 604. The end caps 606 can also allow for connection of a front strap (e.g., front strap 208) of a headgear (e.g., headgear 200) to the yoke 600. In some embodiments, each end cap 606 is over-molded onto a braided portion of the front strap.

Figure 15:
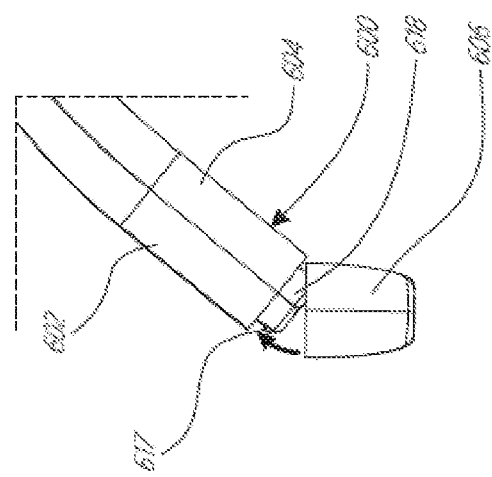
FIG. 15 shows a method of coupling an end cap onto an end of the yoke.
Figure 18:
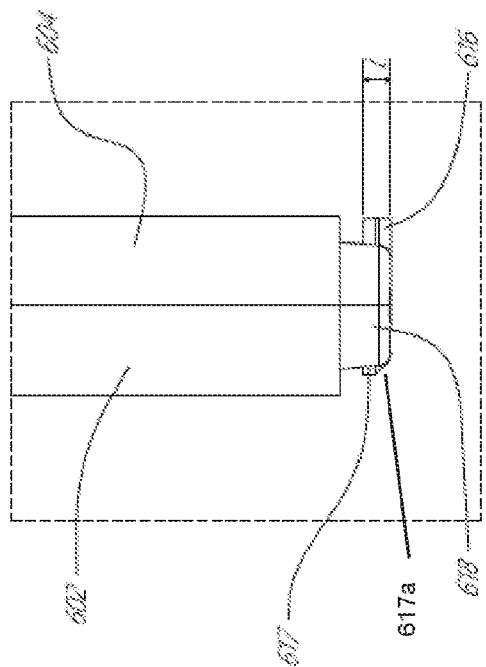
FIG. 18 is a top view of the yoke end of FIG. 17.
Figure 17:
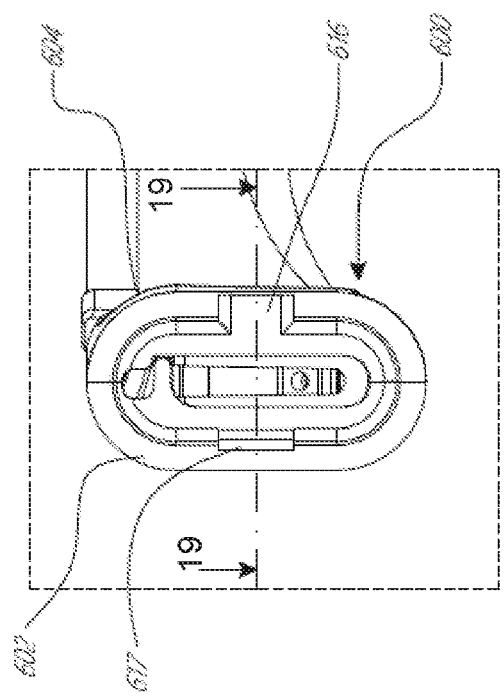
FIG. 17 is an end view of a yoke end of the yoke of FIG. 7.

As shown in FIGS. 15-21, the lateral ends of the yoke front 602 and yoke back 604 include or are formed by end cap inserts 618. The end cap inserts 618 can be integrally formed with or attached to the lateral ends of the yoke front 602 and yoke back 604. The end cap inserts 618 have a reduced dimension or profile compared to the lateral portions of the yoke 600. The end caps 606 have internal cavities 609 that receive the end cap inserts 618. During assembly, the end caps 606 can be connected over or snapped onto the end cap inserts 618 in a rotational or hinged manner, as shown in FIG. 15.

Figure 20:
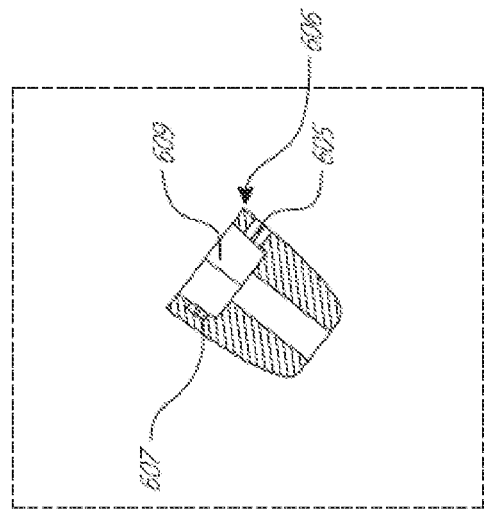
FIG. 20 is a section view of the end cap of FIG. 19.
Figure 19:
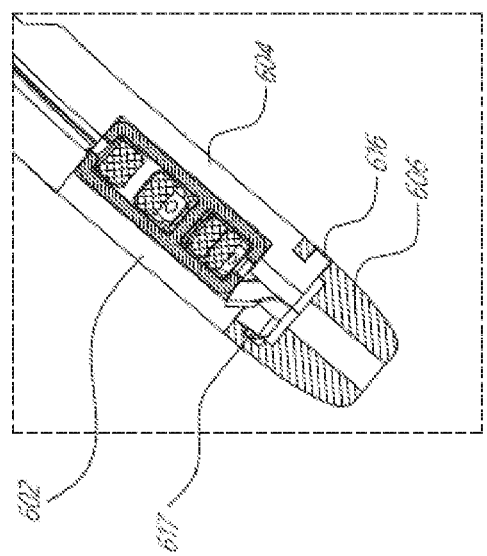
FIG. 19 is a section view of the end cap coupled to the yoke end taken along line 19-19 in FIG. 17.
Figure 21:
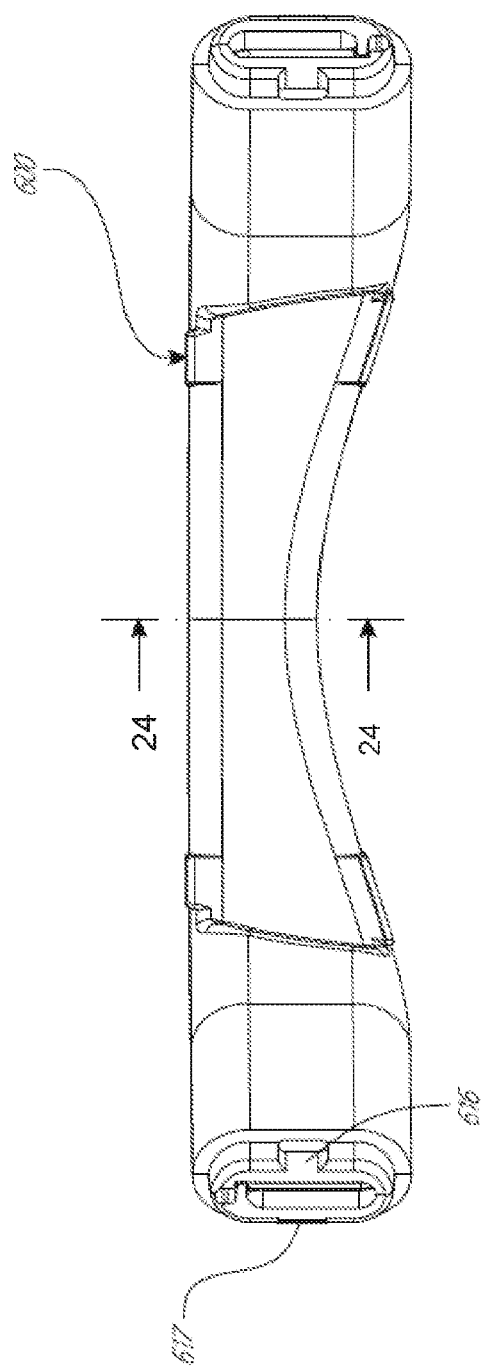
FIG. 21 is a rear view of the yoke of FIGS. 7 and 15-19.

As shown in FIG. 20, each end cap 606 includes a retention hole 605 on one side (e.g., in a rear side in the illustrated embodiment) and a retention notch 607 on an opposite side (e.g., a front side in the illustrated embodiment). In other embodiments, the position of the retention hole 605 and retention notch 607 can be reversed. The positioning of the retention hole 605 in the rear of the end cap 606 in the illustrated embodiment advantageously hides the retention hole 605 in use, which provides an improved aesthetic appearance. The retention notch 607 extends from the end cap cavity 609 forward into the end cap 606. The end cap inserts 618 include a first retention feature 616 on one of the front and back surfaces (e.g., extending rearwardly from the yoke back 604 portion of the end cap insert 618 in the illustrated embodiment) and a second retention feature 617 on an opposite surface (e.g., extending forward from the yoke front 602 portion of the end cap insert 618 in the illustrated embodiment). To attach the end cap 606 to the yoke 600, e.g., to the end cap insert 618, the retention hole 605 is engaged with the first retention feature 616 as shown in FIG. 15. The first retention feature 616 then acts as a hinge or pivot point, and the end cap 606 is pivoted over the end cap insert 618 in the direction indicated by the arrow in FIG. 15 until the second retention feature 617 and retention notch 607 engage, e.g., in a bump or snap fit connection. The hinged connection can provide a strong connection between the yoke 600 and end caps 606 with a reduced end cap insert 618 length L (indicated in FIG. 18). The end caps 606 can therefore taper more steeply. The reduced length of the end cap inserts 618, end caps 606, and/or overall yoke 600 can advantageously reduce or minimize the yoke 600 contacting or digging into the patient's face.

In the illustrated embodiment, the first retention feature 616 is or includes an oval or stadium shaped post extending rearward from the yoke back 604. The first retention feature 616 has a length or depth selected such that an outer or rearmost surface of the first retention feature 616 is flush or substantially flush with the rear surface of the yoke back 604. This increases the contact area and interaction between the end caps 606 and end cap inserts 618 and increases the retention forces. The connection between the end caps 606 and end cap inserts 618 can therefore resist greater torsional forces along the length of the yoke 600 and/or rotational forces about the joint.

In the illustrated embodiment, the second retention feature 617 is or includes a raised tab extending forward from the yoke front 602. The second retention feature 617 has a reduced length or depth compared to the first retention feature 616, which allows the end cap 606 to pass over the second retention feature 617 during assembly. In the illustrated embodiment, the second retention feature 617 has a chamfered lead-in 617a on one edge, e.g., on the lateral (relative to the yoke 600) edge in the illustrated embodiment, which allows the end cap 606 to be hinged or pivoted over and/or onto the second retention feature 617 more easily.

In some embodiments, the end caps 606 can be overmolded onto an end of a braided element of an automatic headgear adjustment mechanism, for example, braided elements as shown and described in U.S. Provisional Patent Application No. 62/343,711, entitled "Directional Lock for Interface Headgear Arrangement" and filed May 31, 2016, and PCT Application No. PCT/NZ2014/000074, the entireties of which are hereby incorporated by reference herein. The core elements or filaments 642 can extend within the braided elements. The end caps 606 can connect the braided element, and therefore the headgear, to the yoke 600 and create a closed loop headgear system.

As described herein, in some embodiments, the yoke 600 may form a collector or line track 630, 632 for core elements, such as filaments 642, used in an automatically adjustable or self-adjusting headgear system. In some configurations, the yoke 600 can provide a separate space (e.g., line track 630, 632) for each of the filaments 642. As shown in FIG. 10C, the yoke front 602 includes an upper line track 630 and a lower line track 632. A line track divider 634 protrudes rearwardly from a rear or internal surface of the yoke front 602. The line track divider 634 extends generally at a diagonal across a portion of the length of the yoke front 602 to transition from a relative upper location to a relative lower location relative to the yoke 600. In the illustrated embodiment, a divider wall 635 extends between each of the washer housings 646 and the opposing line track. The divider wall 635 separates the opposing line track from the washer housing 646 so that a free end of the filament 642 is inhibited from being caught in the opposing washer housing 646 during retraction. In the illustrated embodiment, the line tracks 630, 632 are not symmetrically mirrored due to the asymmetry of the upper and lower edges of the yoke 600.

FIG. 14 illustrates a variation of the yoke 600 in which the line tracks 630, 632 extend into and terminate within the end caps 606. The lengths of the line tracks 630, 632 are therefore extended beyond the ends of the yoke front 602 and yoke back 604. This increases the length of filament 642 that can be stored within the yoke 600, which increases the range of adjustment or variability in the size of the headgear.

The headgear assembly 200 defines a headgear loop that extends around a user's head in use. The filament 642 forms part of a headgear adjustment mechanism that allows a total length of the headgear loop to be extended during donning and doffing of the mask system. In some such embodiments, the length of each of the line tracks 630, 632 can be increased or extended by about 5 mm. In such embodiments, the total length of the headgear loop, in an extended state, can therefore increase by about 10 mm.

FIGS. 25A to 25D show an embodiment of a directional lock 1800 comprising a housing 1810, a first and a second lock element (e.g., washer 1820, 1822) and a core member or filament 1830. The housing 1810 comprises a first and a second chamber 1840, 1842 wherein the first and second chambers 1840, 1842 are configured to house the first and second lock washers 1820, 1822, respectively. Washers 1820 may be made out of a material that provides at least some resistance to wear from friction (e.g. polypropylene, high-density polyethylene, aluminum, steel). In the illustrated arrangement, the first and second chambers 1840, 1842 are separated by an internal wall 1812 of the housing 1810. However, in other arrangements, the first and second chambers 1840, 1842 are not necessarily physically separate spaces, but can, for example, be portions of a chamber. The housing 1810 has two end walls 1814, which along with the internal wall 1812, have an elongate core opening 1860 for the core member or filament 1830 to pass through. The core member or filament 1830 may be an elongate thread, fiber, string, wire, or filament, e.g. a nylon, polyethylene, polypropylene fiber, or a metal (e.g. aluminum, copper, silver) wire. Advantageously, a material may be chosen that provides at least some resistance to friction, fraying and splaying. Other shapes or geometries may be used, including a rectangular cross-section (e.g. a ribbon, band or belt) or multiple threads, fibers, strings, wires or filaments (e.g. a cable or braided or twisted wires). All of these may be referred to as the core member 1830. The material or materials of the core member may be chosen to be substantially non-elastic, thus allowing the core member 1830 to remain substantially the same length under elongative strain. The core openings 1860 may be substantially aligned with each other. The core opening 1860 of the end wall 1814 shown on the right side of the figures may be larger than one or both of the core opening 1860 of the internal wall 1812 and the end wall 1814 shown on the left of the figures. This allows for manipulation or deflection of the path of the core member 1830 through the housing 1810. The first and second chambers 1840, 1842 are each delimited by the internal wall 1812, one of the end walls 1814 and a pair of side walls 1816; wherein the side walls 1816 extend between the end walls 1814 of the housing 1810. The first and second chambers 1840, 1842 are configured to be open at one or both of a top and a bottom of the housing 1810.

Each of the first and second chambers 1840, 1842 has a pair of washer retainers 1850 that are aligned on opposing side walls 1816 of the housing 1810. Each pair of washer retainers 1850 is configured to pivotally retain one of the first or second lock washers 1820, 1822 within the respective first or second chamber 1840, 1842. The washer retainers comprise a circular bush 1852 and an elongate slot 1854, wherein circular bushes 1852 intersect with the bottom of the housing such that an entrance is formed. The entrance is configured to allow the first and/or second lock washers 1820, 1822 to be received into the washer retainers 1850. The slot 1854 extends radially from the circular bush 1852 towards the top of the housing 1810.

The first and second washers 1820, 1822 each comprise a cylindrical shaft 1824 and an arm 1826 that extends from their respective shaft 1824. The cylindrical shaft 1824 is substantially the same width W, as the housing 1810 and the arm 1826 is narrower to fit within the first and second chambers 1840, 1842. In the illustrated arrangement, the arm 1826 comprises a first section 1872 and a second section 1874, wherein the first section 1872 extends radially or perpendicularly from the cylindrical shaft 1824 and the second section 1874 extends at an obtuse angle from the end of the first section 1872. The first section 1872 of the arm 1826 of the first washer 1820 is shorter than the first section 1872 of the arm 1826 of the second washer 1822. The angle between the first and second sections 1872, 1874 of the arm 1826 of the first washer 1820 is greater than the corresponding angle of the second washer 1822. The angles can be selected such that the second section 1874 of one or both of the first and second washers 1820, 1822 lies substantially flat against the corresponding wall (e.g., internal wall 1812 and end wall 1814, respectively) of the housing 1810 in one position of the washers 1820, 1822. The second section 1874 of the arm 1826 comprises a centrally located circular aperture 1876 configured to receive the core member 1830. The first and second chambers 1840, 1842 differ in size according to the size of the washer that is to be housed within it, i.e. the first chamber 1840 is smaller than the second chamber 1842 because the first washer 1820 is smaller than the second washer 1822.

The cylindrical shafts 1824 of the first and second lock washers 1820, 1822 have a diameter substantially the same as that of the circular bushes 1852 of the washer retainer 1850, and are configured to be received and retained by the circular bush 1852 in a snap-fit configuration. The snap-fit configuration is provided by the entrance of the circular bush 1852 being narrower than the diameter of the cylindrical shaft 1824. The slots 1854 of the washer retainers 1850 are configured to allow the entrance to be flexed open to increase the ease with which the first and second lock washers 1820, 1822 can be pushed through the entrances and assembled to the housing 1810. Once assembled within the first and second chambers 1840, 1842 of the housing 1810, the first and second washers 1820, 1822 can pivot back and forward around a central axis that runs through the cylindrical shaft 1824.

Figure 25A:
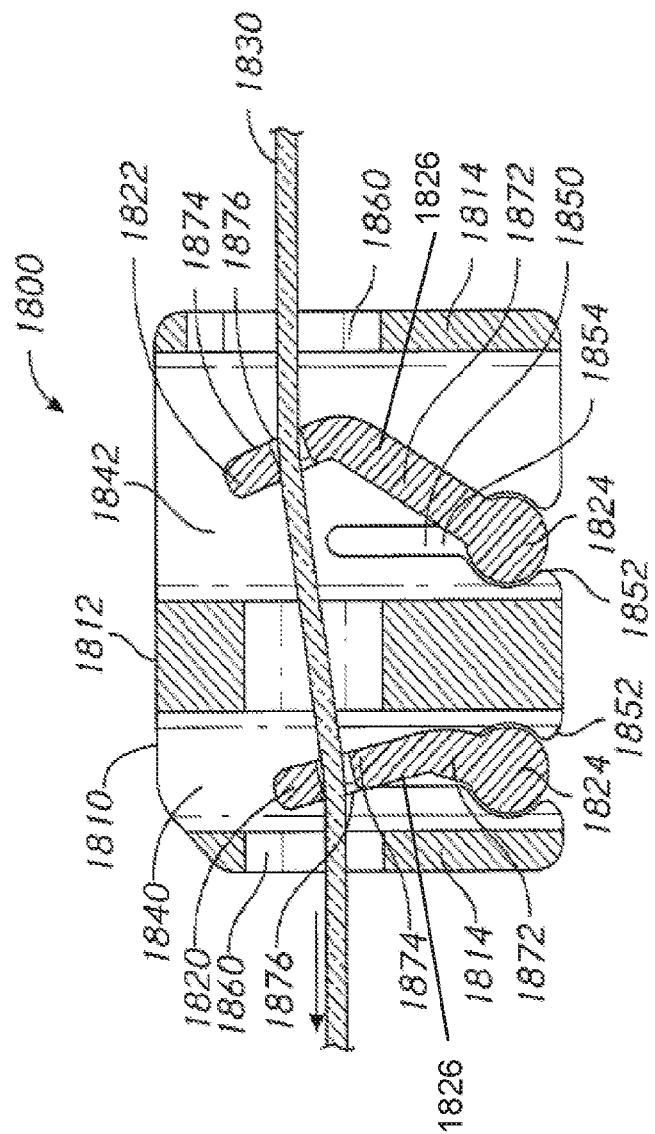
FIG. 25A is a cross-sectional view of a directional lock in a locked position.
Figure 25B:
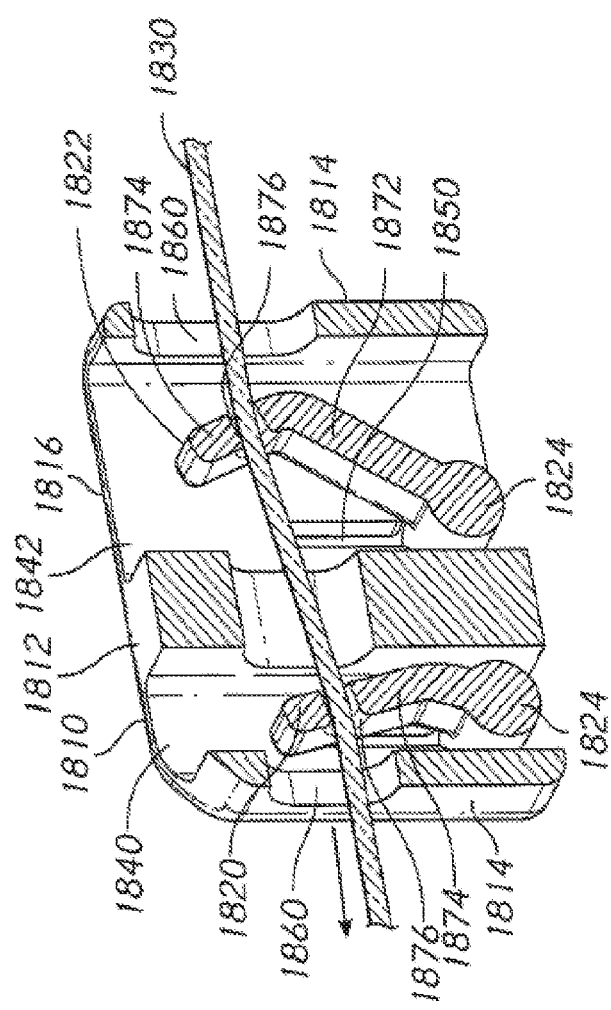
FIG. 25B is a perspective cross-sectional of the directional lock in FIG. 25A in the locked position.
Figure 25C:
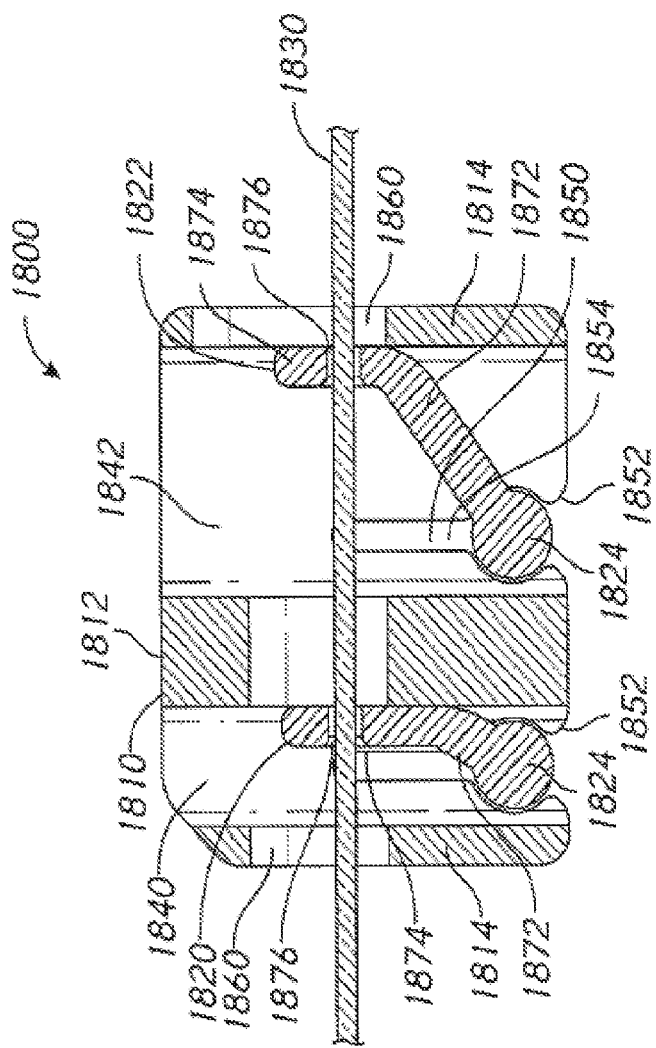
FIG. 25C is a cross-sectional view of the directional lock in FIG. 25A in the unlocked position.
Figure 25D:
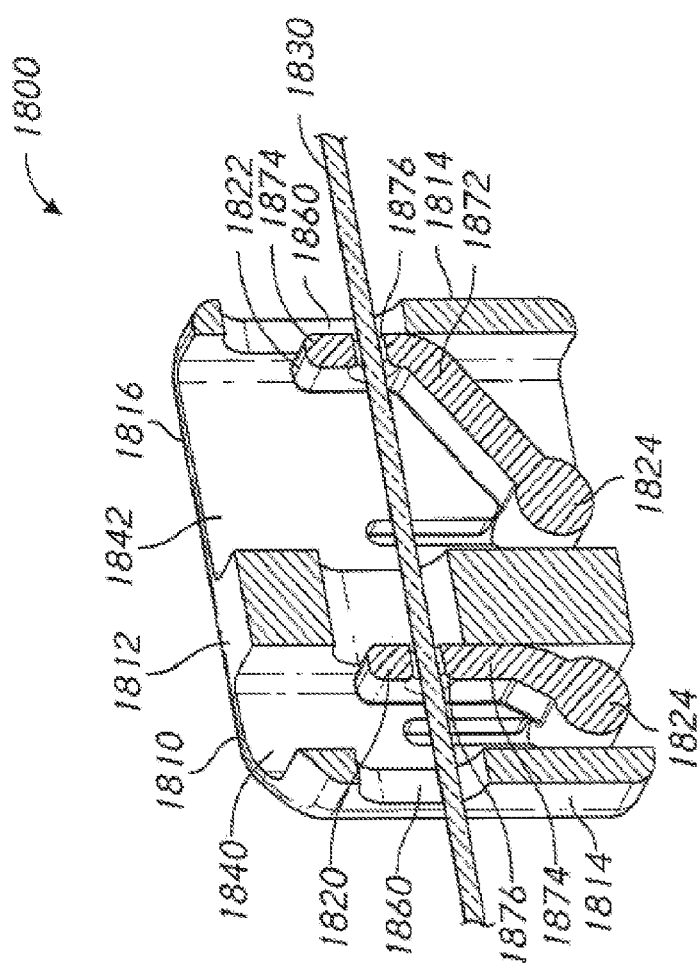
FIG. 25D is a perspective cross-sectional of the directional lock in FIG. 25A in the unlocked position.
Figure 26:
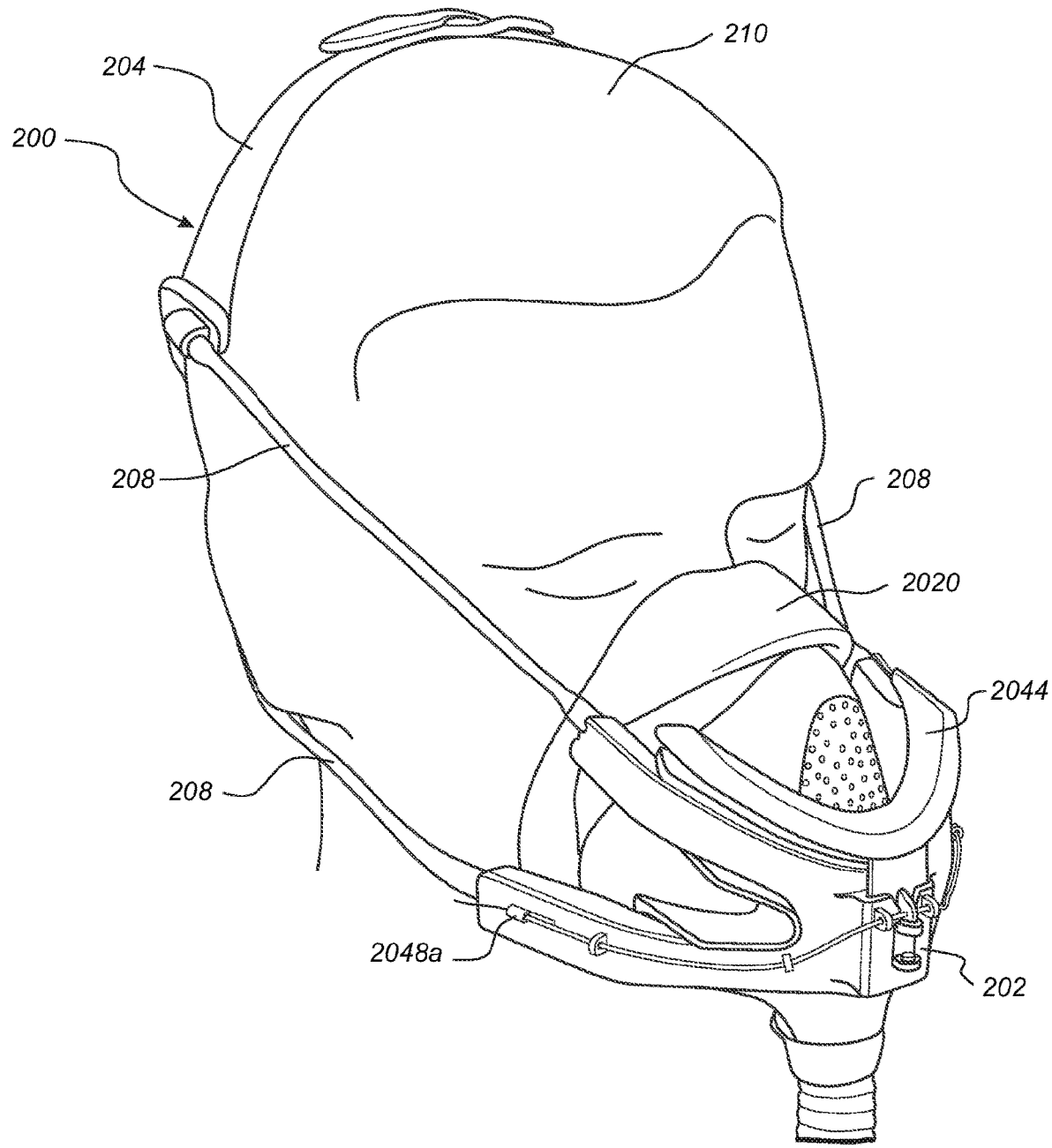
FIG. 26 is a perspective view of a mask assembly, including a headgear assembly, a seal assembly, and a frame assembly.
Figure 27:
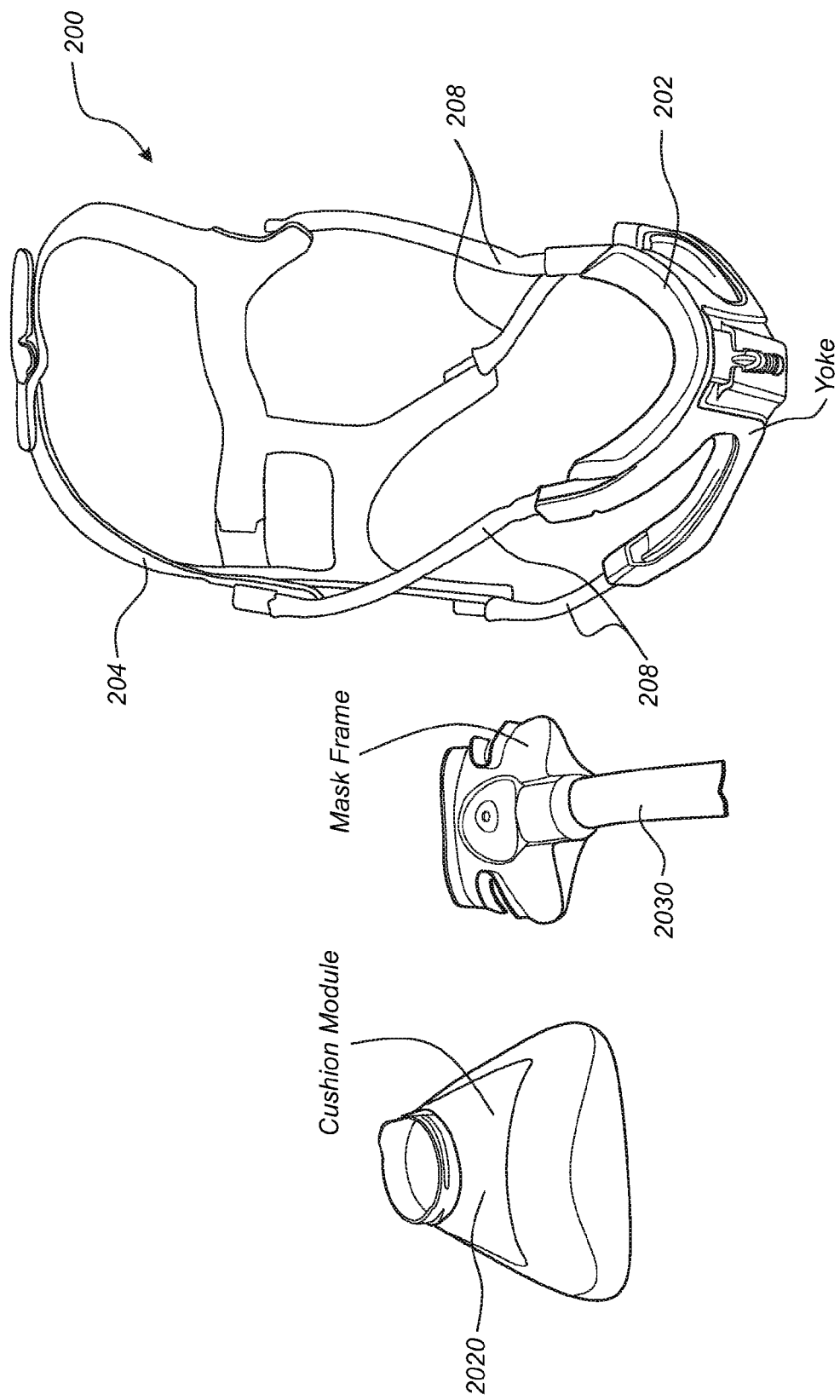
FIG. 27 is a perspective view of the cushion module, mask frame and yoke of FIG. 26 disconnected from each other.
Figure 28:
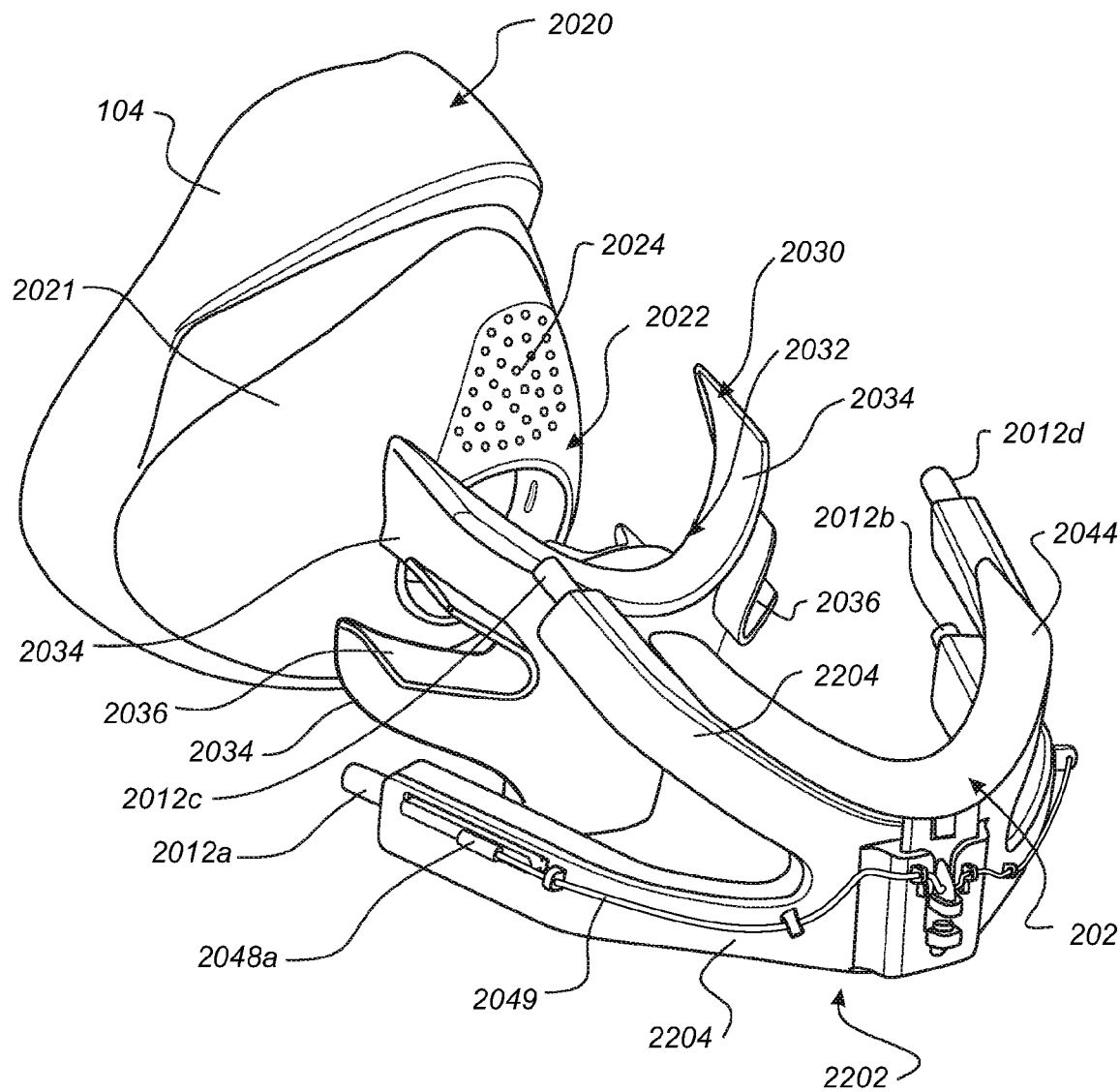
FIG. 28 is an exploded view of the cushion module, mask frame and yoke.
Figure 29:
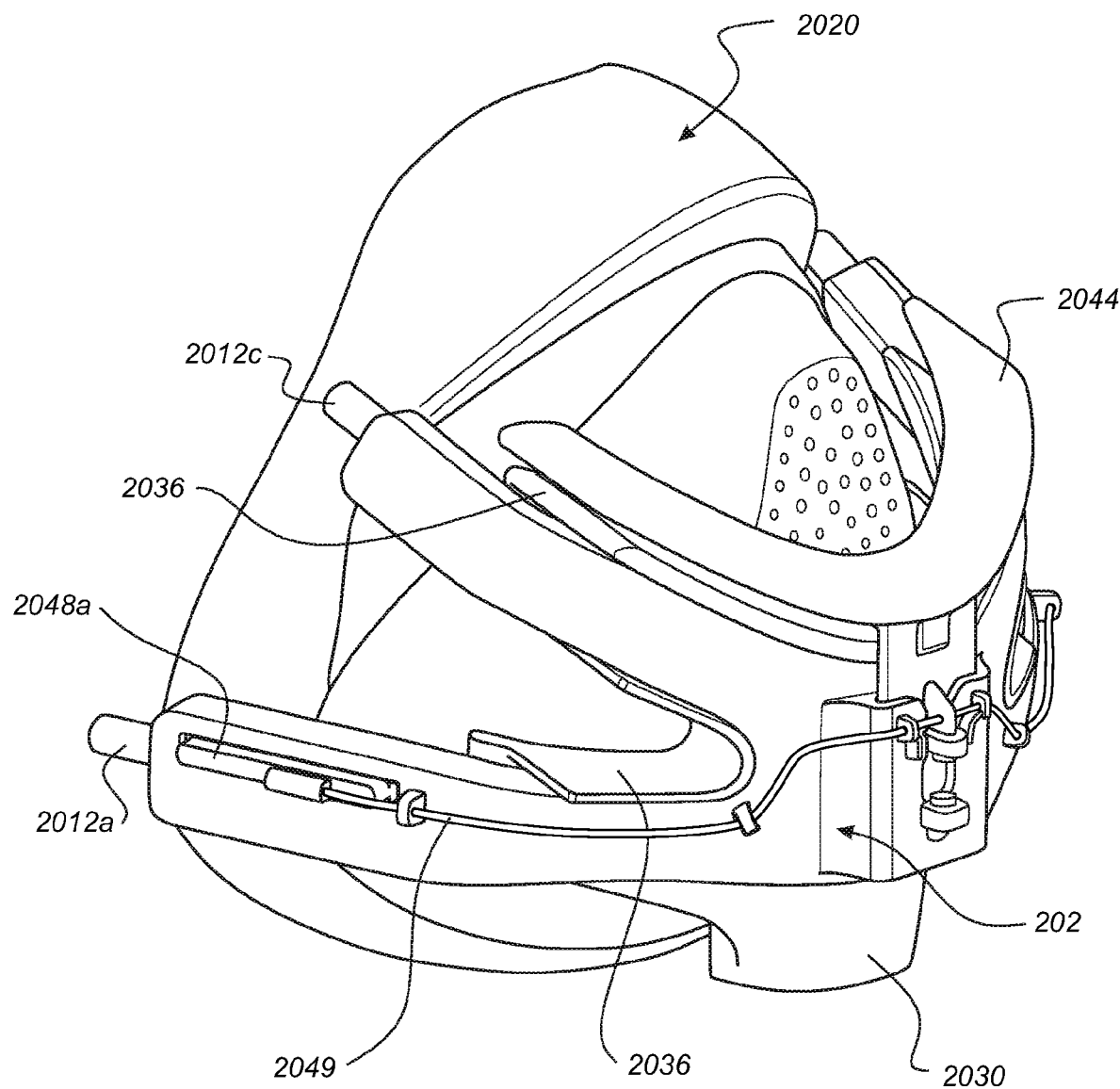
FIGS. 29, 30 and 31 are perspective, front and side views, respectively, of the assembled cushion module, mask frame and yoke of FIG. 26.
Figure 30:
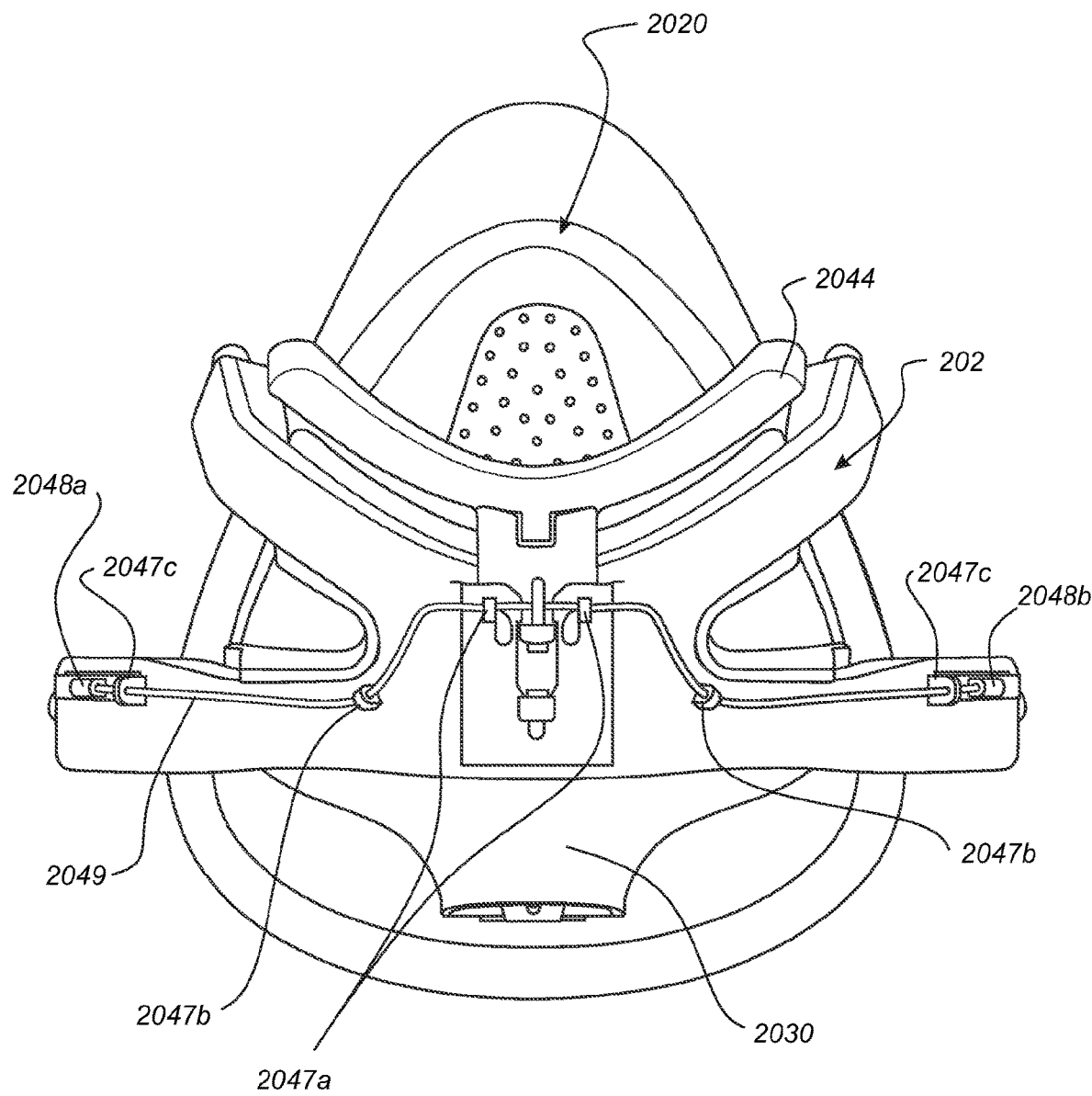

The core member 1830 may be configured to pass through the core openings 1860 of the housing 1810 and the apertures 1876 of the first and second washers 1820, 1822. Application of a tension force to the core member 1830 causes the first and second lock washers 1820, 1822 to pivot back and/or forward between a locked position and/or open position. FIGS. 25A and 25B show the directional lock in a locked configuration in which a force is applied to the core member 1830 in a direction towards the left side of the figure (as indicated by the arrow). In an embodiment, the force applied to the core member 1830 in this configuration causes the first and second lock washers 1820, 1822 to pivot in an anti-clockwise direction, such that the path of the core member 1830 through the directional lock 1800 is non-linear or tortuous and/or an increased frictional force is applied to resist movement of the core member 1830, e.g. due to an increase of the area in contact between core member 1830 and first and second lock washers 1820, 1822 and an increase in contact pressure. FIGS. 25C and 25D show the directional lock in an open or unlocked configuration in which a force is applied to the core member 1830 in a direction towards the right side of the figure (as indicated by the arrow). In this configuration, the first and second lock washers 1820, 1822 may be pivoted in a clockwise direction such that the circular apertures 1876 and core openings 1860 are aligned in a substantially straight line. This provides a smooth and low-friction path and/or reduced contact pressure for the core member 1830 to be pulled substantially freely through the directional lock 1800. Based on the different amount of frictional force exerted on core member 1830 in the closed position and the open position, the amount of force required to move core member 1830 through the directional lock 1800 may be varied.

While the illustrated embodiment of directional lock 1800 utilizes first and second lock washers 1820, 1822, fewer or more lock washers could be used. The number of lock washers, the type, length and thickness of core member 1830, and the geometry of lock washers 1820 are design parameters that can be varied to determine an amount of force necessary to overcome directional lock 1800 while in the closed configuration ("yield force") and an amount of force necessary to open the lock while in the open configuration ("opening force").

Additional particulars of the operation of the directional locks 1800 are described above and in Applicant's patent application No. PCT/NZ2014/000074, the entire contents of which are hereby incorporated by reference.

With reference to FIGS. 26-43, several arrangements for securing a respiratory interface, such as a respiratory mask, to the head of a wearer and to facilitate convenient removal of the interface are described in further detail. In FIGS. 26-43, the respiratory interface is a full-face mask having an upper headgear strap and a lower headgear strap on each side of the user's head that connect the mask to a rear portion of a headgear. One or more directional locks can be incorporated into the mask, headgear or other portion of the interface assembly that are configured to provide a locking or retention force tending to inhibit or prevent elongation of the interface assembly and to permit retraction of the interface assembly against a resistance that is less (e.g., significantly less) than the locking or retention force. Preferably, the directional lock(s) are configured to provide very little or substantially no resistance to retraction of the interface assembly. In the illustrated arrangements, the interface assembly incorporates a release mechanism or arrangement that permits a user to manually release the directional lock(s) to facilitate elongation of the interface assembly. Although the illustrated release mechanisms or arrangements are applied to a full-face mask having upper and lower headgear straps, the release mechanisms or arrangements can be used with, or can be modified for use with, other types of masks and headgear arrangements, such as the nasal masks and two-strap headgear arrangements of FIGS. 1-24, among others.

FIGS. 26-34 illustrate a mask assembly that may comprise a cushion module 2020, a mask frame 2030 and a headgear arrangement 200, which in the illustrated arrangement includes a yoke 202. FIGS. 28-34 illustrate various views of the mask assembly with the straps 208 and rear portion 204 of the headgear 200 omitted. The yoke 202 may be attached to a rear portion 204 of the headgear 200 via one or more upper straps 208 and/or one or more lower straps 208. In the illustrated arrangement, the headgear 200 includes an upper strap 208 and a lower strap 208 on each side of the mask assembly. Advantageously, upper straps 208 and/or lower straps 208 may be coupled to yoke 202 using one or more manually releasable or disengageable locks, such as disengageable locks 2048a, 2048b. An actuator, or disengagement element 2044, may be linked to the one or more disengageable locks 2048a, 2048b to allow for manual release or disengagement of the locks 2048a, 2048b. Headgear attachment posts, including lower headgear attachment posts 2012a, 2012b and upper headgear attachment posts 2012c, 2012d, may be provided to connect the straps 208 of the headgear 200 to the yoke 202. The yoke 202, the mask frame 2030 and the cushion module 2020 may be distinct components that can be taken apart and reassembled. In other configurations, any combination of the yoke 202, the mask frame 2030 and the cushion module 2020 can be integrated with one another. Thus, although yoke 202 is described as forming a portion of the headgear 200 herein, in other configurations the yoke 202 can be integrated with or formed as a portion of the mask frame 2030 or the cushion module 2020.

In general, the mask assembly of FIGS. 26-34 is similar in construction to the mask assemblies of FIGS. 1-24, except that the mask assembly of FIGS. 26-34 is implemented in a full-face form rather than the nasal masks of FIGS. 1-24. The mask assembly of FIGS. 26-34 includes the frame 2030 that is configured for connection with the cushion module 2020 and the yoke 202. The frame 2030 is configured to connect with a gas conduit (not shown) to deliver a flow of breathing gases to the user via the cushion module 2020. The illustrated frame 2030 has a central portion 2032, which defines an interior passage configured to communicate the flow of breathing gases from the gas conduit to the cushion module 2020. The central portion 2032 of the frame 2030 and/or the interior passage extends in a vertical direction and overlies a central portion 2022 of the cushion module 2020 when the mask assembly is viewed from the front. A plurality of arms 2034 sweeps in a rearward direction from the central portion 2032 of the frame 2030 and approximately follows the shape of the cushion module 2020. In the illustrated arrangement, the frame 2030 has four arms 2034, which includes an upper right arm, an upper left arm, a lower right arm and a lower left arm. The upper arms 2034 and the lower arms 2034 can diverge from one another in a front-to-back direction. The illustrated upper arms 2034 extend in an upward direction away from the lower arms 2034 in a front-to-back direction. The lower arms 2034 can have a generally or substantially horizontal orientation. Such an arrangement can accommodate a vent 2024 of the cushion module 2020 and/or orient the headgear straps 208 in a desirable direction to comfortably achieve a satisfactory seal.

The cushion module 2020 can include a relatively rigid housing 2021 and a relatively soft cushion or seal 104. In the illustrated arrangement, the housing 2021 maintains a desired shape of the cushion module 2020, allows for connection to the frame 2030 and defines at least a portion of a breathing chamber of the cushion module 2020. The cushion or seal 104 is removably or permanently coupled to the housing 2021 and is configured to create a seal against the user's face to seal the breathing chamber. In the illustrated arrangement, the housing 2021 also includes the exhaust vent 2024, which permits venting of expired gases from the breathing chamber and provides a restricted leak path configured to maintain a positive pressure within the breathing chamber. The exhaust vent 2024 is located above the inlet opening. The exhaust vent comprises a plurality of vent holes through the housing 2021. In other arrangements, the exhaust vent 2024 could be located elsewhere, such as within the frame 2030, for example.

The yoke 202 is configured to be removably coupled to the frame 2030, such that the headgear 200 can be coupled to the cushion module 2020 via the frame 2030. The yoke 202 has a shape that is similar to the shape of the frame 2030 when viewed from the front. The yoke 202 includes a central portion 2202 that overlies a portion or an entirety of the central portion 2032 of the frame 2030. The yoke 202 also includes a plurality of arms 2204 that sweeps in a rearward direction from the central portion 2202. In some configurations, the number of arms 2204 of the yoke 202 is equal to the number of arms 2034 of the frame 2030. In the illustrated arrangement, the yoke 202 includes left and right upper arms 2204 and left and right lower arms 2204 that correspond with a respective one of the upper and lower arms 2034 of the frame 2030. In some configurations, the arms 2204 of the yoke 202 are longer than the corresponding arms 2034 of the frame 2030 and, therefore, extend in a rearward direction beyond the ends of the corresponding arms 2034 of the frame 2030. The arms 2204 of the yoke 202 can extend beyond the housing 2021 of the cushion module 2020 such that ends of the arms 2204 are located adjacent or rearward of the seal 104.

The frame 2030 can include one or more walls or lips 2036 extending outwardly from a forward surface of the arm(s) 2034 and adjacent to the arms 2204 of the yoke 202. The walls 2036 can be configured to couple the yoke 202 to the frame 2030, such as with a snap-fit arrangement, or can serve to inhibit or prevent rotation of the yoke 202 relative to the frame 2030 about one or more axes. In the illustrated arrangement, a single wall 2036 extends along the central portion 2032 and upper arms 2034 and additional single walls 2036 extend between each of the upper and lower arms 2034 on each of the left and right sides of the frame 2030.

The yoke 202 may comprise a front piece 2042 and a rear piece 2046 that are removably or permanently coupled to one another in a manner similar to yokes 202 and 600 described with respect to FIGS. 1-24. The yoke 202 can define an interior space configured to receive excess portions of core member(s) or filament(s) (e.g., filaments 642, 1830) utilized by the directional lock(s) 2048a, 2048b. Although not illustrated, the yoke 202 can divide the interior space into separate sections for each of the filaments.

As described above, the yoke 202 or other portion of the mask assembly of FIGS. 26-34 can include or support one or more actuators or disengagement elements 2044. The disengagement element 2044 may be configured to release, unlock or open one or more disengageable locks, such as disengageable locks 2048a, 2048b. In the illustrated arrangement, actuation of the disengagement element 2044 prevents the directional locks from moving to a locked position in response to elongation of the headgear 200 or overall mask assembly. Thus, the disengagement element 2044 allows for deliberate or manual deactivation of the directional locks. In other words, the normal operation of the directional locks (e.g., moving to a locked position in response to elongation of the headgear 200) is temporarily suspended while the disengagement element 2044 is actuated. However, the disengagement element 2044 is contemplated for use with other types of headgear locking arrangements. When used with other types of locks, the disengagement element 2044 may be configured to physically move the lock to a released position upon actuation to facilitate elongation of the headgear 200 or overall mask assembly. The specific operation of the disengagement element 2044 can be configured for the specific locks utilized so as to achieve the aim of permitting manual or deliberate release of the lock(s) to permit elongation of the headgear 200 or overall mask assembly with reduced effort.

Figure 33:
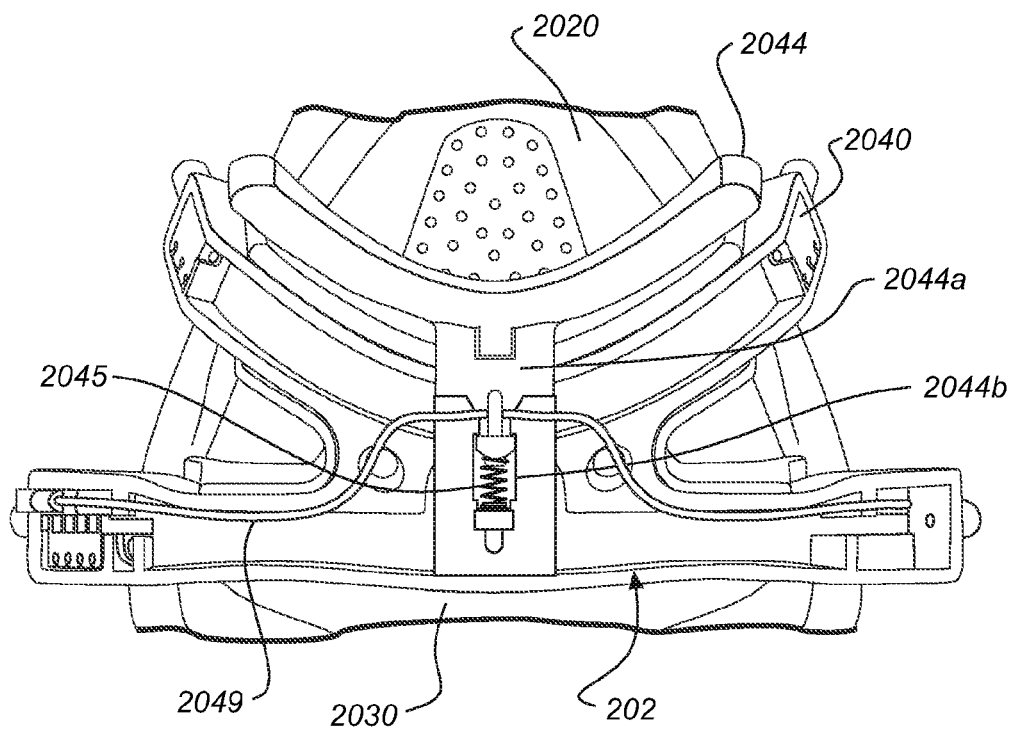
Figure 34:
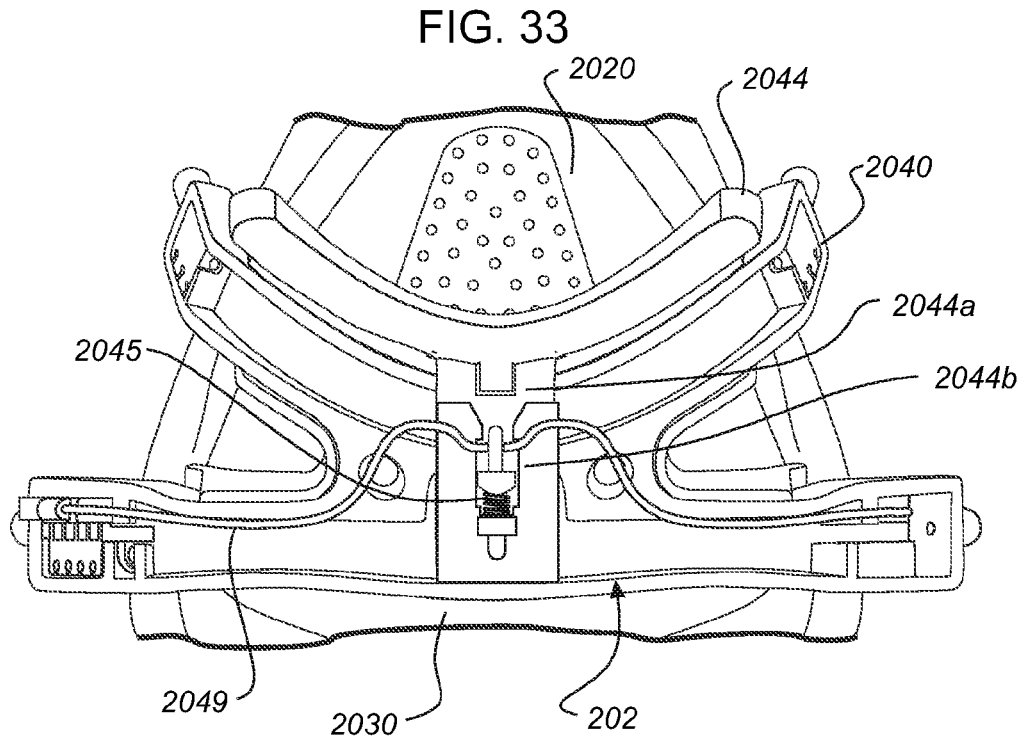
Figure 35:
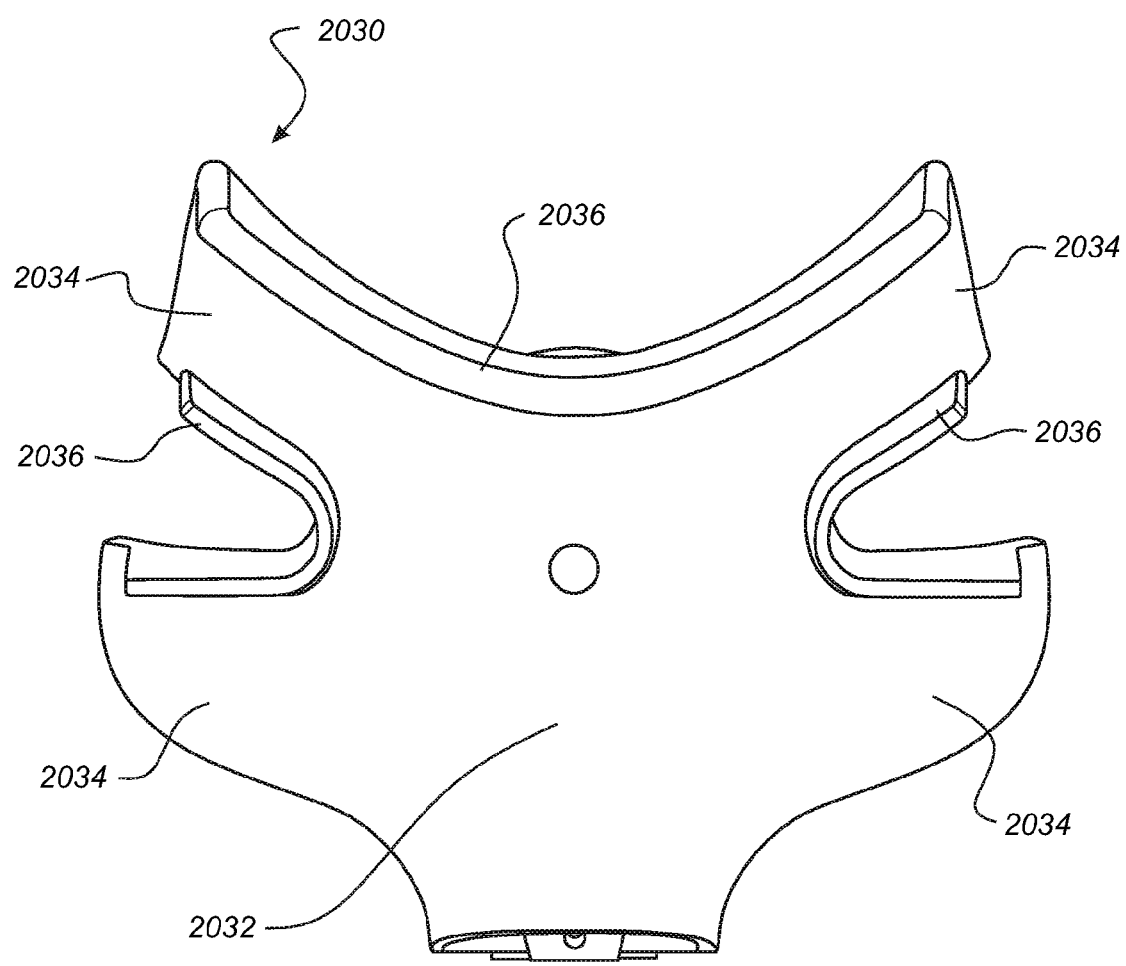
FIGS. 35, 36 and 37 are front, side and rear views, respectively, of the frame of FIG. 26.
Figure 36:
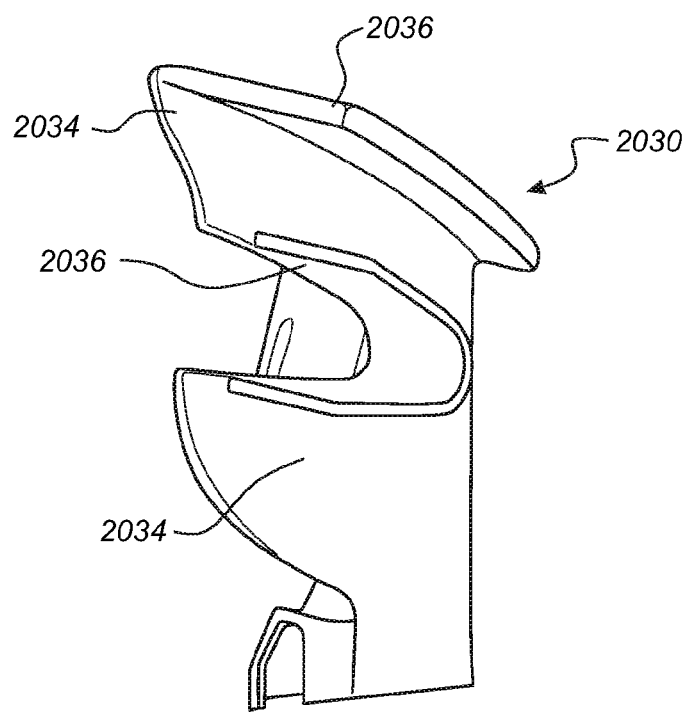
Figure 37:
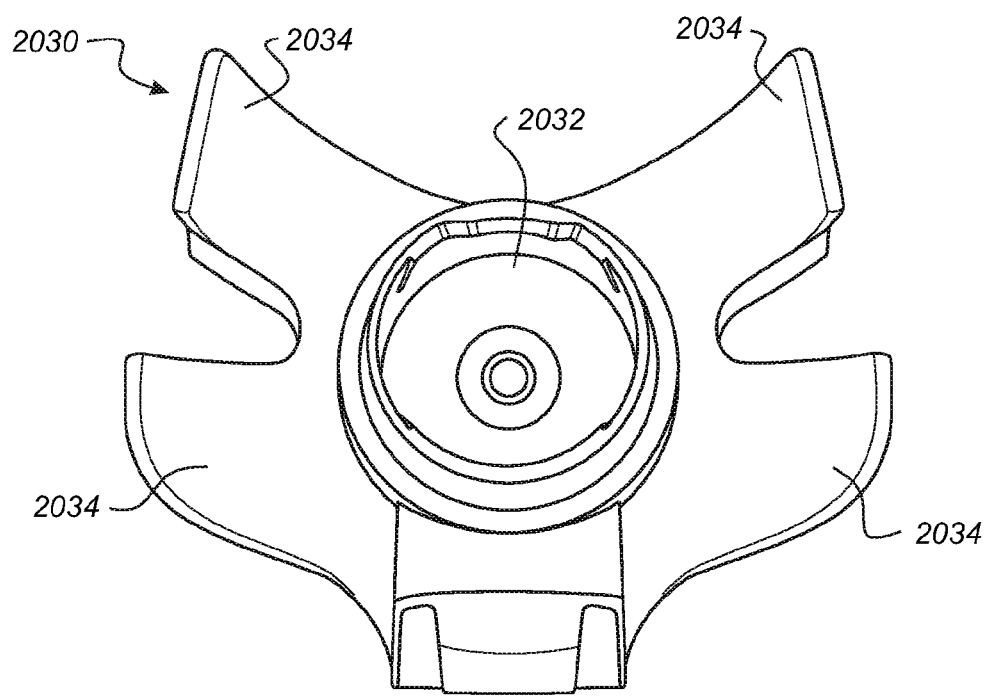
Figure 38:
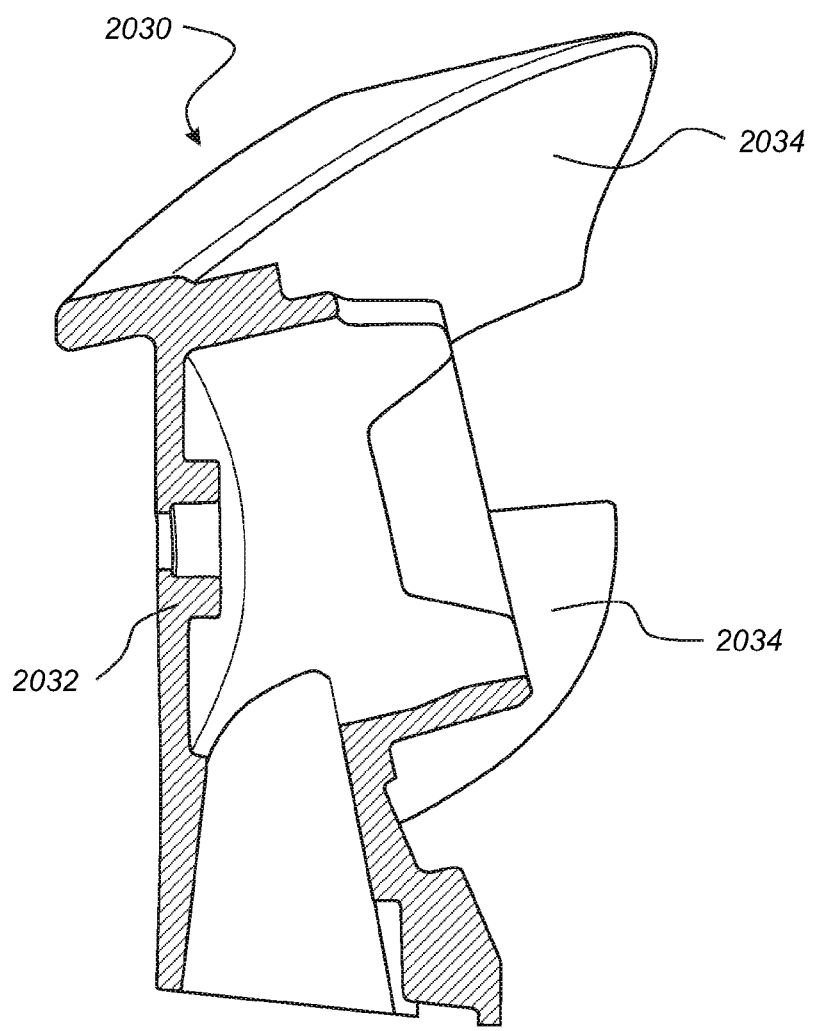
FIG. 38 is a cross-section view of the frame of FIG. 26.
Figure 39:
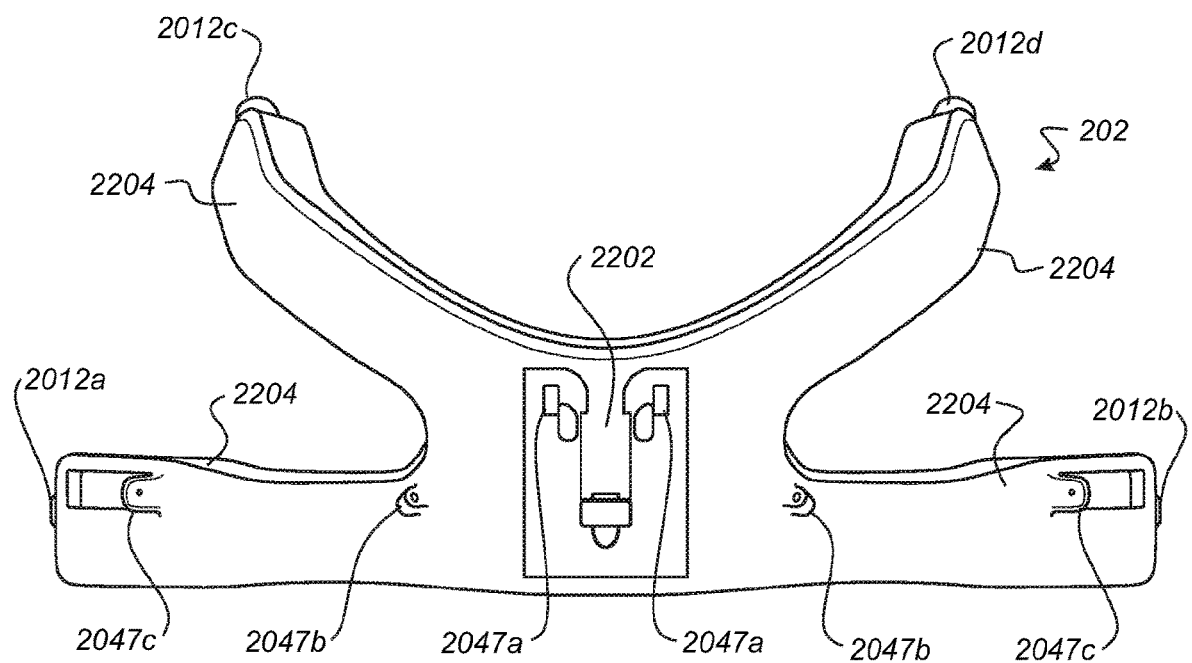
FIGS. 39, 40 and 41 are front, rear and side views, respectively, of the yoke of FIG. 26.
Figure 40:
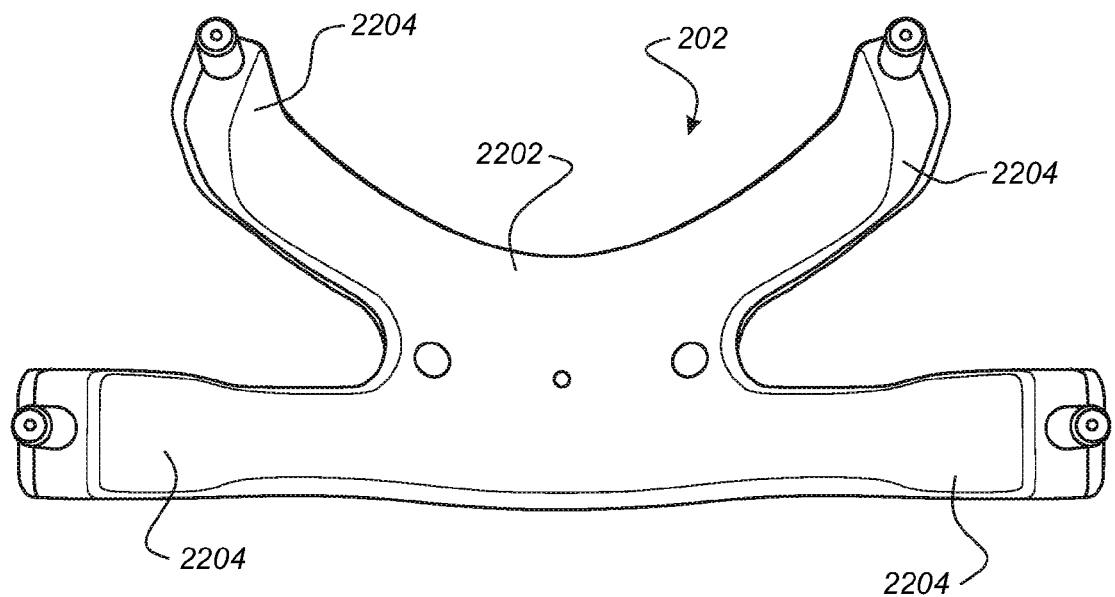
Figure 41:
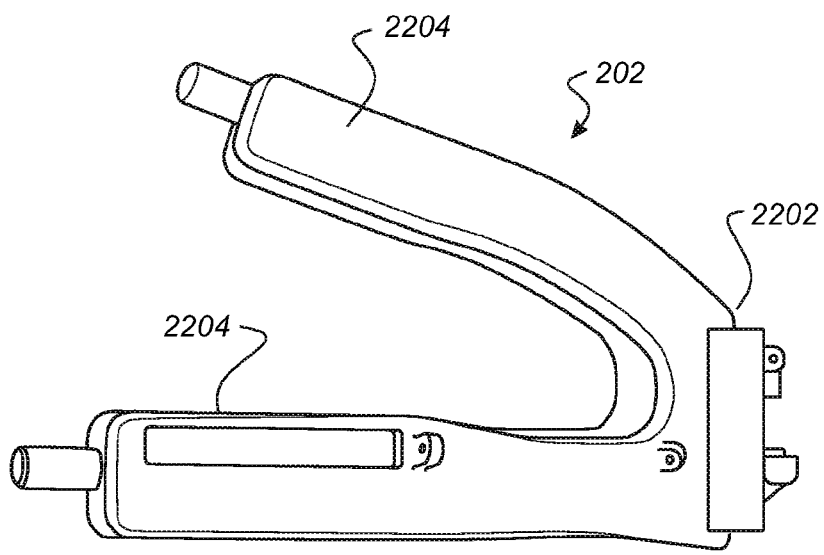
Figure 42:
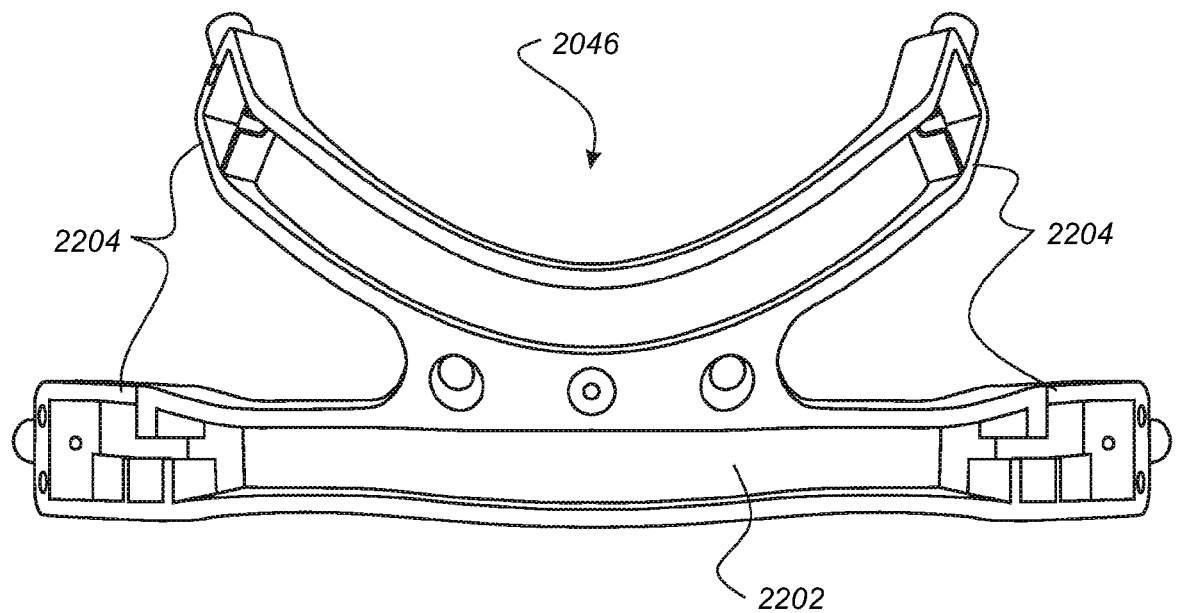
FIGS. 42 and 43 are partial cross-section views of the yoke of FIG. 26.
Figure 43:
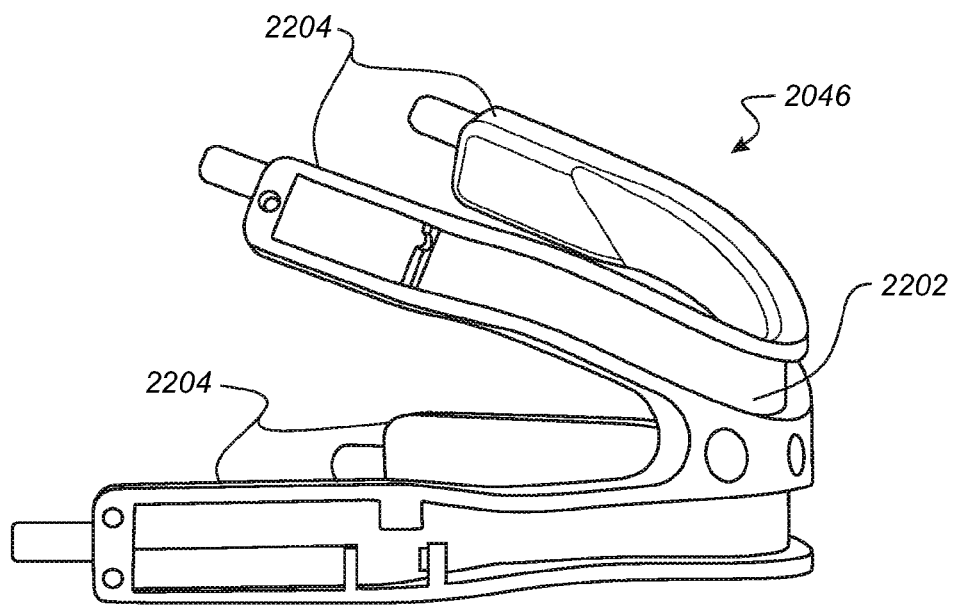

The disengagement element 2044 may be provided in different forms or shapes (e.g. a button, lever or handle) and be provided on different locations of the yoke 202 or another portion of the mask assembly. Advantageously, in one arrangement the disengagement element 2044 is located at least partially on a front side of the yoke 202 or mask and/or at least partially on a top side of the yoke or mask so that a user gripping the mask can naturally or intuitively exert a force onto the disengagement element 2044 (e.g. by squeezing or pinching the disengagement element 2044 toward the yoke 202) in the process of donning or doffing the mask assembly. FIG. 33 and FIG. 34 illustrate the disengagement element 2044 in a released position and an actuated position, respectively.

In the illustrated arrangement, the disengagement element 2044 is in the form of an elongate button or bar that extends along and is spaced-apart from an upper edge of the yoke 202. The disengagement element 2044 can be curved in a manner similar to the yoke 202 such that the lateral ends of the disengagement element 2044 are positioned rearwardly of the center portion. Such an arrangement can provide an attractive appearance as well as provide access to the disengagement element 2044 from the center and the sides of the mask assembly. In other arrangements, the disengagement element 2044 can be positioned along a lower edge of the yoke 202.

Other arrangements are possible in which the disengagement element(s) 2044 is positioned relative to the yoke 202 such that a user can actuate the disengagement element(s) 2044 in the process of grasping the yoke 202 or mask, thus intuitively triggering the release of the one or more disengageable locks (e.g., disengageable lock 2048a, 2048b). For example, a pair of opposed disengagement elements 2044 could be positioned such that a user could squeeze the elements 2044 towards one another (e.g., in a horizontal, vertical or other direction relative to the orientation shown in the figures). In such an arrangement, each disengagement element 2044 could operate one or more disengageable locks (e.g., 2048, 2048b).

Figure 32:
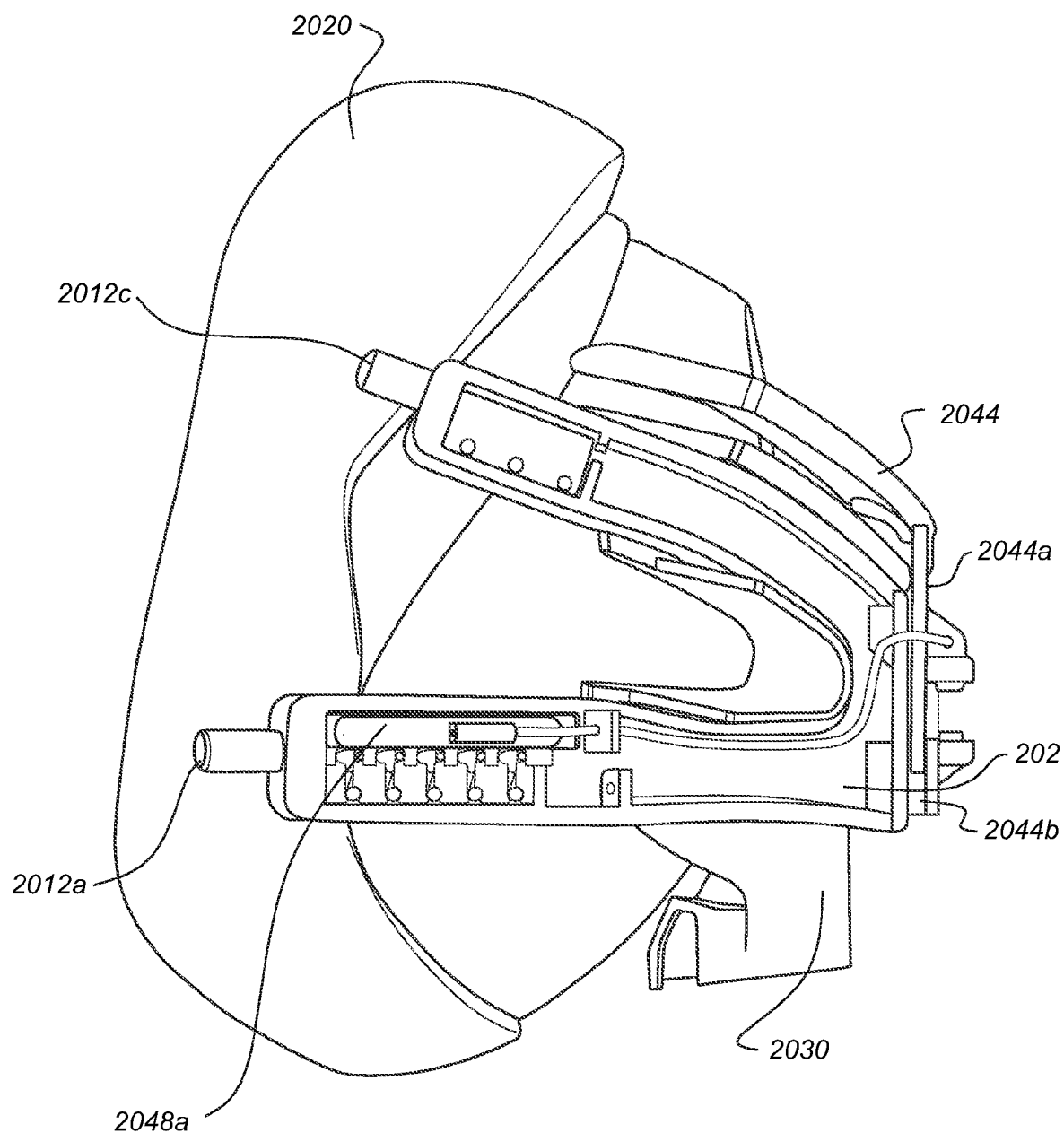
FIGS. 32, 33 and 34 are partial cross-section views the assembled cushion module, mask frame and yoke of FIG. 26.

In the illustrated arrangement, the disengagement element 2044 is coupled to the yoke 202 in a manner that restricts or guides the relative movement of the disengagement element 2044. In particular, the disengagement element 2044 includes a first guide element 2044a and the yoke 202 includes a second guide element 2044b (FIG. 32). The first guide element 2044a is captured for sliding movement within the second guide element 2044b, or vice-versa, to at least substantially restrict movement of the disengagement element 2044 to translation relative to the yoke 202. However, in other arrangements other types of movement may be permitted, such as rotational movement, for example. In the illustrated arrangement, the first guide element 2044a is an elongate, flat plate or bar and the second guide element 2044b is a partially or fully-enclosed slot having a shape that corresponds to the shape of the first guide element 2044a. However, these arrangements could be reversed. The slot can be defined by the yoke 202 or by a separate structure attached to the yoke 202. The illustrated arrangement advantageously permits movement of the disengagement element 2044 toward and away from the upper edge of the yoke 202, but inhibits or substantially prevents relative movement in other directions, to provide for smooth and/or consistent actuation of the disengagement element 2044.

Figure 31:
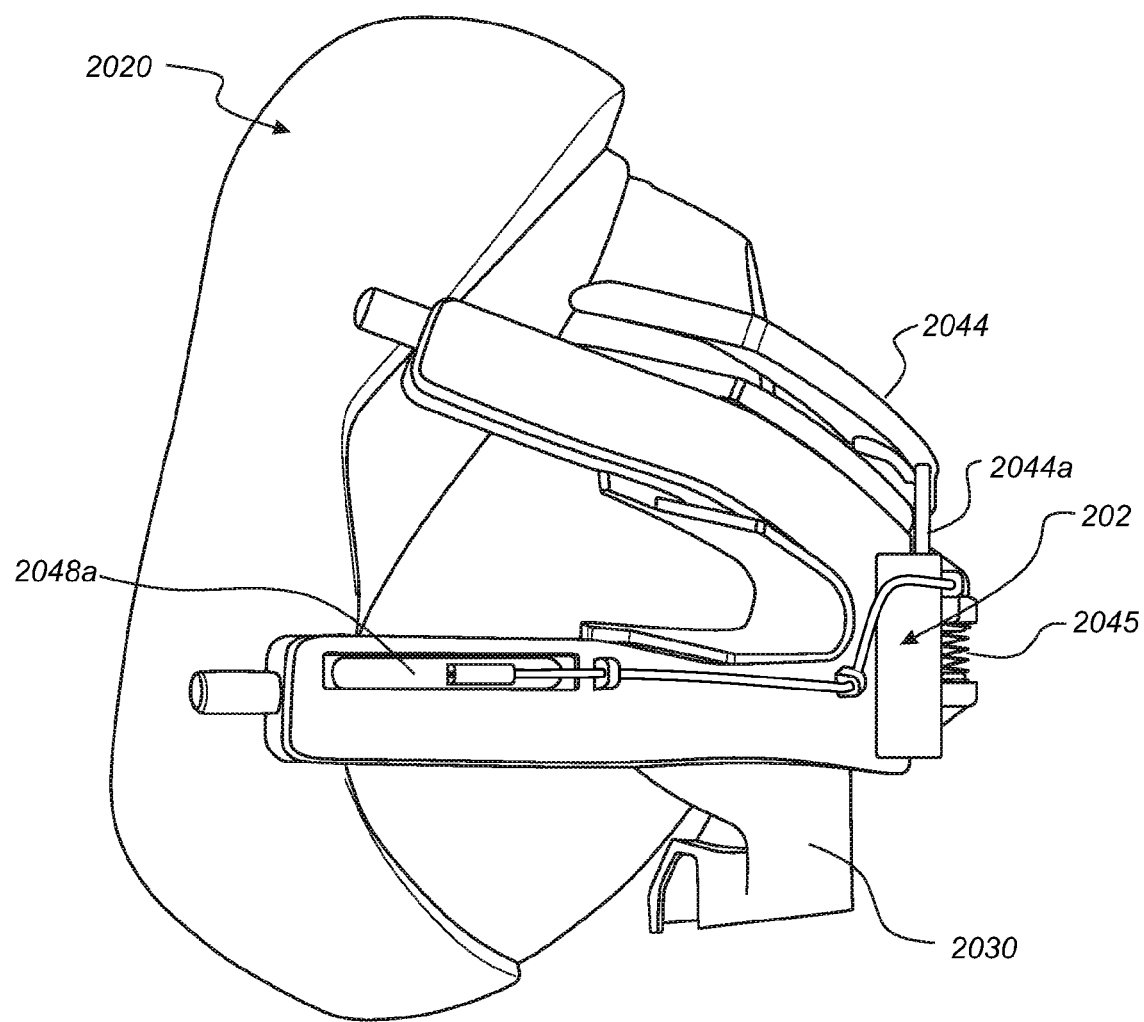

In some arrangements, a biasing element, such as a spring or other elastic element 2045 may be included, e.g. between the disengaging element 2044 and the yoke 202 and configured to bias the disengaging element 2044 toward or to the unactuated position in which the disengageable locks 2048a, 2048b are locked or permitted to move to a locked or engaged position. In the illustrated arrangement, a portion of the disengagement element 2044 protrudes from the slot (second guide element 2044b) through an access opening in the yoke 202 and forms a structure that engages one end of a biasing element 2045 (FIG. 31). The yoke 202 includes a structure that engages the other end of the biasing element 2045.

The number of disengageable locks utilized in a given mask assembly may be varied based on a variety of relevant factors, such as the type of mask or interface, the number of headgear straps connected to the mask, and the desired doffing and donning procedure, among other possibilities. In the illustrated arrangement, each of the lower straps 208 of the headgear 200 features a disengageable lock 2048a, 2048b, whereas the upper straps 208 do not include a disengageable lock. However, in the illustrated arrangement, the upper straps 208 include directional locks (as described below) that work in a manner that is similar to or the same as the directional locks 1800 described with reference to FIGS. 1-25. In a full-face mask, the lower straps of the headgear often require greater extension than the upper straps of the headgear for comfortable donning or doffing of the full-face mask. Thus, in some configurations, only the lower headgear straps may be provided with manually or deliberately disengageable locks. In addition, the tension in the lower straps during operation tends to be larger than the tension in the upper straps. Thus, in arrangements that incorporate directional locks (or other automatic locks), the locking force of the locks in the lower straps may be greater than a locking force of the upper straps. Thus, it can be more beneficial to provide for manual or deliberate release of the locks in the lower straps, which have a higher locking force and, thus, a greater resist to elongation than the locks of the upper straps. Providing for manual or deliberate release in only a portion of the straps (e.g., the lower straps) can reduce complexity of the system and lower the overall cost compared to arrangements in which each strap is provided with a disengageable lock. However, if desired, disengageable locks can be provided in any of the straps or portions of the headgear. Thus, in some configurations, the upper straps 208 may be attached with a disengageable lock on one or both sides. In addition, in some configurations, the lower straps 208 may be attached without a disengageable lock. As discussed, in some configurations, all of the upper and lower straps 208 may be attached using disengageable locks. Furthermore, in some configurations disengageable locks may be provided in the rear, top, or side of the headgear to enable elongation of various headgear sections during donning and doffing.

The one or more disengageable locks 2048a, 2048b may be connected to the disengagement element 2044 either directly or via an actuation arrangement configured to transfer motion from the disengagement element 2044 to the disengageable locks 2048a, 2048b. The actuation arrangement can be referred to herein as a linking member 2049. In some configurations, the linking member 2049 can be a substantially non-elastic string, cable or wire that is tensioned by a movement of disengagement element 2044, thereby capable of transmitting force from disengagement element 2044 to the one or more disengageable locks 2048a, 2048b. In some configurations, the linking member 2049 may be or include a Bowden cable or an arrangement similar to a Bowden cable, which includes an inner cable and a guide member or fixed guide path such that movement at one end of the cable results in corresponding movement at the other end of the cable. In some configurations, the linking member 2049 is a pull only arrangement that transmits a pulling force from the disengagement element 2044 to the disengageable locks 2048a, 2048b and utilizes a return biasing element to move the linking member 2049 in the return direction. In other configurations, the linking member 2049 can be a push-pull arrangement that can transmit a pushing or pulling force, if desired. The illustrated linking members 2049 do not include a continuous outer housing common to many Bowden cable arrangements, but instead are guided along a fixed length path defined by one or more guide features, such as a central guide 2047a, intermediate guides 2047b, and lateral guides 2047 (generally or collectively 2047). The guides 2047 are configured to define or alter a path of the linking member 2049 between the disengaging element 2044 and the disengageable locks 2048a, 2048b. In the illustrated arrangement, the guides 2047 are eyelets through which the linking member 2049 passes. In the illustrated arrangement, a single linking member 2049 is connected to and actuates both disengageable locks 2048a, 2048b. However, in another embodiment, each disengageable lock 2048a, 2048b can be actuated by a dedicated linking member 2049 or a single linking member 2049 can be split into multiple sub-members to control multiple disengageable locks. Although cables are shown herein, the linking member 2049 could be of any suitable arrangement, such as one or more rods, linkages, etc.

With reference to FIG. 44-46, FIG. 47A-C, FIG. 48A-B and FIG. 49, an example of a disengageable lock 2048a is illustrated in detail. The disengageable lock 2048b can be of the same or similar arrangement (e.g., a mirror image) as the disengageable lock 2048a. Furthermore, the basic components and operation of the disengageable lock 2048a can be the same as or similar to the above-described directional locks 1800, with the notable exceptions of the disengagement feature and the shape of the lock washers 1820 as described herein. The disengageable lock 2048a may comprise one or more washers 1820, a bias spring 2051 and a channel 2052 that receives a disengagement member 2053. In the illustrated arrangement, the channel 2052 is defined by the yoke 202; however, in other arrangements the channel 2052 could be defined by a structure separate from and assembled to the yoke 202. The disengagement member 2053 is attached to the linking member 2049 at a linking member connection 2055. One or more lock elements or lock washers 1820 may be received within a washer housing 646. In the illustrated arrangement, multiple (e.g., five) lock washers 1820 are provided. However, the actual number may be varied based on, among other factors, the desired locking force of the lock 2048a.

Figure 44:
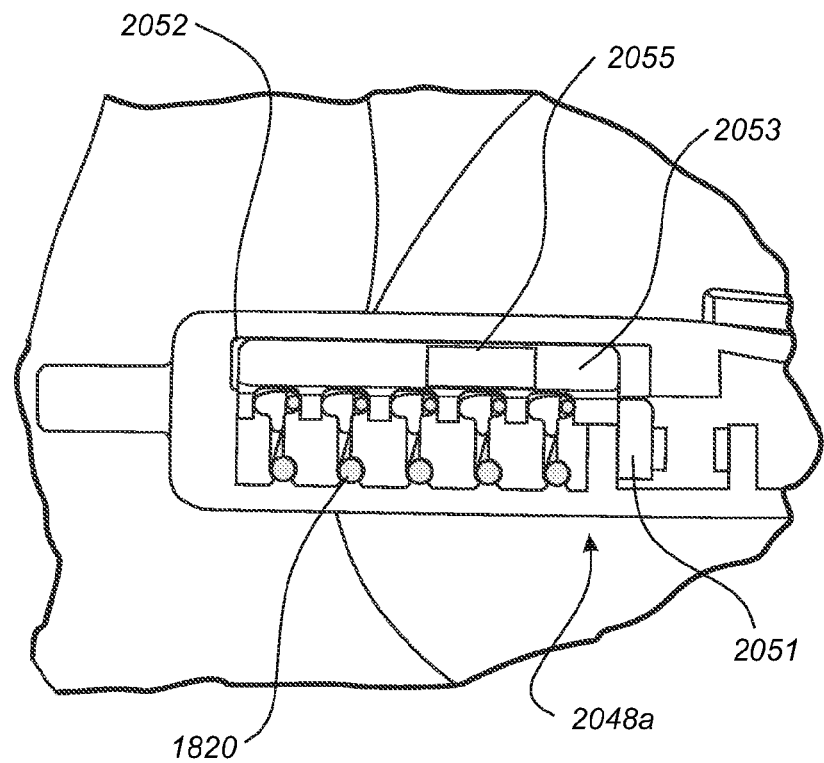
FIG. 44 is a cross-section view of a disengageable lock in an open or unlocked position.
Figure 45:
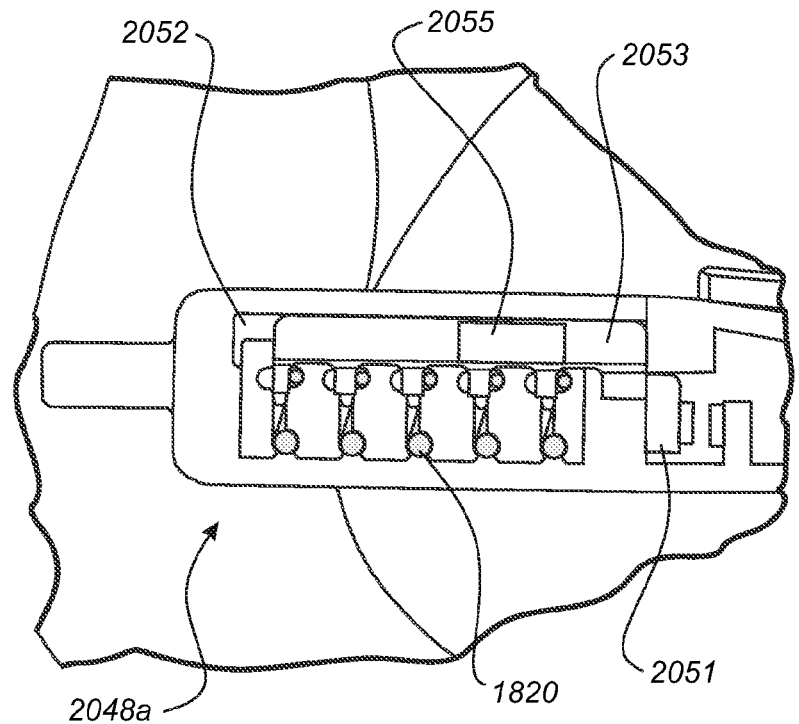
FIG. 45 is a cross-section view of a disengageable lock in a closed or locked position.
Figure 46:
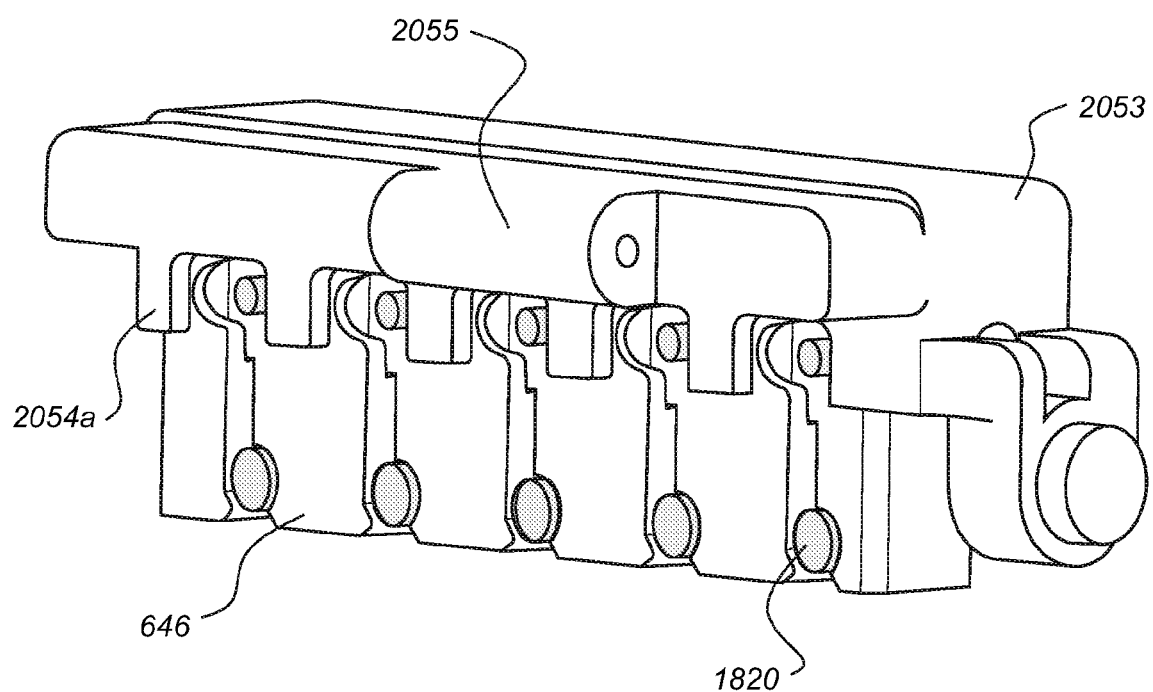
FIG. 46 is a perspective view of a disengageable lock.
Figure 47A:
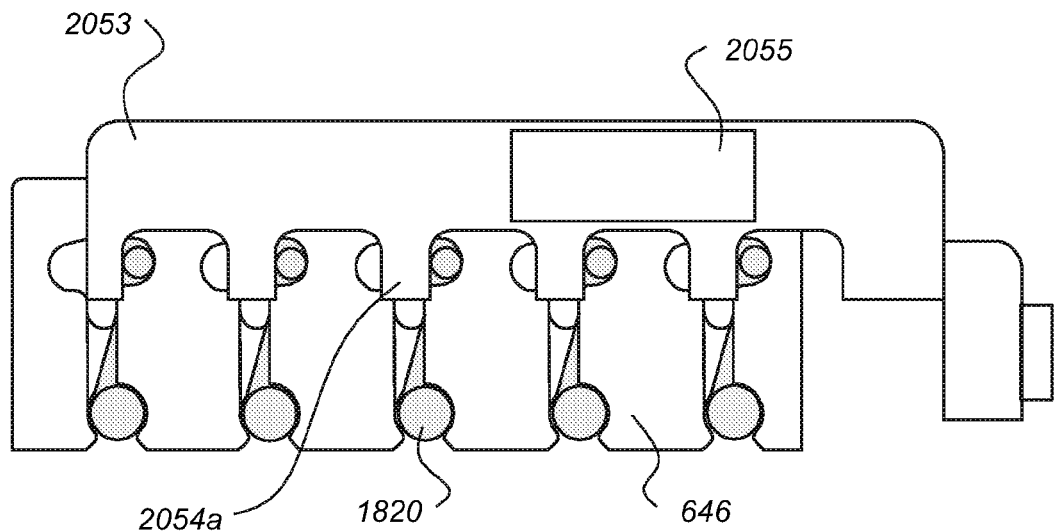
FIG. 47A is a side view of a disengageable lock in an open or unlocked position.
Figure 47B:
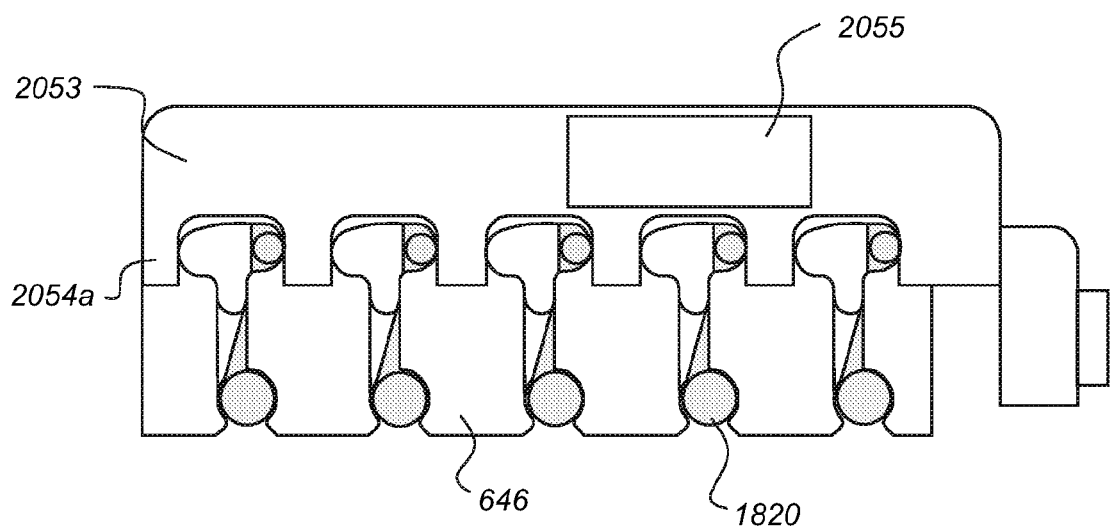
FIG. 47B is a side view of a disengageable lock in a closed or locked position.
Figure 47C:
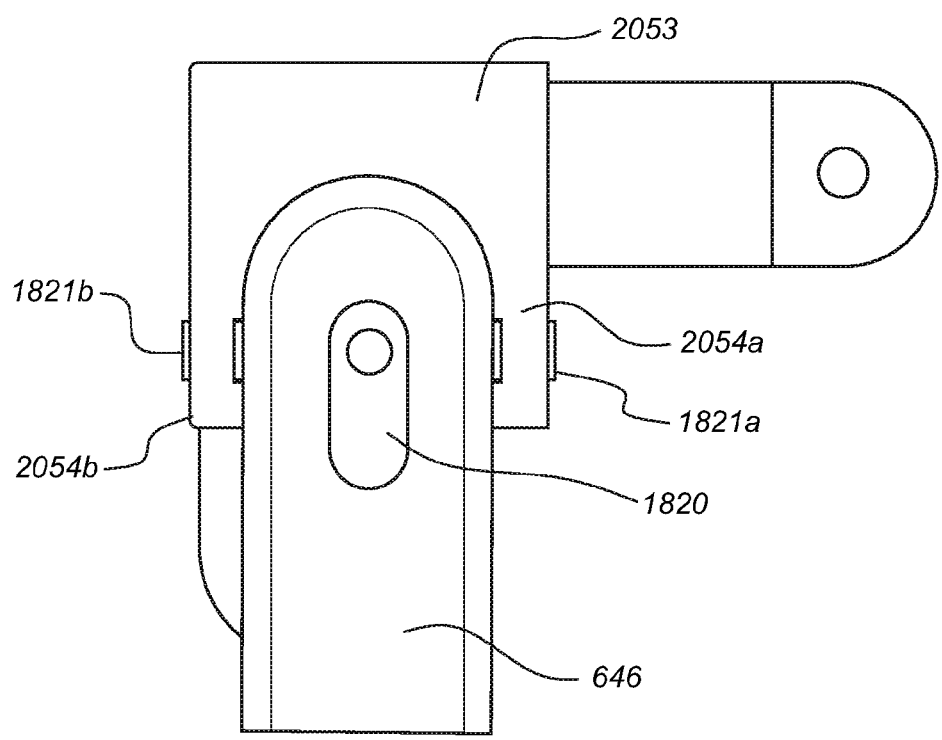
FIG. 47C is a rear view of a disengageable lock.

The disengagement member 2053 may be free to slide within channel 2052. The disengagement member 2053 is movable to selectively engage the lock washers 1820 to move the lock washers 1820 to, or retain the lock washers 1820 in (block the lock washers 1820 from moving away from), the released or unlocked position. As described above, in the released or unlocked position of the lock washers 1820, movement of the filament (not shown, e.g., 642, 1830) in the elongation direction of the associated strap 208 is not resisted or is permitted with significantly reduced resistance relative to the locked position of the lock washers 1820. The disengagement member 2053 is moved to the actuated position (engaging or blocking the lock washers 1820) or actuated by the disengagement element 2044 via the linking member 2049. This position may be referred to as the unlocked or open position of the disengagement mechanism or disengageable lock 2048a and is illustrated in FIG. 45 and FIG. 47B. The bias spring 2051, or another suitable biasing arrangement, is configured to return the disengagement member 2053 to the unactuated position in which the lock washers 1820 are free to move and operate as normal (free to move to a locked position in response to movement in an elongation direction). This position may be referred to as the locked, engaged, operable or normal position of the disengagement mechanism or disengageable lock 2048a and is illustrated in FIG. 44 and FIG. 47A.

In the unactuated position of disengagement member 2053, the washers 1820 are permitted to move between an unlocked and a locked position in response to retraction and elongation movement, respectively, of the strap 208 or headgear 200. As discussed with reference to FIG. 25A to 25D, if the washers 1820 are permitted to move or pivot, the movement of filament or core member 1830 in the elongation direction may be restricted (e.g., inhibited or prevented) by friction between core member 1830 and washers 1820. Conversely, if the washers 1820 are held in the unlocked position, the friction between core member 1830 and washers 1820 is reduced and movement of core member 1830 in the elongation direction becomes easier relative to the locked position.

Figure 48A:
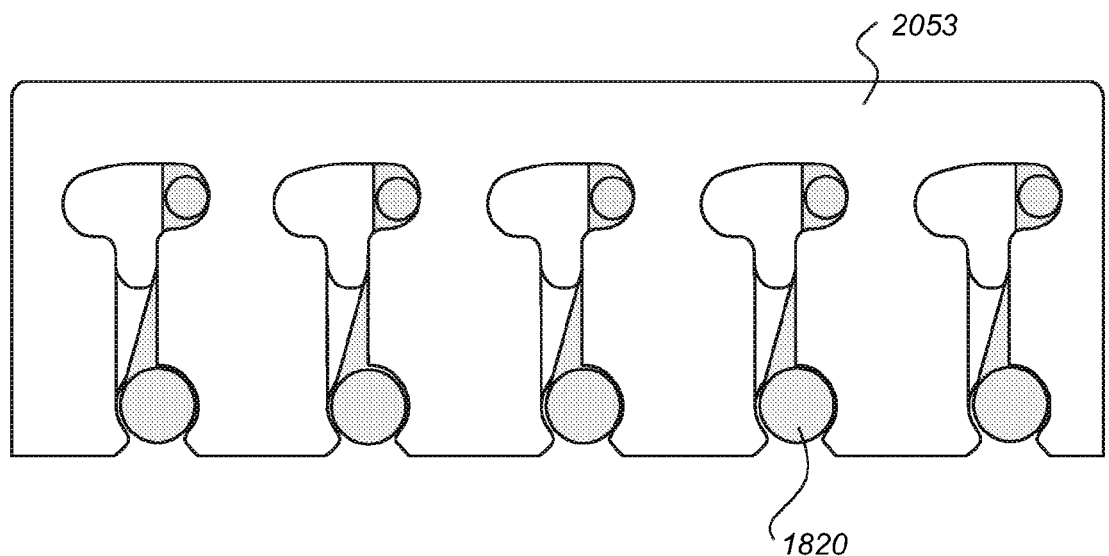
FIG. 48A is a side view of the washer housing with washers of the disengageable lock of FIG. 44.
Figure 48B:
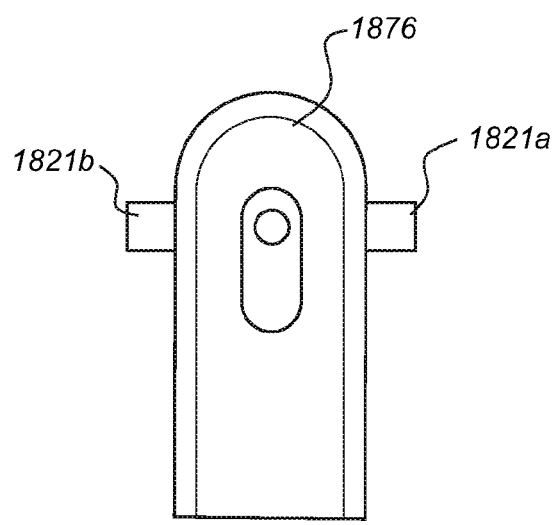
FIG. 48B is a rear view of the washer housing and washers of the disengageable lock of FIG. 44.
Figure 49:
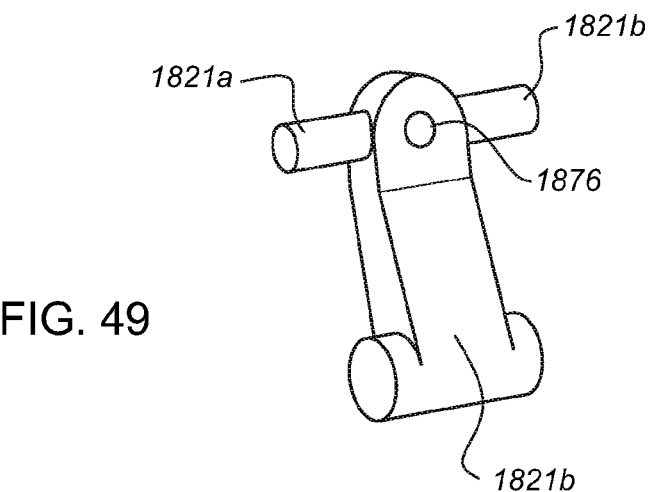
FIG. 49 is a perspective view of an embodiment of a washer.

With reference to FIGS. 48B and 49, each of the washers 1820 may comprise one or more protrusions 1821a, 1821b. These protrusions 1821a, 1821b may define engagement surfaces configured for selective engagement with the disengagement member 2053 to move the washers 1820 to the unlocked position or block the washers 1820 from moving away from the unlocked position, and thus allow the relatively free movement of the core member 1830 in the elongation direction (as well as the retraction direction). The disengagement member 2053 can include an appropriate number of actuators 2054a, 2054b configured to contact the protrusions 1821a, 1821b. In the illustrated arrangement, the actuators 2054a, 2054b are in the form of tabs or arms that extend from a main body portion of the disengagement member 2053. In the illustrated arrangement, a protrusion 1821a, 1821b is located on each side of the washer 1820 such that a balanced force is applied to each side of the washer 1820 by the corresponding actuators 2054a, 2054b of the disengagement member 2053, which are similarly provided on each side of the disengagement member 2053, to provide for smooth pivoting movement of the washer 1820 and reduce or prevent binding.

Figure 50:
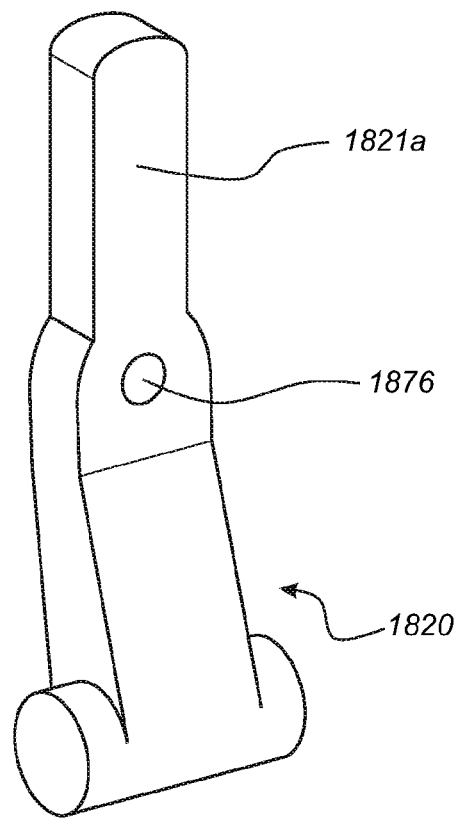
FIG. 50 is a perspective view of an alternative embodiment of a washer.
Figure 52:
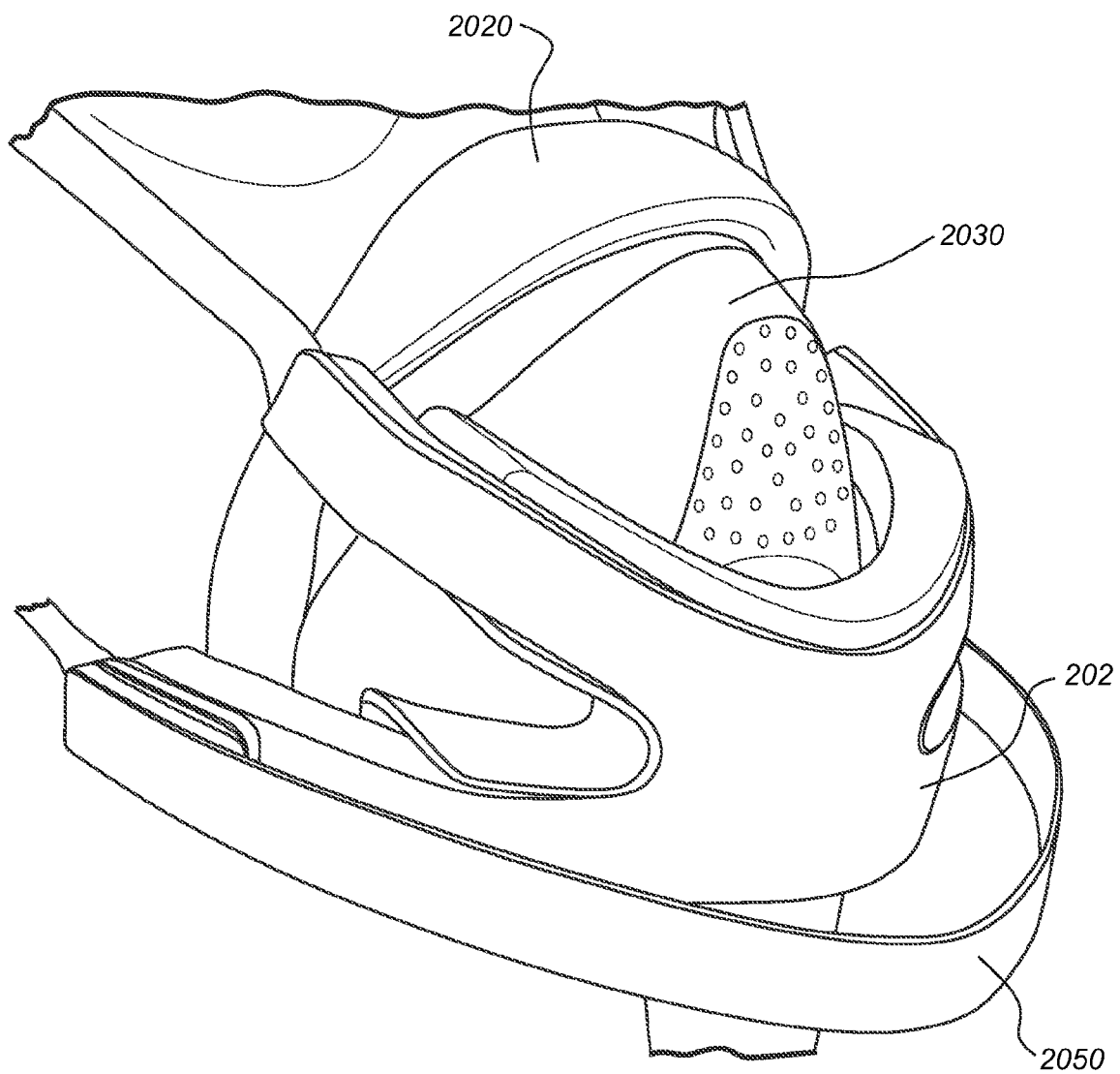
FIG. 52 is a perspective view of a mask assembly, including a headgear assembly, a seal assembly, and a frame assembly fastened to a wearer's head with a disengageable coupling comprising a disengagement handle.
Figure 53:
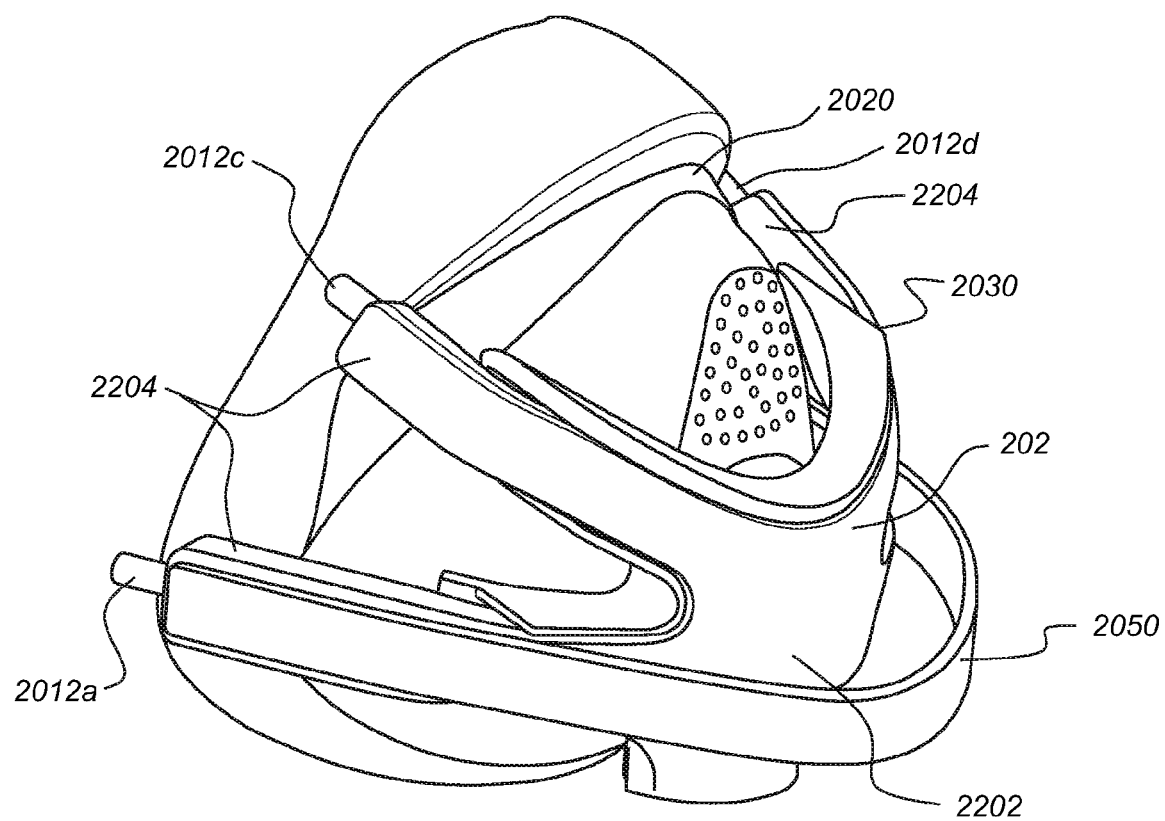
FIG. 53 is a perspective view of a mask assembly, including a yoke portion of a headgear assembly, a seal assembly, and a frame assembly with a disengageable coupling comprising a disengagement handle.
Figure 54:
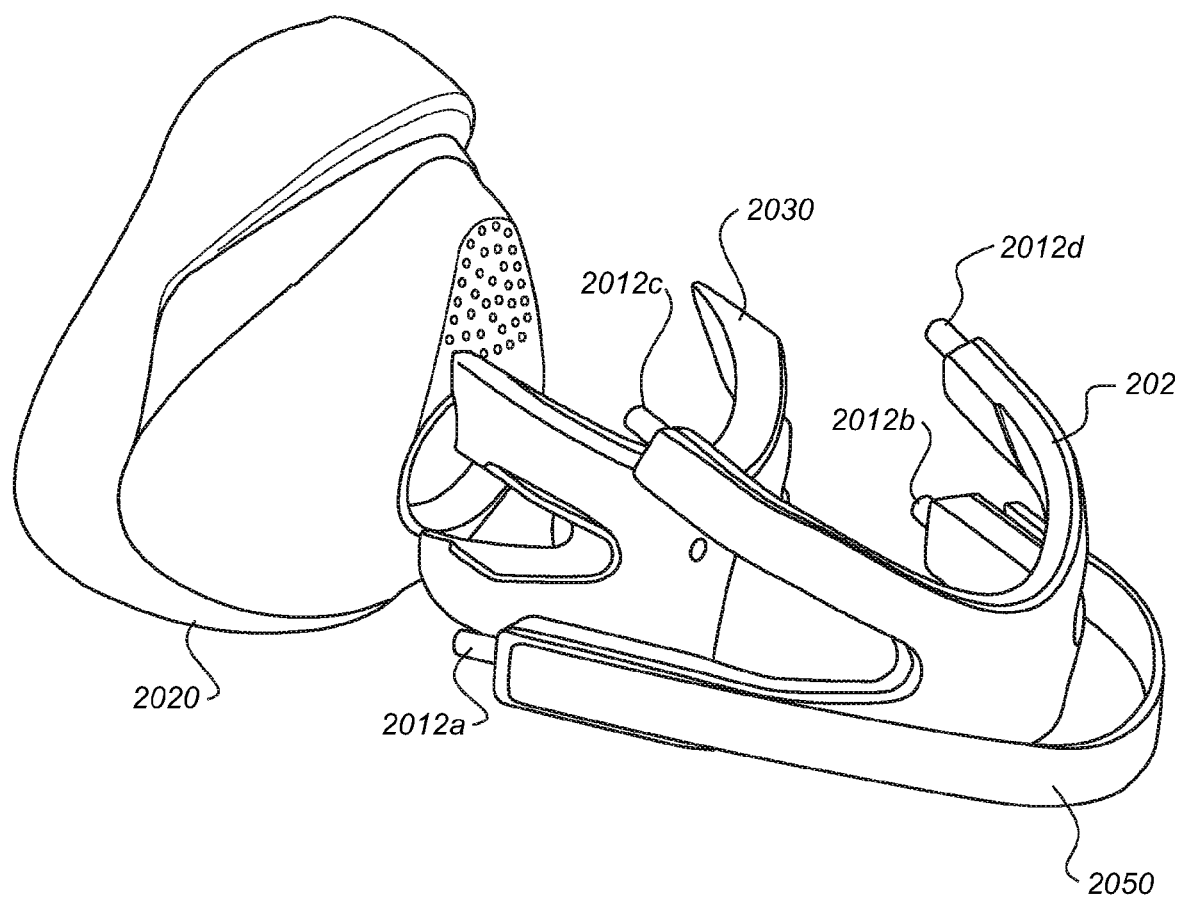
FIG. 54 is an exploded view of the cushion module, mask frame and yoke of FIG. 53.

FIG. 50 illustrates an alternative washer 1820 that includes only one protrusion 1821a. In the arrangement of FIG. 50, the single protrusion 1821a is centrally-located relative to the pivoting structure engaged by the housing 1810 to reduce or prevent binding. However, in some configurations, an off-center protrusion 1821 or protrusions can be employed and binding can be resisted by other methods or structures, such as the pivoting arrangement, for example. Other arrangements, including multiple protrusions, and other geometries, may be used in addition to or in the alternative of protrusions 1821a.

With reference to FIG. 51A-C, a lock 2058 that is in some aspects similar to disengageable locks 2048a, 2048b is illustrated that incorporates washers 1820 in a washer housing 646, but does not incorporate a disengageable mechanism. In some configurations, the basic components and operation of the lock 2058 can be the same as or similar to the above-described directional locks 1800, except as described herein. The illustrated lock 2058 includes multiple washers 1820. In particular, in the illustrated arrangement, the lock 2058 includes three washers. In some configurations, each of the locks 2058 include a lesser number of washers than each of the disengageable locks 2048a, 2048b. In some such configurations, one or more locks 2058 are employed in each upper strap 208 of the headgear 200 and one or more locks 2048a, 2048b are employed in each lower strap 208 of the headgear 200. It will be appreciated that any desired combination of disengageable locks 2048a, 2048b and non-disengageable locks 2058 may be used in the same mask assembly.

Figure 55:
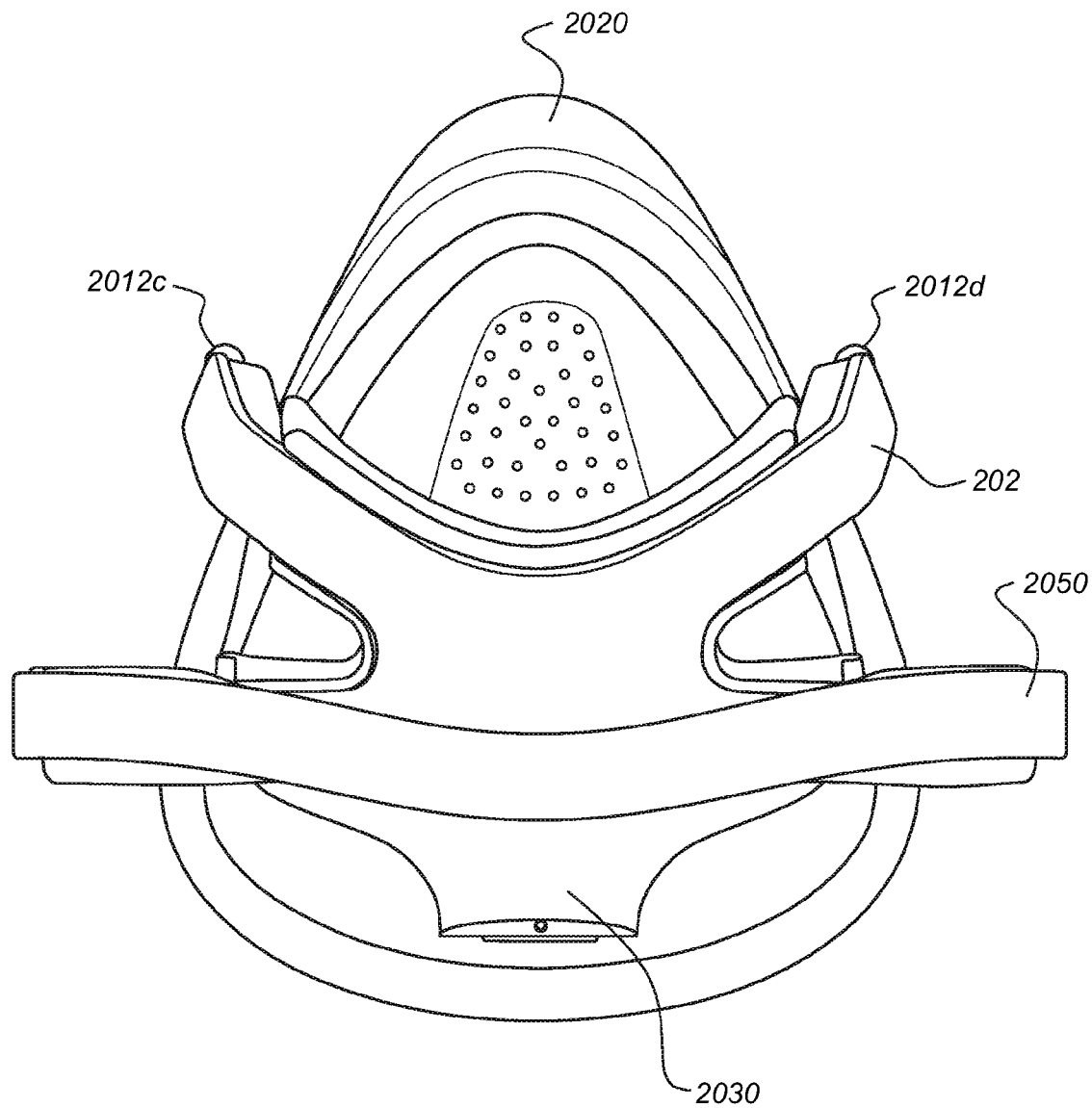
FIGS. 55, 56, 57, 58A and 58B are various perspective views of the assembled cushion module, mask frame and yoke of FIG. 53.
Figure 56:
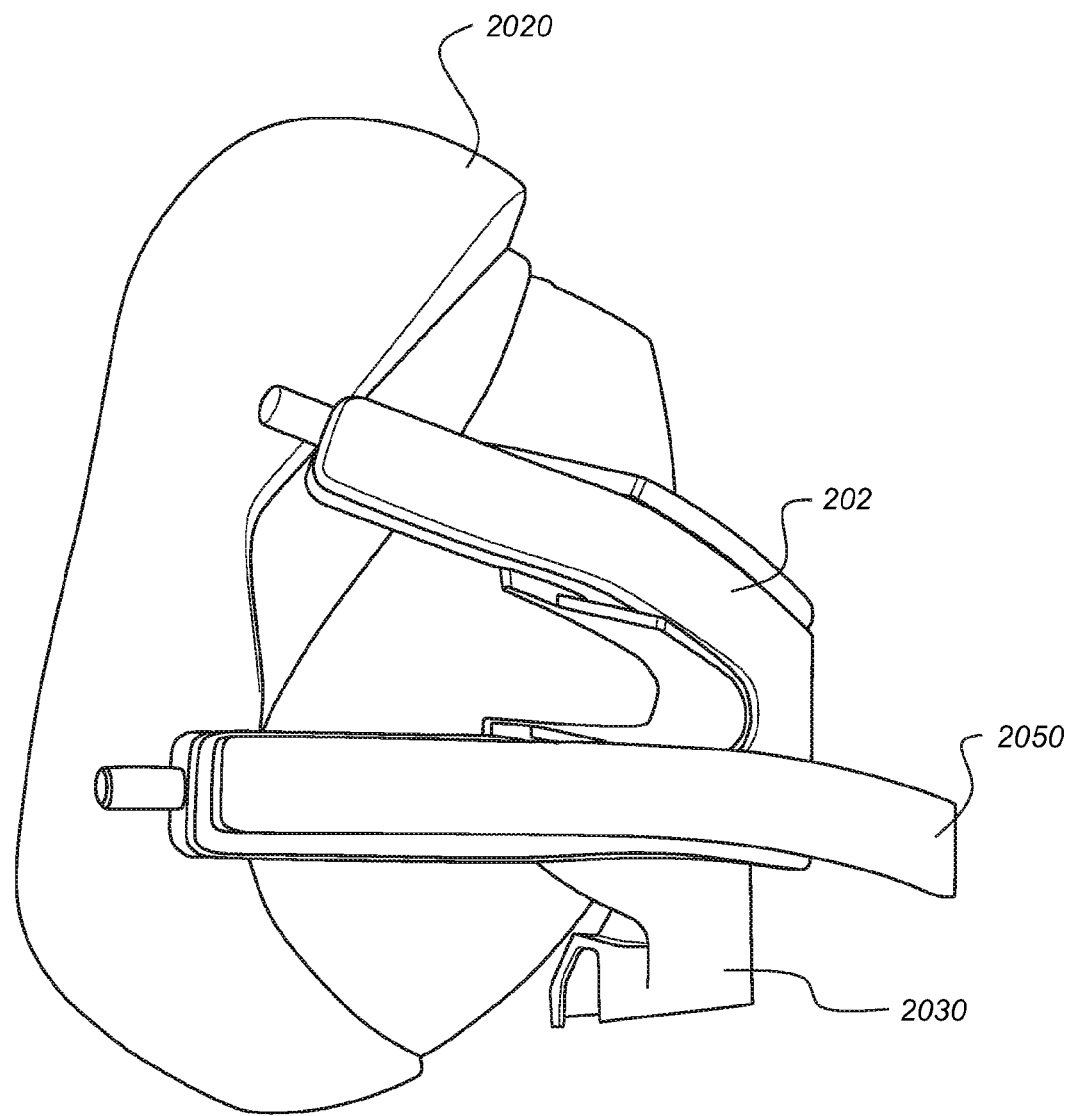
Figure 57:
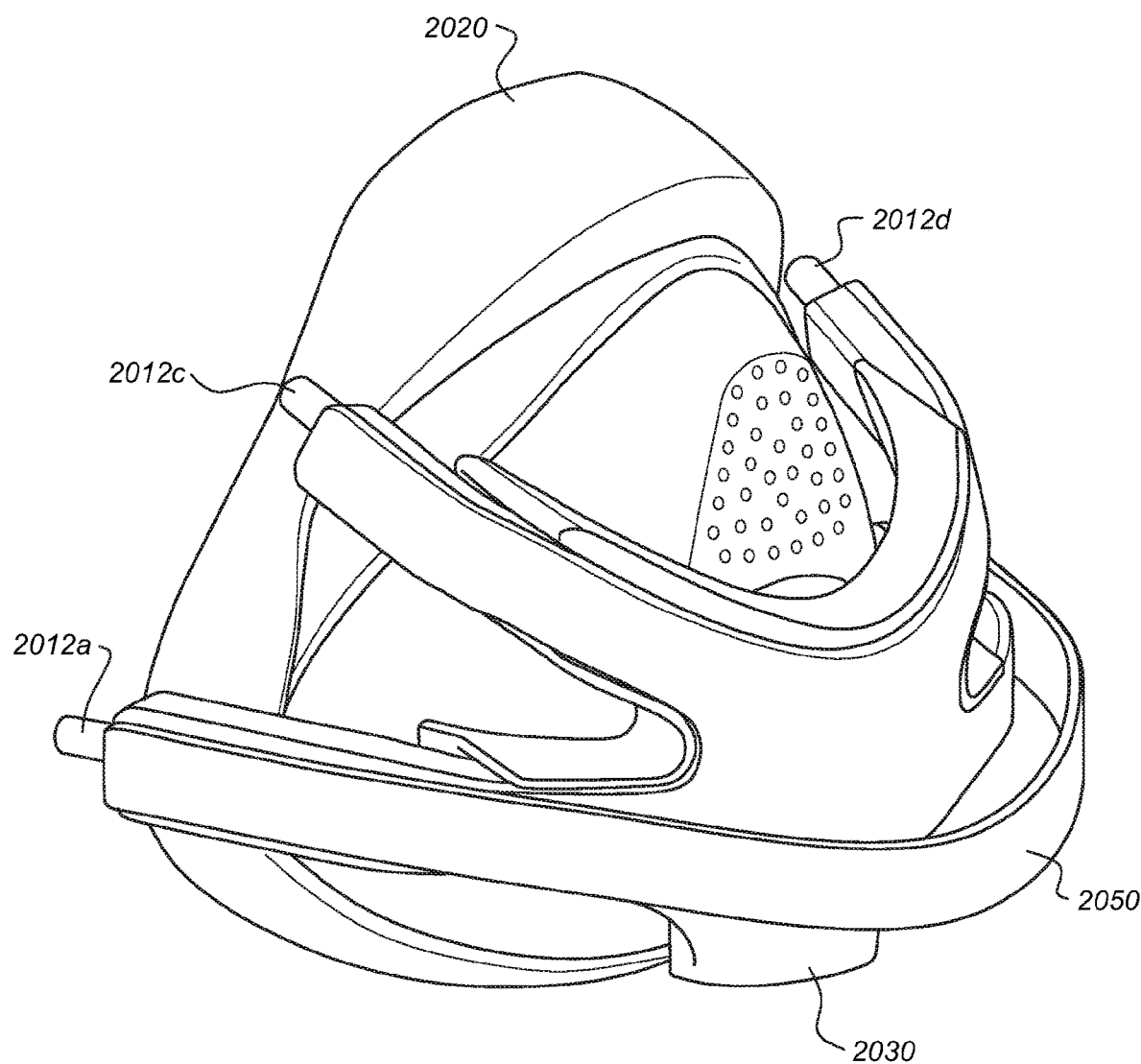
Figure 58A:
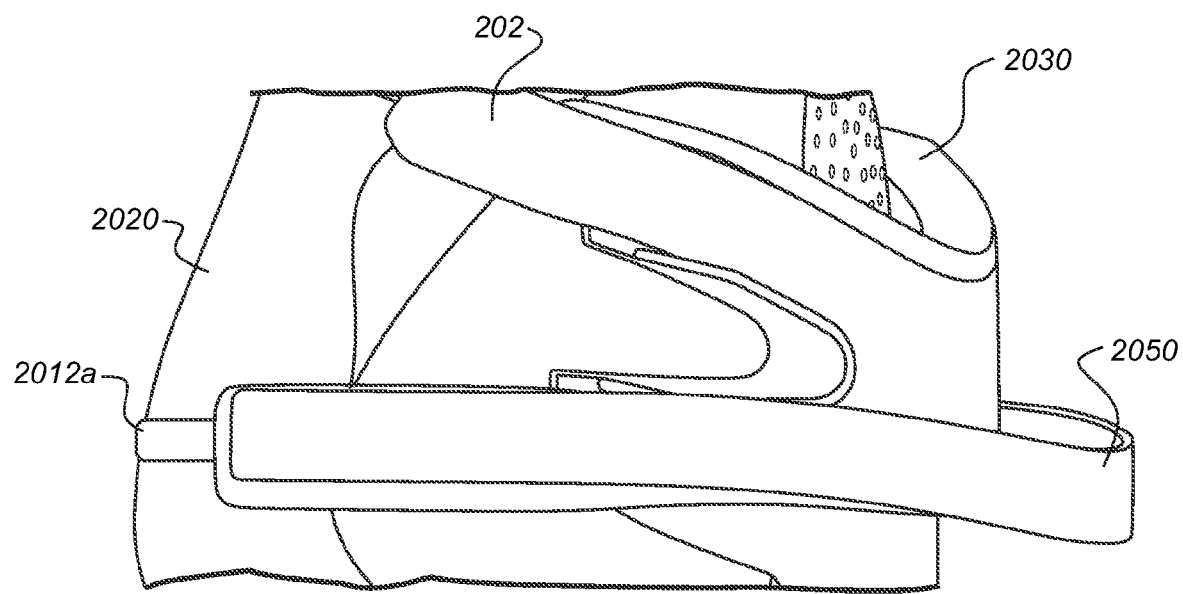
Figure 58B:
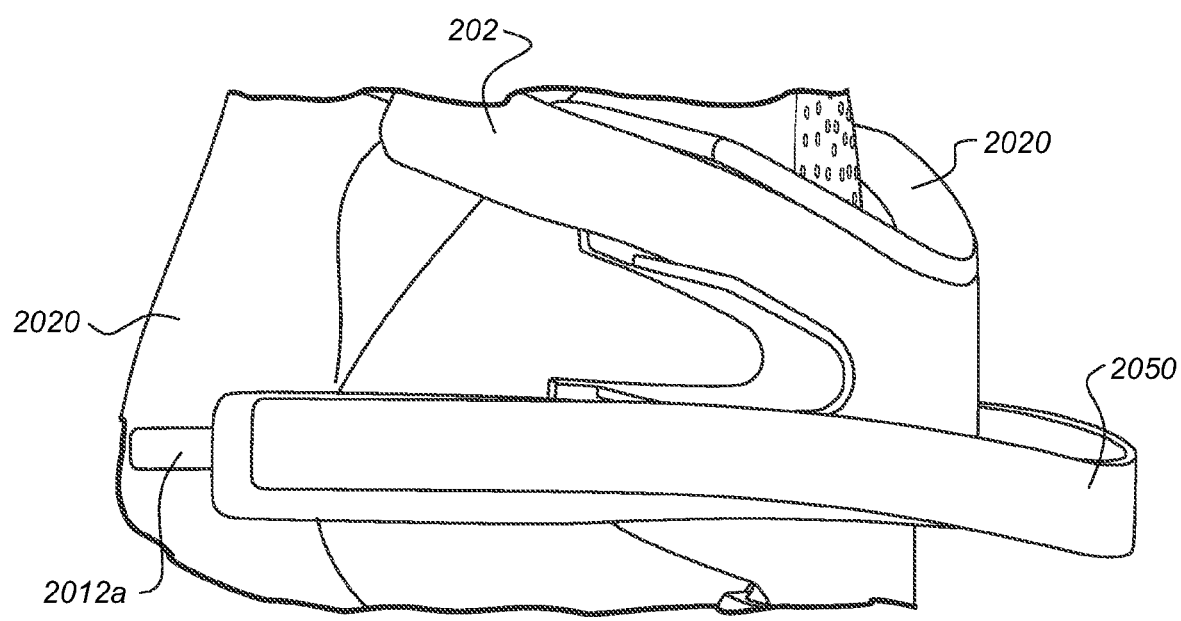
Figure 59:
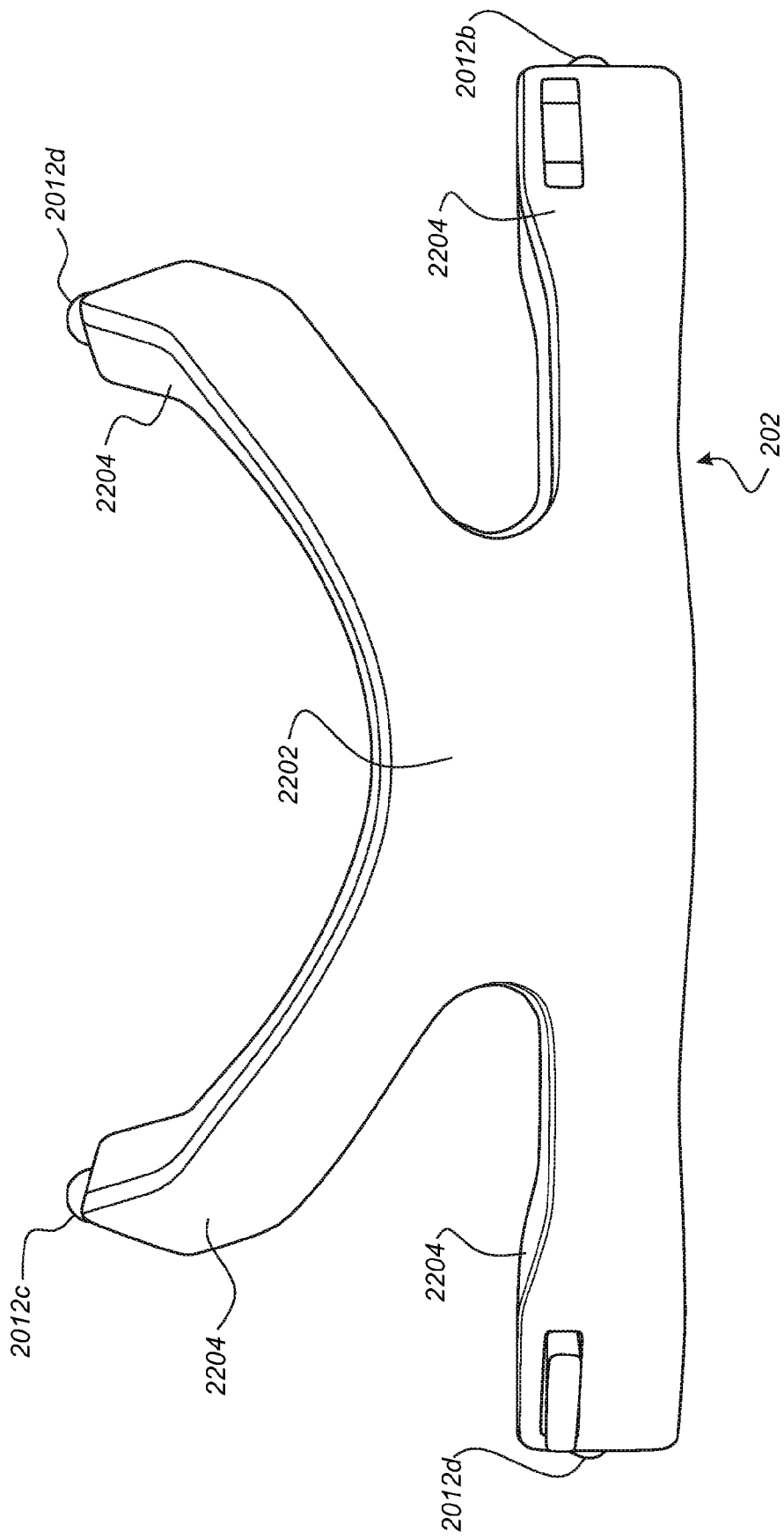
FIG. 59 is a front view of a yoke comprising a disengagement handle.
Figure 60A:
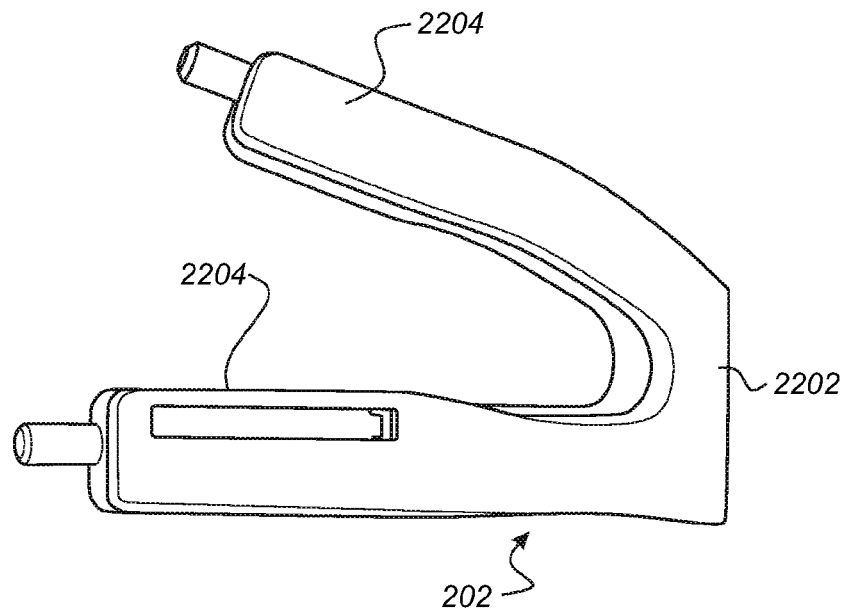
FIG. 60A is a side view of a yoke configured to utilize a disengagement handle.
Figure 60B:
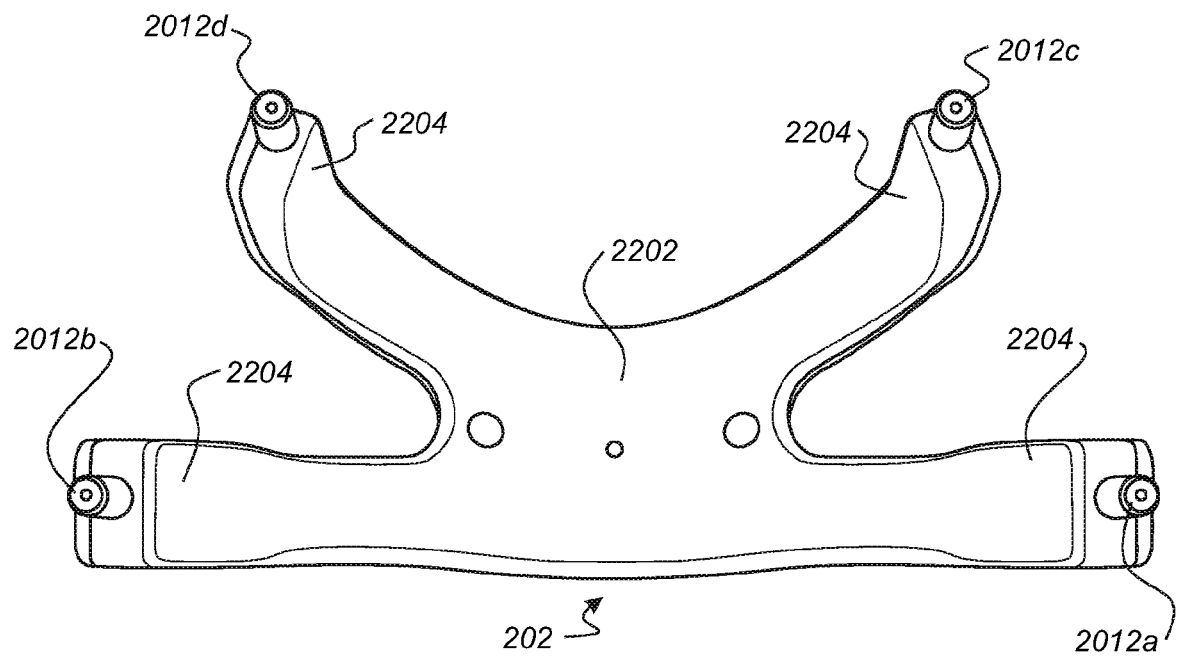
FIG. 60B is a back view of a yoke configured to utilize a disengagement handle.
Figure 61:
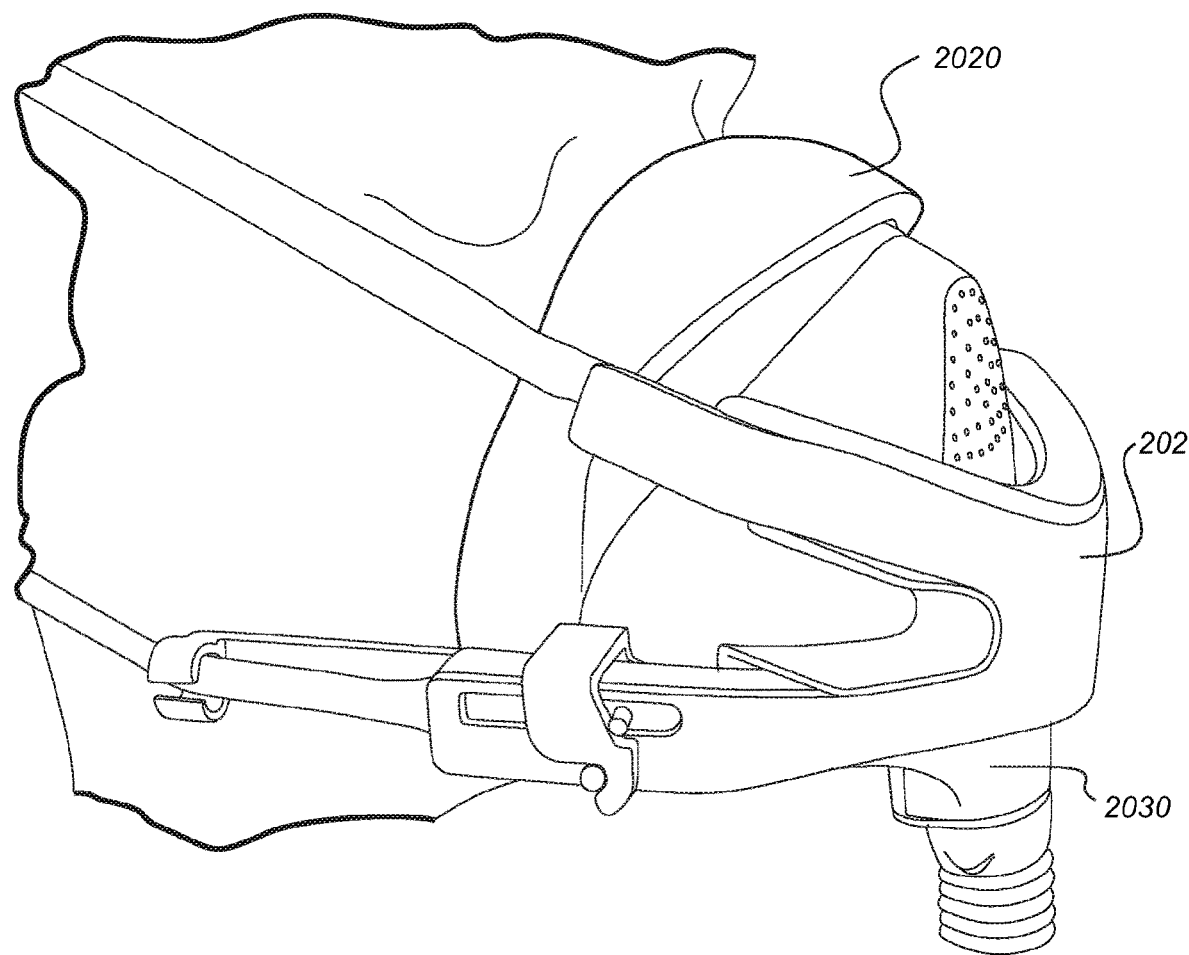
FIG. 61 is a perspective view of a mask assembly, including a headgear assembly, a seal assembly, and a frame assembly with a disengageable coupling comprising a tilt action disengagement mechanism.
Figure 62:
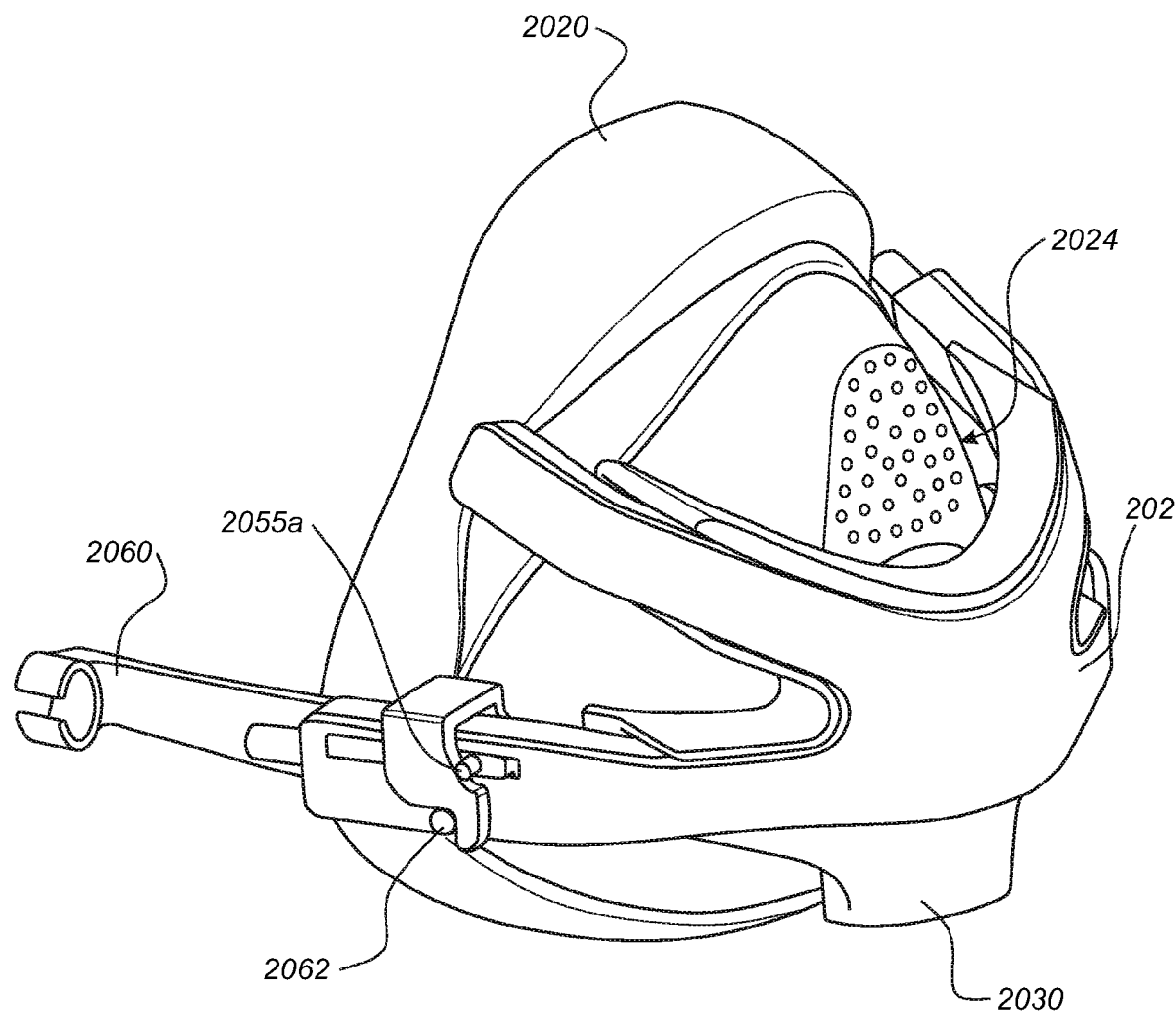
FIG. 62 is a perspective view of the cushion module, mask frame and yoke of FIG. 61.

With reference to FIG. 52-60B, another embodiment of a mask assembly is disclosed that may be similar in certain aspects to the mask assembly illustrated in FIGS. 26-51C, but includes a disengagement element in the form of a disengagement handle 2050 instead of the disengagement bar 2044 of FIGS. 26-51C. Accordingly, features that are not described in detail herein can be the same as or similar to corresponding features disclosed herein, or can be of another suitable arrangement. The disengagement handle 2050 may be attached to yoke 202 and may be directly or indirectly connected to the disengagement member 2053 so that pulling on handle 2050 transmits a force to disengagement member 2053. In the illustrated arrangement, the disengagement handle 2050 is directly connected to the disengagement member 2053. In other arrangements, the disengagement handle 2050 can be integrated with the disengagement member 2053 or can be connected to the disengagement member 2053 by intervening structure so as to gain a mechanical advantage, change the direction or type of motion, or avoid interference with other structures, among other possibilities. In an embodiment, disengagement handle 2050 may be configured so that a wearer of the mask can grasp and pull the handle away from his face, thereby moving the disengagement member 2053 to the actuated position, as illustrated in FIG. 58B. With particular reference to FIGS. 55 and 56, disengagement handle 2050 can curve downwardly from the side portions to the central or forward portion such that an upper surface of the central portion is concave. Such an arrangement provides an intuitive portion of the disengagement handle 2050 for the user to grasp. As disclosed herein, when the disengagement member 2053 is in the actuated position, the disengageable locks 2048a, 2048b are disengaged such that the locks 2048a, 2048b do not significantly resist elongation movement of the lower straps 208 of the headgear 200. Upon the user releasing the disengagement handle 2050, the bias spring 2051 may return the disengagement member 2053 to its unactuated position, as illustrated in FIG. 58A, thus also retracting disengagement handle 2050. In such a position, the disengageable locks 2048a, 2048b operate normally and inhibit or prevent elongation movement of the lower straps 208 of the headgear 200.

With reference to FIG. 61-70, another mask assembly is disclosed that may be similar in certain aspects to the other mask assemblies disclosed herein with respect to FIGS. 26-60B, but includes a disengagement arm 2060 attached to yoke 202 in place of, or in addition to, the disengagement handle 2050 or the disengagement bar 2044. Accordingly, features that are not described in detail herein can be the same as or similar to corresponding features disclosed herein, or can be of another suitable arrangement. The illustrated mask assembly includes one disengagement arm 2060 on one side of the yoke 202 and configured to interact with one of the lower straps 208 of the headgear 200 and the disengagement member 2053 of the disengageable lock 2048a. In some configurations, another disengagement arm (which can be a mirror image of the disengagement arm 2060) can be employed on the opposite lower strap 208 of the headgear 200 and configured to interact with the other lower disengeageable lock 2048b. Alternatively, a linking member or other motion transfer arrangement can be configured to link both locks 2048a, 2048b to movement of a single disengagement arm 2060. In other arrangements, disengagement arms 2060 can be employed on any or all straps 208 of the headgear 200.

The disengagement arm 2060 is movable relative to the yoke 202. In some configurations, the disengagement arm 2060 is configured to pivot relative to or is pivotally supported by the yoke 202. In the illustrated arrangement, the yoke 202 includes a pivot 2062 in the form of at least one protrusion configured to be engaged by, received in, or held within a complementary feature of the disengagement arm 2060. The protrusion can be cylindrical as illustrated. Preferably, the yoke 202 includes a pivot 2062 on each of a side facing away from the user and a side facing towards the user. Accordingly, the disengagement arm 2060 may be configured to pivot, rotate or swivel around a pivot axis defined by the pivot 2062.

Figure 63:
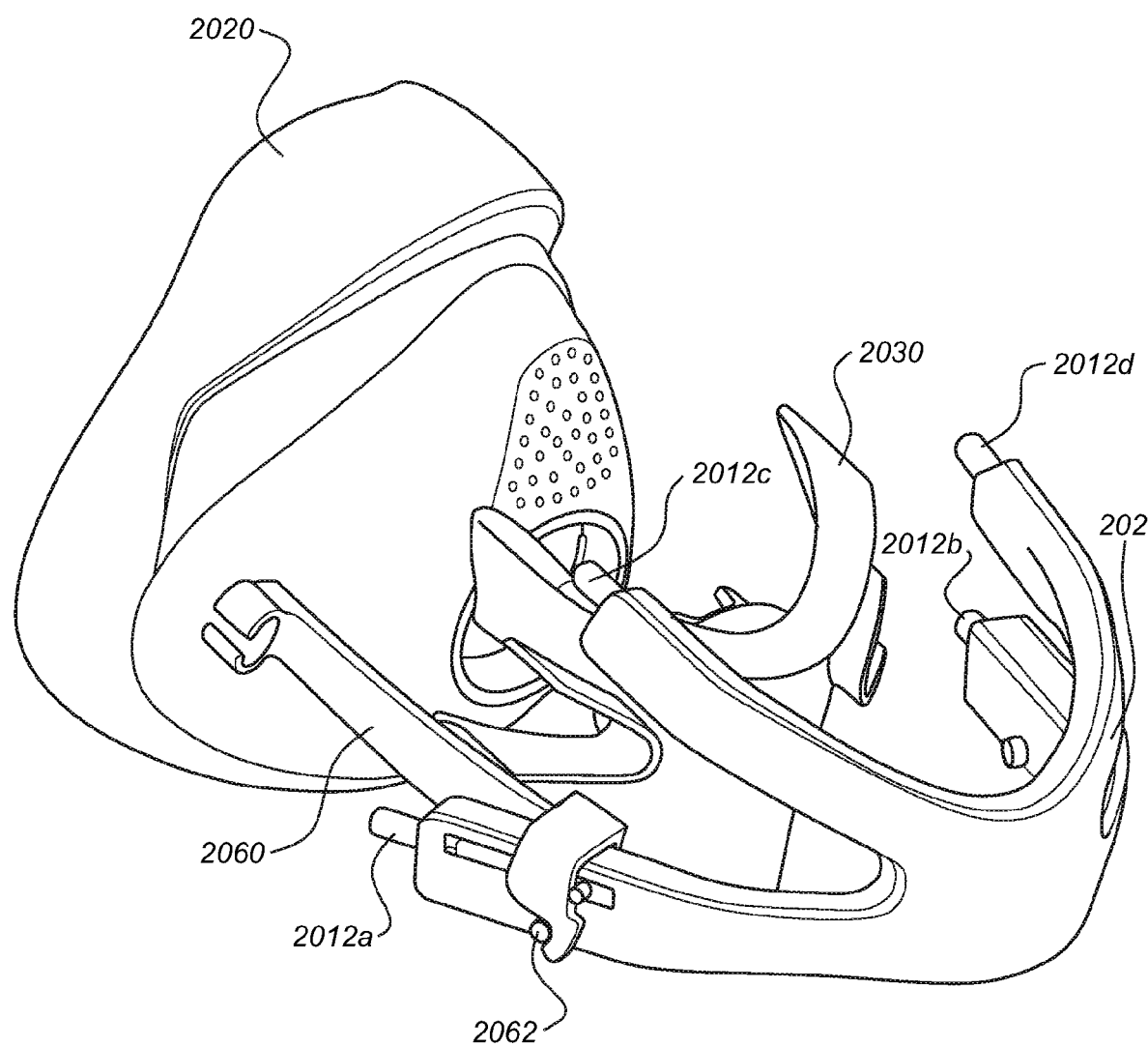
FIG. 63 is an exploded view of the cushion module, mask frame and yoke of FIG. 61.
Figure 64:
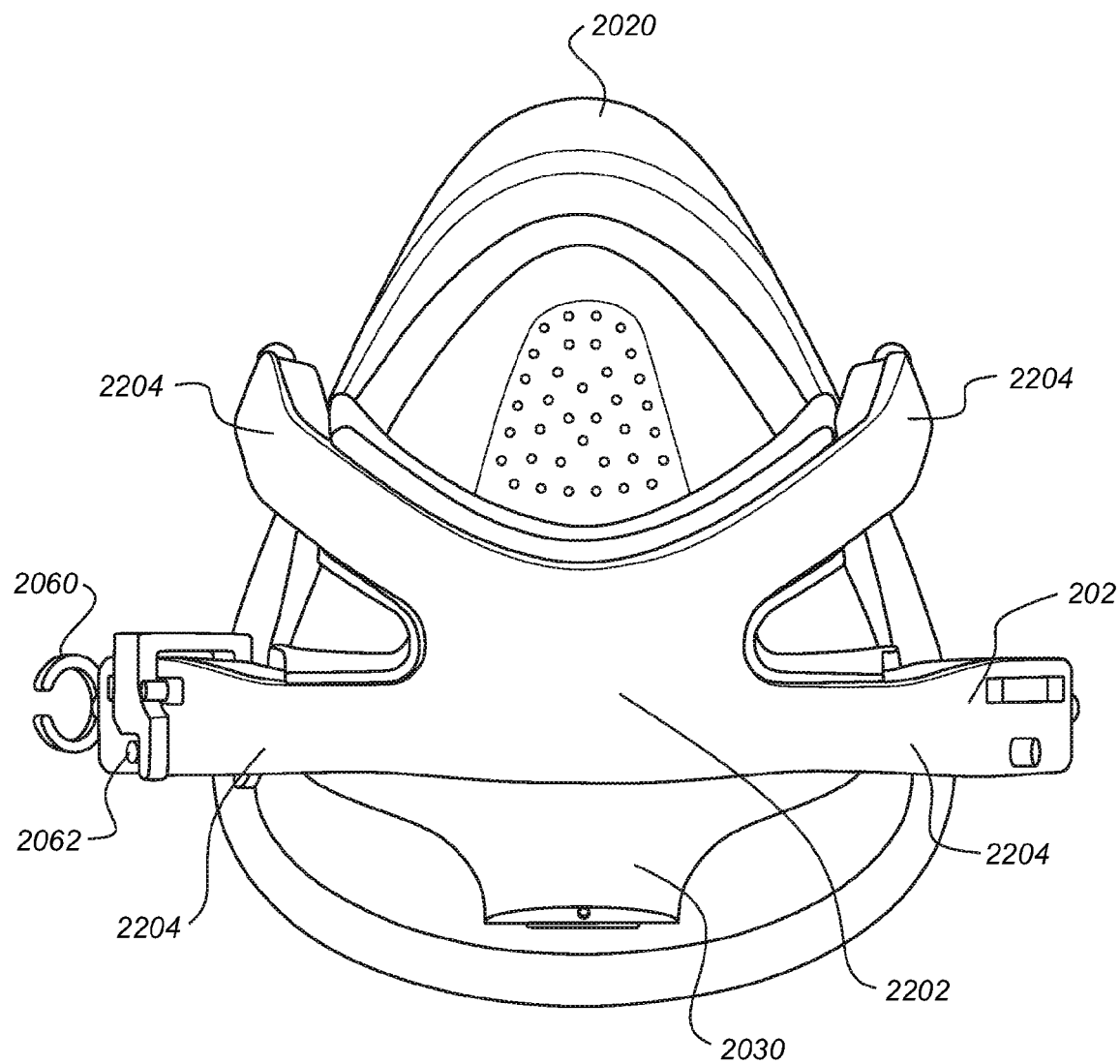
FIG. 64 is a front view of the cushion module, mask frame and yoke of FIG. 61.
Figure 65:
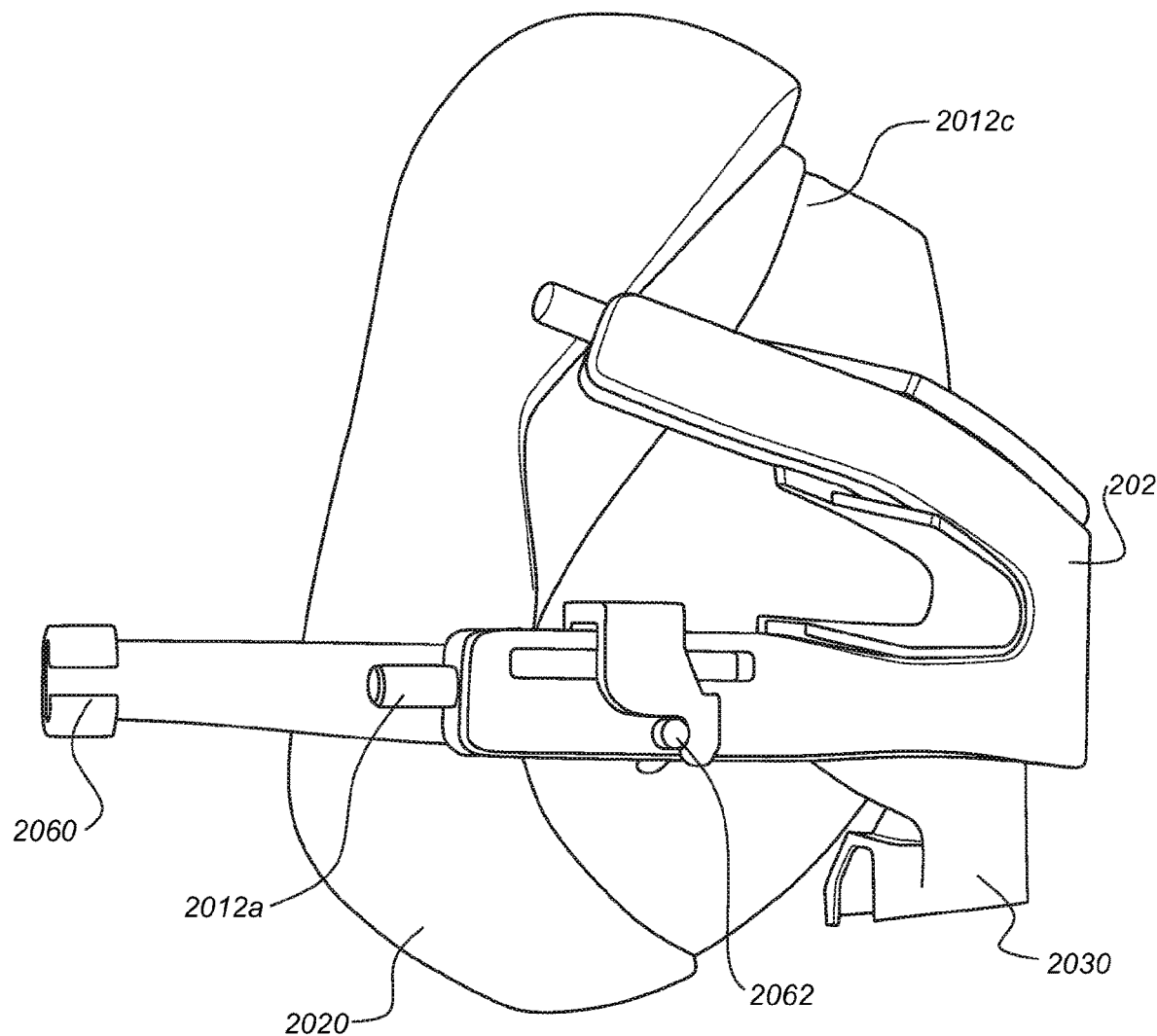
FIG. 65 is a side view of the cushion module, mask frame and yoke of FIG. 61.
Figure 66:
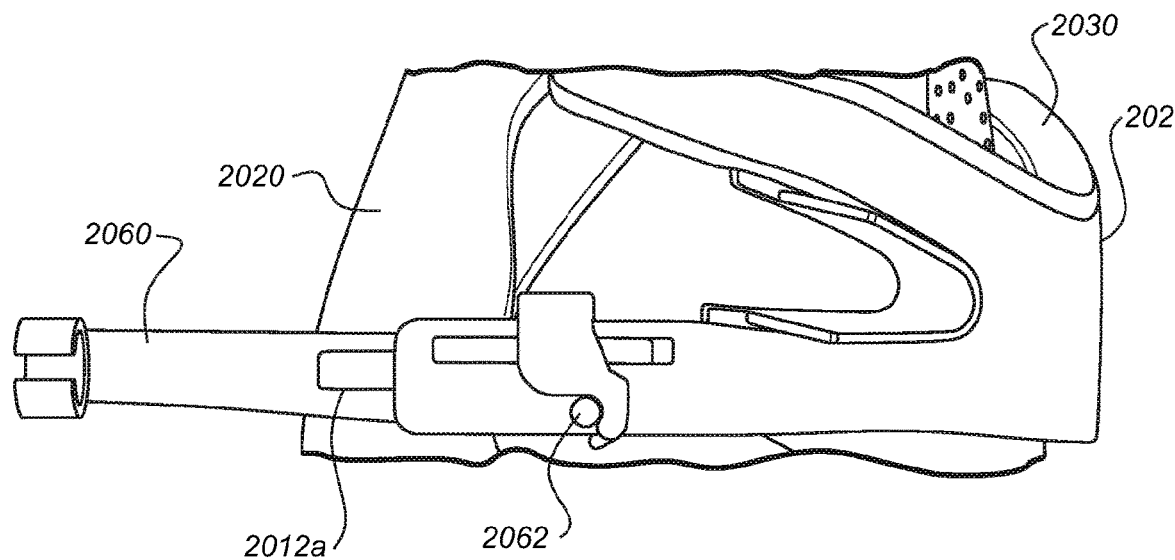
FIG. 66 is a side view of the cushion module, mask frame and yoke of FIG. 61, with the tilt action mechanism in an engaged (open) position.
Figure 67:
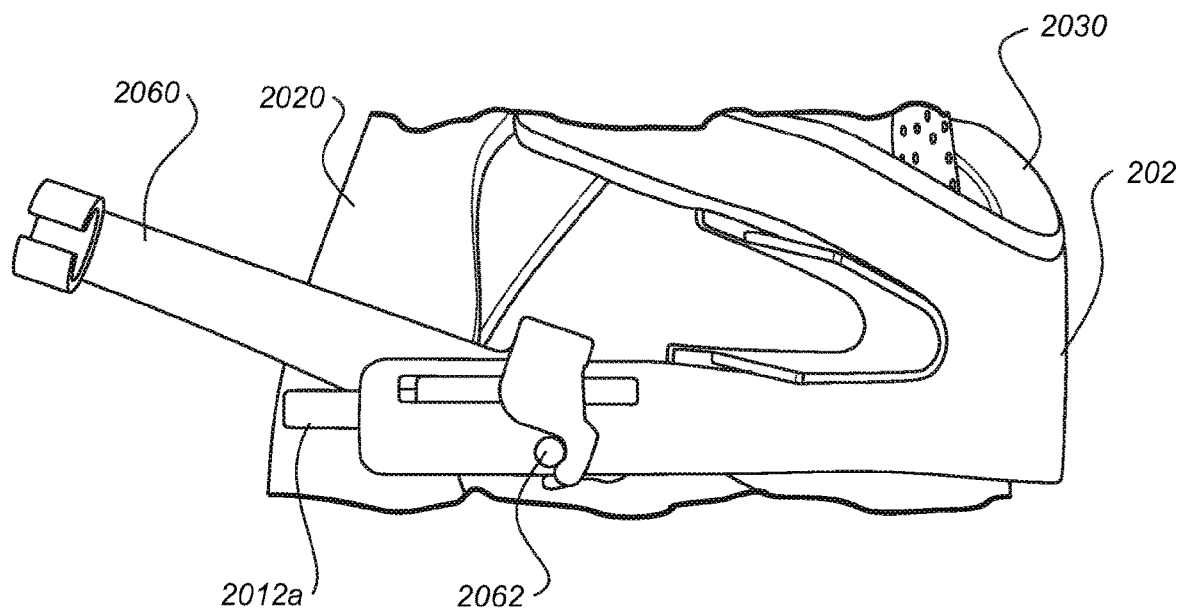
FIG. 67 is a side view of the cushion module, mask frame and yoke of FIG. 61, with the tilt action mechanism in a disengaged (closed) position.
Figure 68:
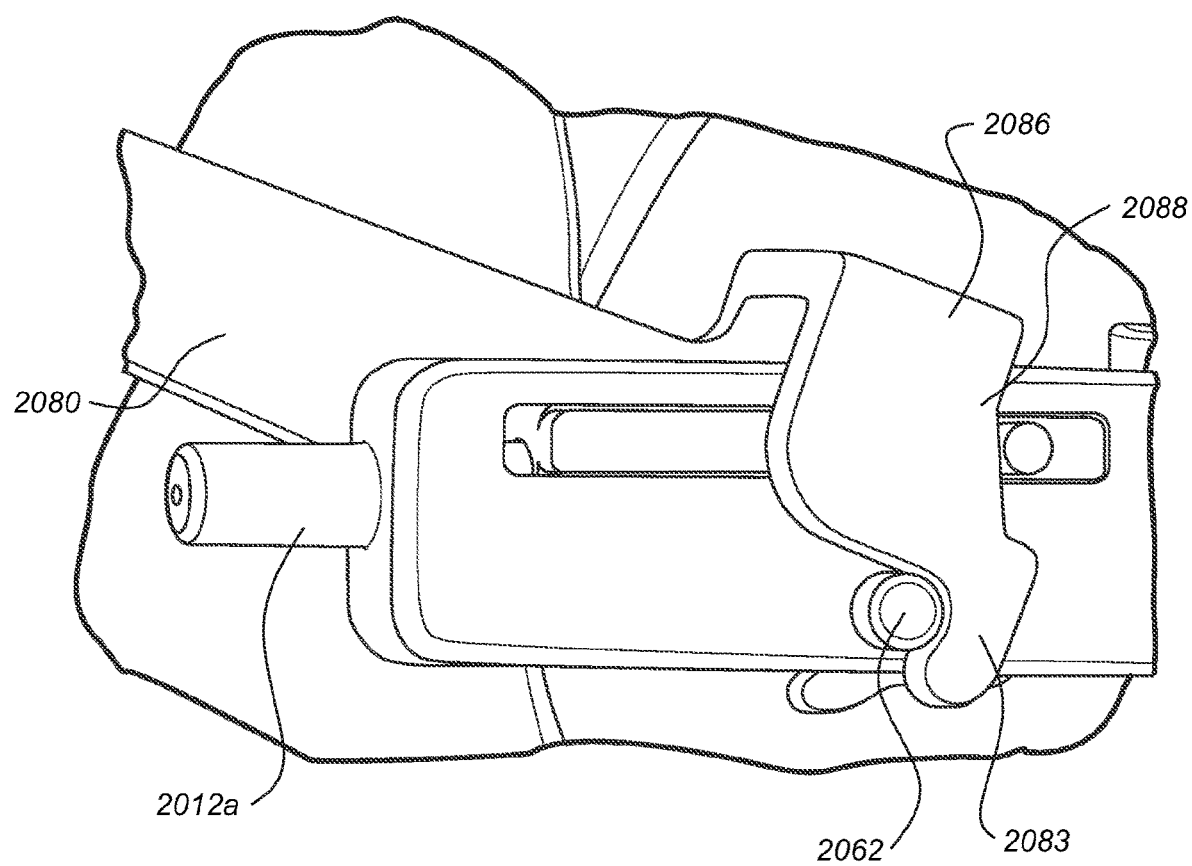
FIG. 68 is a perspective view of the tilt action mechanism of a yoke as shown in FIG. 61.
Figure 69:
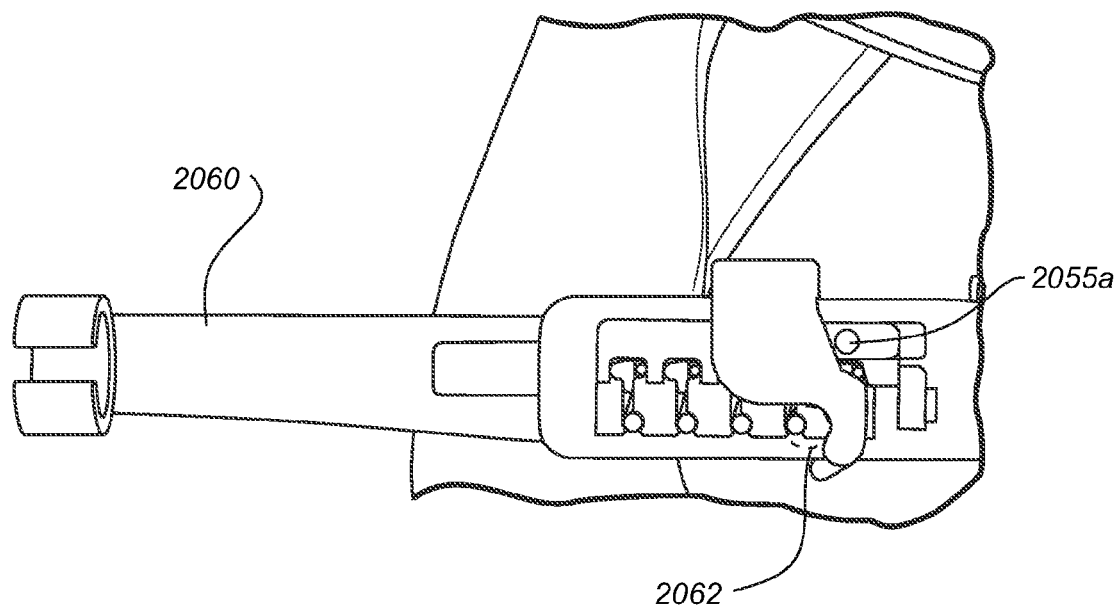
FIG. 69 is a cross-section view of various components of a tilt action mechanism in an engaged (open) position.
Figure 70:
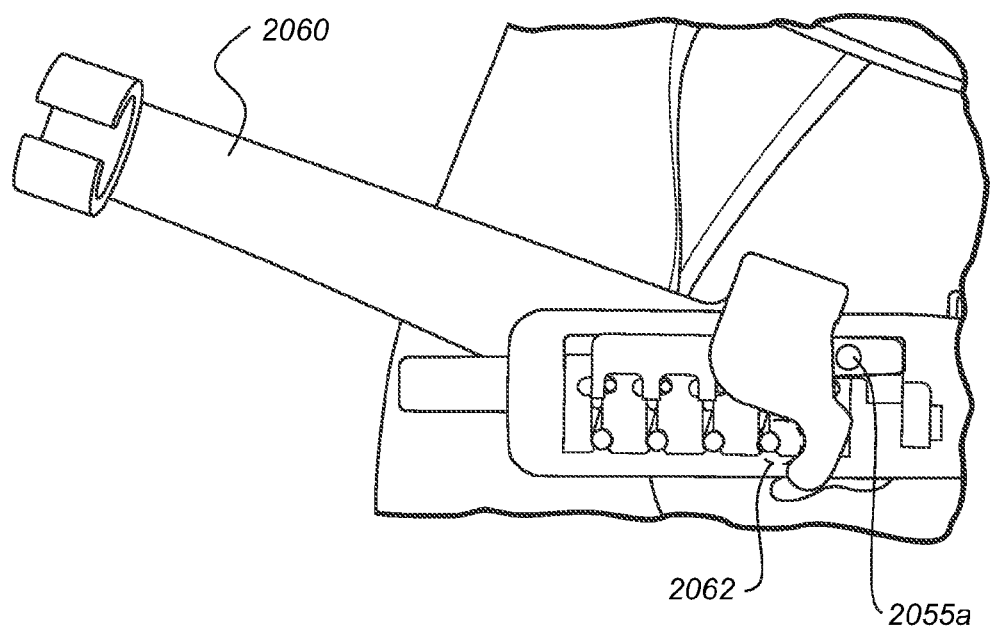
FIG. 70 is a cross-section view of various components of a tilt action mechanism, with the tilt action mechanism in a disengaged (closed) position.
Figure 71:
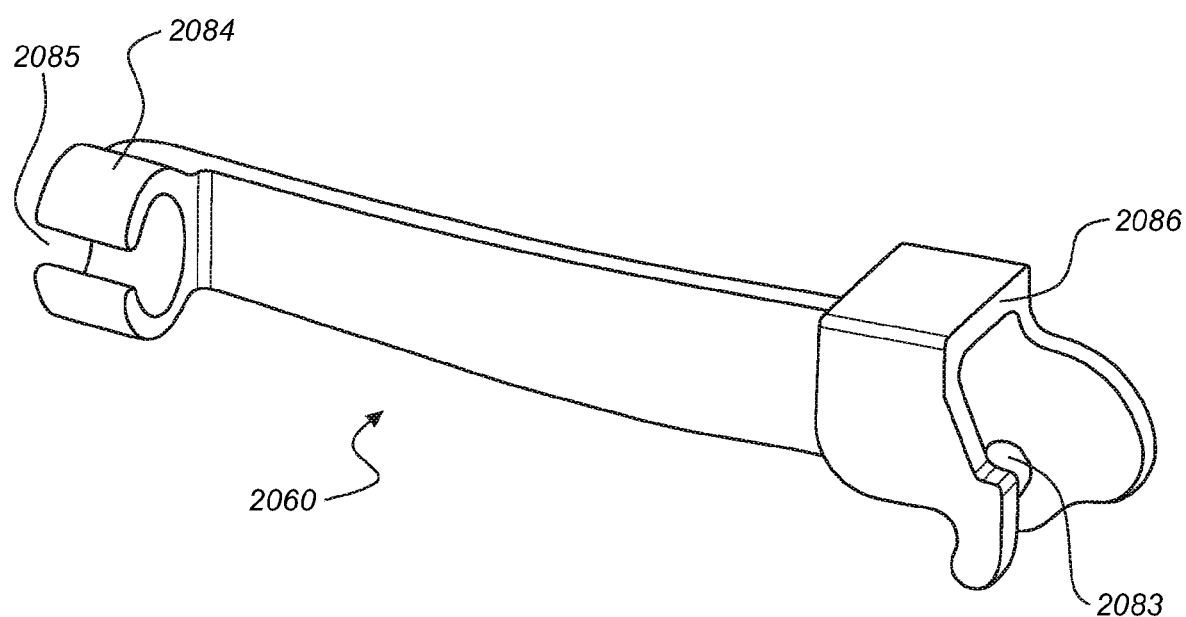
FIG. 71 is a perspective view of a disengagement arm of a tilt action disengagement mechanism.
Figure 72:
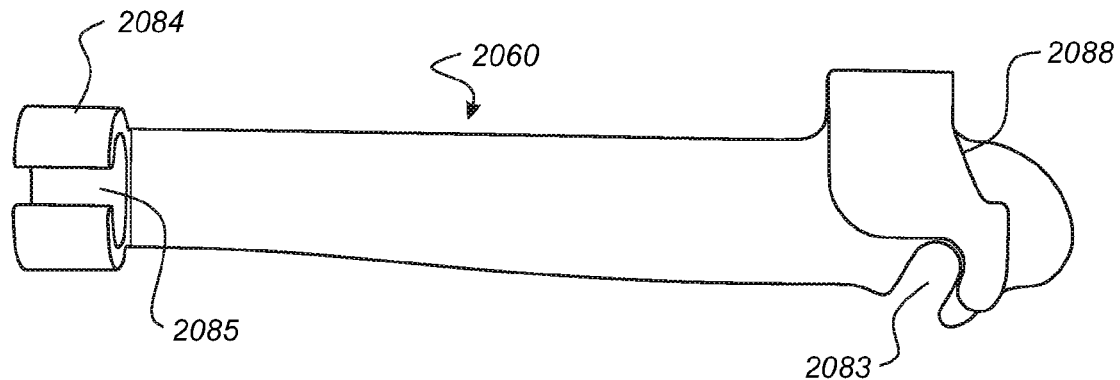
FIG. 72 is a side view of a disengagement arm of a tilt action disengagement mechanism.
Figure 73:
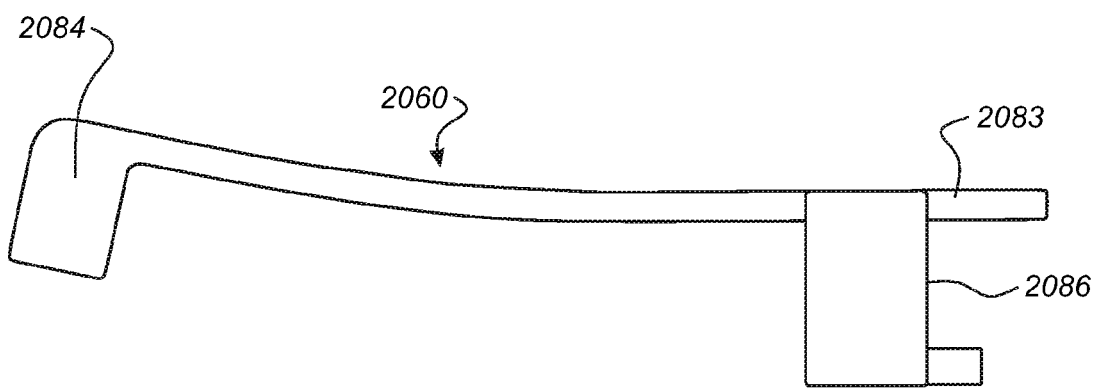
FIG. 73 is a top view of a disengagement arm of a tilt action disengagement mechanism.
Figure 74:
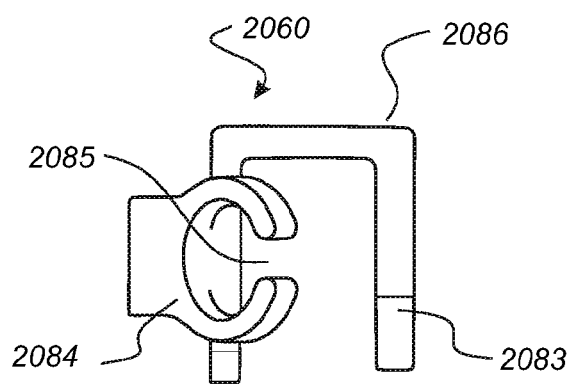
FIG. 74 is a rear view of a disengagement arm of a tilt action disengagement mechanism.
Figure 75:
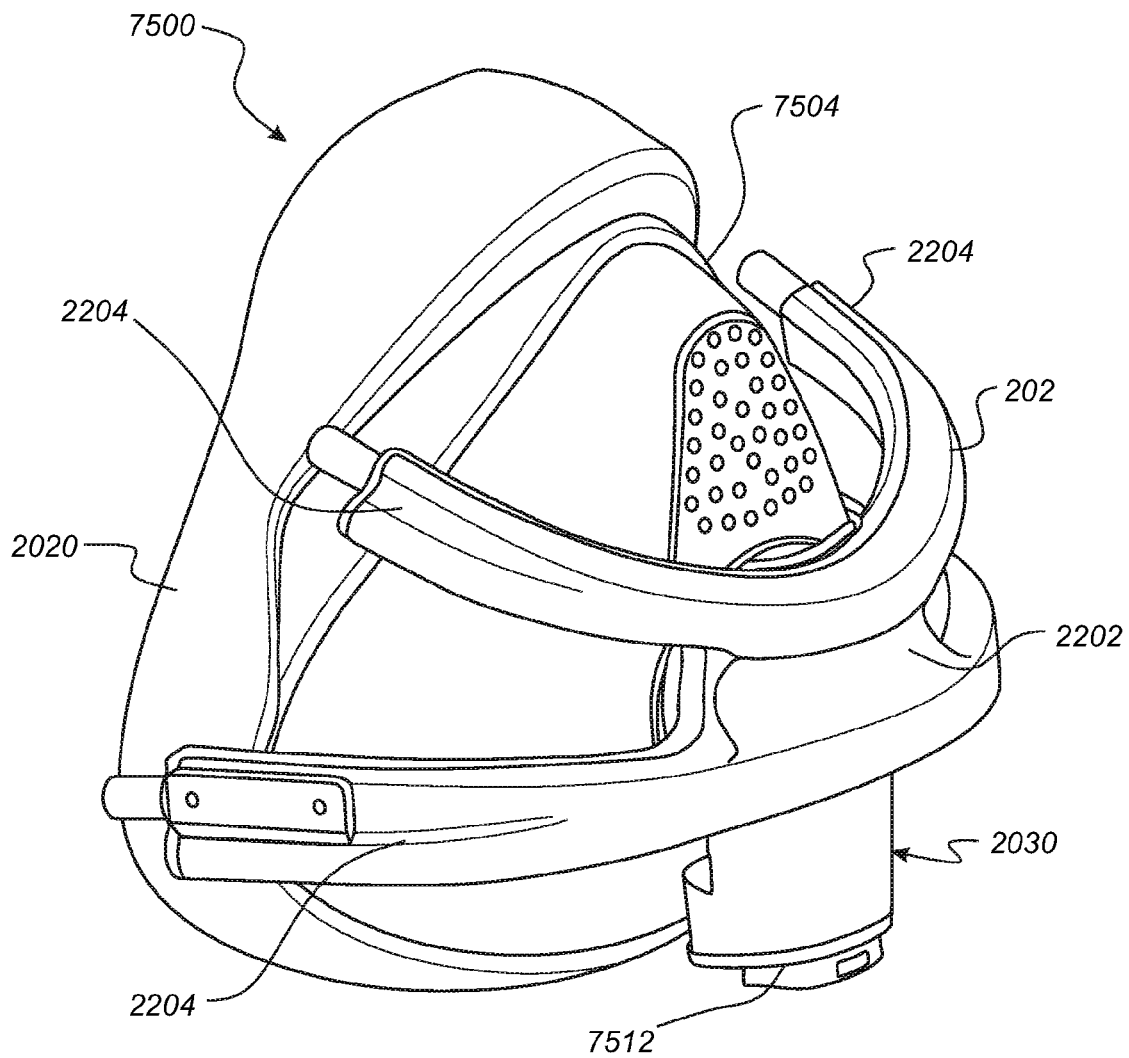
FIG. 75 is a perspective view of an embodiment of a mask assembly including a yoke portion of a headgear assembly, a cushion module, and a frame.

The disengagement arm 2060 is configured to directly or indirectly contact or otherwise engage the disengagement member 2053 to move the disengagement member 2053 from the unactuated position to the actuated position. In particular, when the disengagement arm 2060 is rotated about the pivot 2062 in a clockwise direction relative to the orientation shown in the figures, the disengagement arm 2060 contacts an engagement portion 2055a of the disengagement member 2053 and, if the disengagement arm 2060 is rotated a sufficient amount, moves the disengagement member 2053 to the actuated position. Accordingly, when disengagement arm 2060 is moved from a substantially level or horizontal position as illustrated in FIG. 66 and FIG. 69 to a substantially inclined or raised position as illustrated in FIG. 63, FIG. 67 and FIG. 70, disengagement member 2053 moves from the unactuated position to the actuated position. Conversely, when the disengagement arm 2060 is returned to the level or horizontal position, the disengagement member 2053 is able to return to the unactuated position or, when the force tending to rotate the disengagement arm 2060 in the clockwise direction is removed, the bias spring 2051 (or other biasing element) may move the disengagement member 2053 from the actuated to the unactuated position whereby the disengagement arm 2080 may be rotated back toward or to the substantially level position.

Although the disengagement arm 2060 could be configured for direct manual manipulation by the user, in the illustrated arrangement the disengagement arm 2060 is configured to engage a strap 208 of the headgear 200 and be actuated as a result of relative movement between the yoke 202, mask frame 2030 or cushion 2020 and the headgear strap 208. For example, to remove the mask assembly, the user can grasp the yoke 202, mask frame 2030 or cushion 2020 (referred to collectively as the "mask" for convenience) and rotate at least the bottom of the mask upwardly and/or outwardly away from the user's face (e.g., chin). The straps 208 of the headgear 200 tend to stay in place on the user's head due to frictional contact with the user and because of tension on the headgear straps 208. Accordingly, the movement of the mask initiated by the user causes clockwise movement of the disengagement arm 2060 relative to the mask, which actuates the disengagement member 2053, as described above. As a result, one or both of the disengageable locks 2048a, 2048b are disengaged and at least the lower straps 208 of the headgear 200 are permitted to elongate with lowered or little resistance. Similarly, clockwise movement of the disengagement arm 2060 relative to the mask is caused when the user places the rear portion 204 of the headgear on his or her head and rotates the bottom of the mask away from the face so that the mask can pass by the nose. Thus, one or both of the disengageable locks 2048a, 2048b are disengaged and at least the lower straps 208 of the headgear 200 are permitted to elongate with lowered or little resistance during donning of the mask assembly. Advantageously, the pivot 2062 may be located below the lower headgear attachment posts 2012a, 2012b to reduce tension in the lower strap 208 exerting a torque on the disengagement arm 2060. The range of rotation of disengagement arm 2060 may be limited by the range of linear travel of the disengagement member 2053 and/or a contact between disengagement arm and yoke 202. Alternatively, separate protrusions or any suitable mechanical stop may be implemented to limit the disengagement arm's rotation.

With reference to FIGS. 71-74, the disengagement arm 2060 may comprise a headgear engaging feature 2084, a pivot connection 2083, a stop 2086 and an engagement surface 2088. The headgear engaging feature 2084 is configured to couple the disengagement arm 1060 to a portion of the headgear 200, such as a strap 208 (e.g., lower strap) of the headgear 200 so that the disengagement arm 2060 moves relative to the yoke 202 or mask in response to relative movement between the headgear 200 and the yoke 202, mask frame 2030 or cushion module 2020, as described above. In the illustrated arrangement, the headgear engaging feature 2084 is a loop or collar configured to surround a substantial portion or entirety of a strap 208 of the headgear 200. The illustrated headgear engaging feature 2084 has a small open section 2085 to permit insertion of the strap 208 into the interior space of the loop or collar. The open section 2085 provides the engaging feature 2084 with a generally C-shaped cross-section. In other arrangements, the loop or collar may form a fully closed loop. Other suitable arrangements for coupling to the headgear 200 (or other portions of the mask that experience relative movement during donning or doffing) may also be used, such as a hook, rim or other connector (e.g. a snap-fit connector or other interlocking connector), into which a corresponding mating piece or connector from headgear 200 may be inserted, for example.

In some configurations, the headgear locating feature 2084 provides a removable connection between a headgear strap 208 and the disengagement arm 2060. In other configurations, the connection between headgear locating feature 2084 and the headgear 200 may be made permanent, for example by over-molding (e.g. with silicone rubber) the headgear locating feature 2084 and the headgear strap 208.

The pivot connection 2083 is configured to allow the disengagement arm 2060 to removably or permanently connect with the yoke 202 for rotation about the pivot axis define by the pivots 2062. In the illustrated arrangement, the pivot connection 2083 has an inner side portion and an outer side portion connected by a bridge portion. The inner side portion and the outer side portion have different shapes such that the overall pivot connection 2083 is asymmetrical. In the illustrated arrangement, the inner side portion is configured to provide a secure connection with the corresponding pivot 2062 of the yoke 202. Accordingly, the inner side portion surrounds a greater portion of a periphery of the pivot 2062 and has more material surrounding the recess that receives the pivot 2062 to inhibit or prevent deformation that would permit unintended separation of the pivot connection 2083 and the yoke 202.

The outer side portion is configured to pivot about the corresponding pivot 2062 of the yoke 202 and includes the engagement surface 2088, which is configured to selectively contact the engagement portion 2055a (FIGS. 69 and 70) and move the disengagement member 2053. Accordingly, in the illustrated arrangement, the outer side portion of the pivot connection 2083 surrounds less of the periphery of the corresponding pivot 2062 in comparison to the inner side portion. In addition, the outer side portion has less material surrounding the pivot 2062 in comparison to the outer side portion.

The engagement surface 2088 is located above the recess configured to receive the pivot 2062. In the illustrated arrangement, the engagement surface 2088 is substantially planar (linear from a side view) and is angled away from the disengagement member 2053 in a direction from a lower end to an upper end of the engagement surface 2088. However, other suitable shapes (e.g., single curve, multiple curves) can be employed for the engagement surface 2088 depending, for example, on the desired rate of movement of the disengagement member 2053 in response to movement of the disengagement arm 2060 relative to the yoke 202.

In the illustrated arrangement, the disengagement arm 2060 includes a stop surface or a stop 2086 that limits rotational movement of the disengagement arm 2060 relative to the yoke 202. The illustrated stop 2086 is defined by the bridge portion of the pivot connection 2083 and, in particular, by a leading edge of the bridge portion. Upon sufficient rotation of the disengagement arm 2060 in the clockwise direction relative to the yoke 202, the stop 2086 of the disengagement arm 2060 contacts the yoke 202 (e.g., an upper surface of the yoke 202) to limit movement of the disengagement arm 2060. Such an arrangement inhibits or prevents excessive force from being applied to the disengagement member 2053. However, in other arrangements, the disengagement member 2053 could be configured to define the stop point of rotation of the disengagement arm 2060 and, thus, could be configured to handle the expected loads.

Advantageously, disengagement arm 2060 may be shaped to correspond to a shape of the user's head along which the disengagement arm 2060 extends and/or a desired path of the corresponding strap 208 or other portion of the headgear 200. In the illustrated arrangement, a rearward portion (e.g., containing the headgear locating feature 2084) of the disengagement arm 2060 is slightly bent or curved inward relative to a forward portion (e.g., containing the pivot connection 2083) to follow the expected curvature of the user's face and/or desired path of the headgear strap 208.

FIGS. 75-84 illustrate a mask assembly 7500 suitable for use with any of the retention or lock arrangements and release arrangements described above. The mask assembly 7500 includes alternative arrangements for coupling the yoke 202 and the cushion module 2020 to the frame 2030 relative to the previously-disclosed assemblies. Accordingly, certain features of the retention or lock arrangements and the release arrangements are omitted for the sake of clarity. However, the mask assembly 7500 can incorporate or can be modified to incorporate any of the retention or lock arrangements and/or release arrangement disclosed herein. Alternatively, the previously-disclosed mask assemblies can incorporate or can be modified to incorporate any of the coupling arrangements disclosed with respect to the mask assembly 7500. Moreover, in many respects, the yoke 202, the cushion module 2020 and the frame 2030 are the same as or similar to one or more of the previously-described embodiments. Thus, features or components of the mask assembly 7500 that are not described in detail below can be the same as or similar to corresponding features or components described previously, or can be of another suitable arrangement.

In the illustrated arrangement, the yoke 202, the cushion module 2020 and the frame 2030 are distinct or separable components, which can be selectively assembled and disassembled. Allowing the yoke 202, the cushion module 2020 and the mask frame 2030 to be easily separated from one another and reassembled may provide various advantages, including easier cleaning of the mask by the user, replacement of components, and allowing the mask to be disassembled for easier transportation and storage, among others.

The illustrated mask assembly 7500 includes a first or yoke-to-frame connection arrangement that permits selective connection of the yoke 202 to the mask frame 2030. In particular, the illustrated mask frame 2030 comprises a ridge or lip 7909 that surrounds at least a portion of the perimeter of the frame 2030 and provides a feature or structure onto which the yoke 202 can removably attach or clip. In the illustrated arrangement, the lip 7909 is provided at least on each side of the frame 2030. However, in other arrangements, the lip 7909 could define a complete closed-loop perimeter. Alternatively, the lip 7909 could be provided in a number of discrete locations. That is, the lip 7909 can be provided only in those locations corresponding to engagement features of the yoke 202, which are described below. In the illustrated arrangement, the lip 7909 is formed by an extension of a front wall of the mask frame 2030 such that the forward surface of the lip 7909 is flush with adjacent portions of the front wall of the mask frame 2030. The lip 7909 may be unitarily-formed with the mask frame 2030 (e.g. formed as a protrusion from mask frame 2030) or may be a separate structure that is attached to the mask frame 2030 (e.g. mechanically coupled to or formed by an overmolded structure). Advantageously, the geometry of mask frame 2030 and/or lip 7909 may be asymmetrical, so as to inhibit or prevent rotation or pivoting of the yoke 202 and provide a single, stable orientation of yoke 202 relative to mask frame 2030.

Figure 76:
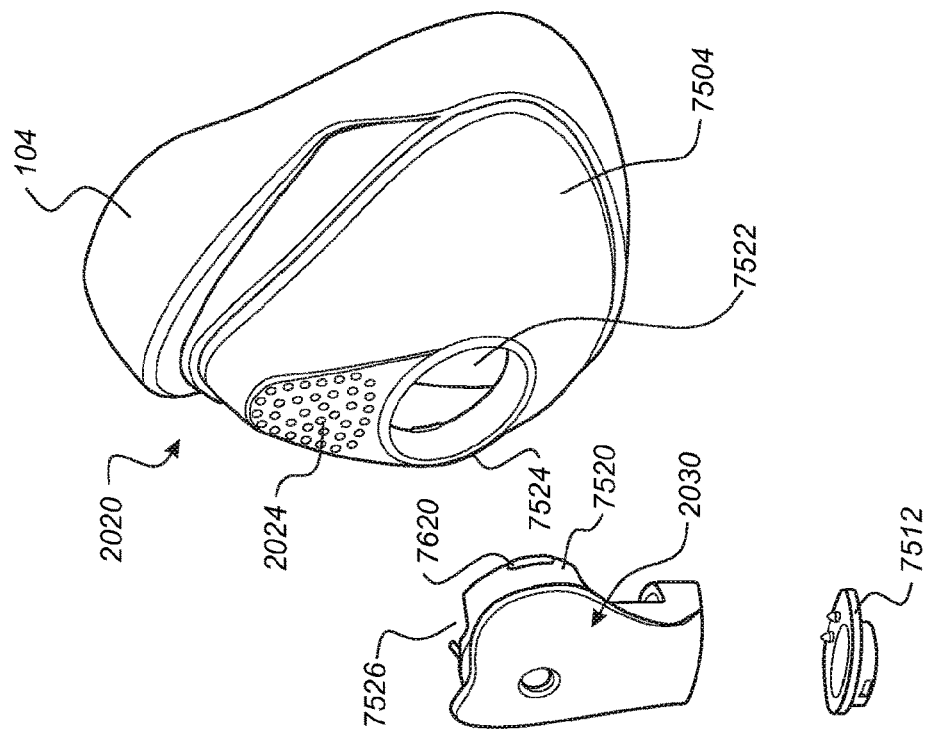
FIG. 76 is a perspective view of a front and left side of the mask assembly of FIG. 75 in an exploded state.
Figure 76:
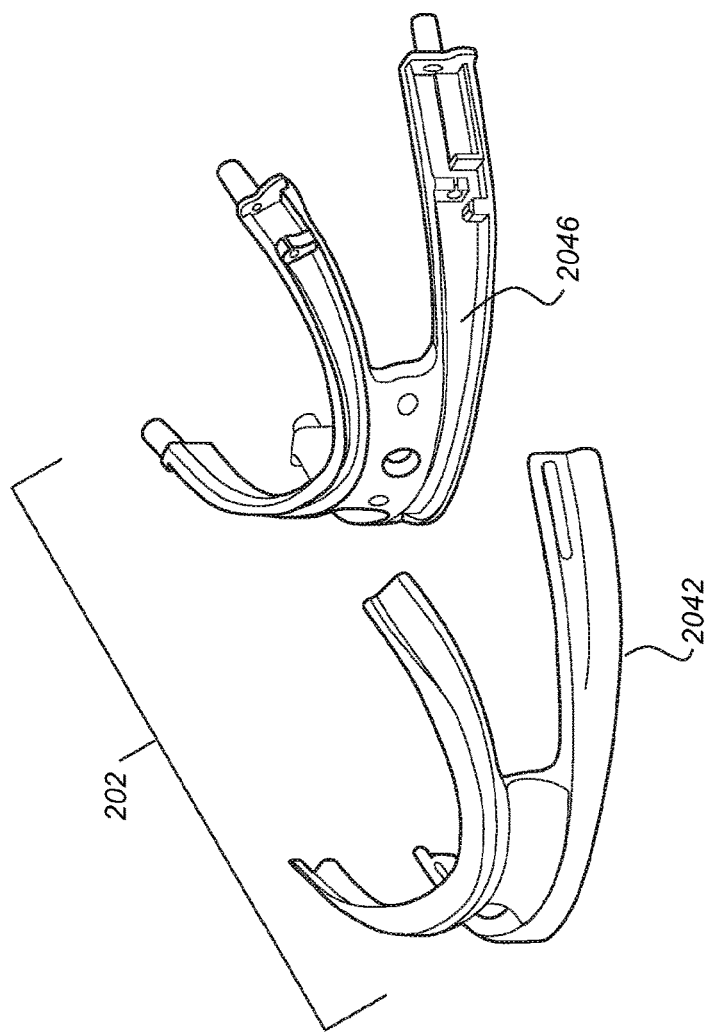
Figure 77:
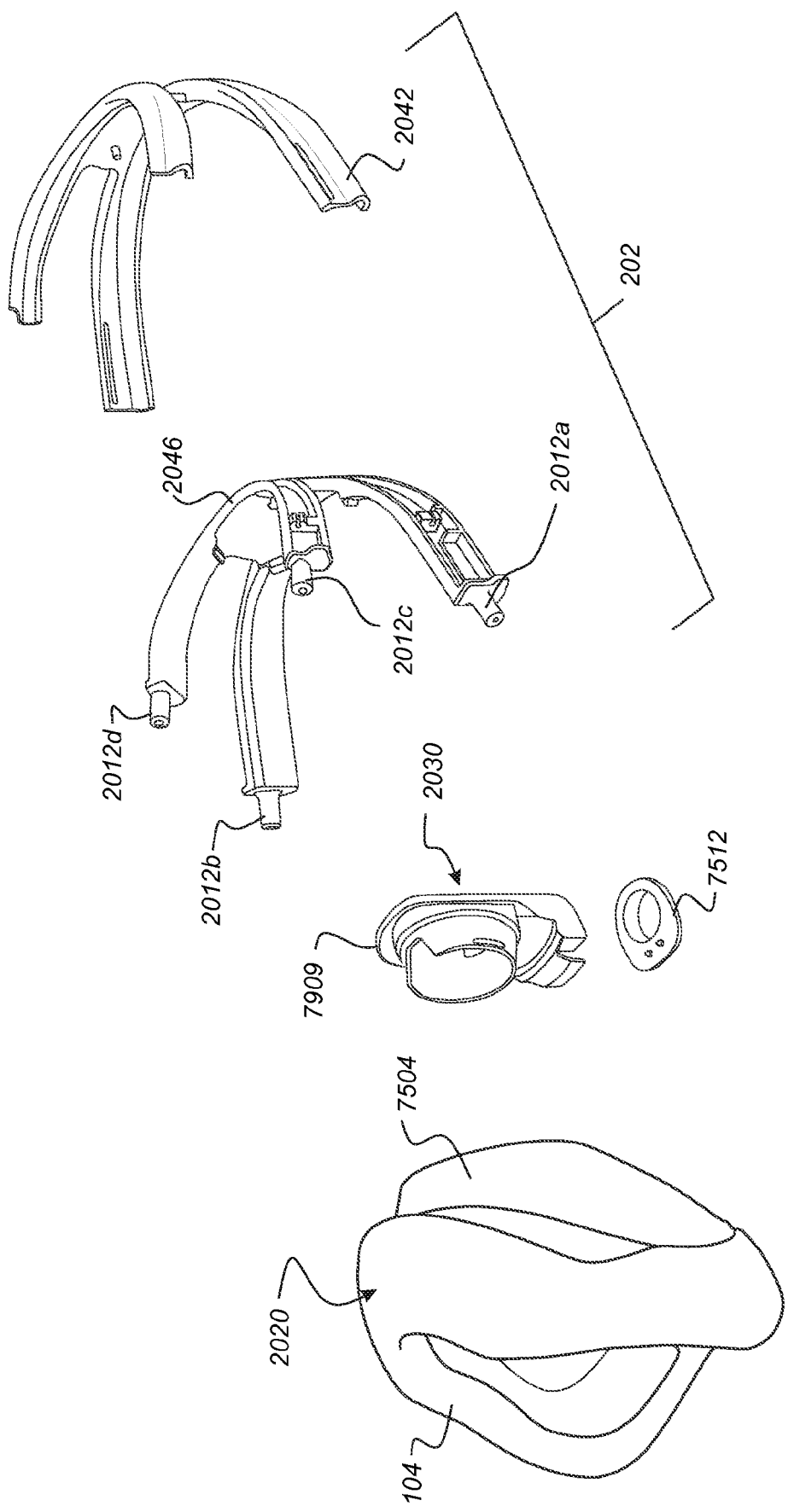
FIG. 77 is a perspective view of a rear and right side of the mask assembly of FIG. 75 in an exploded state.
Figure 78:
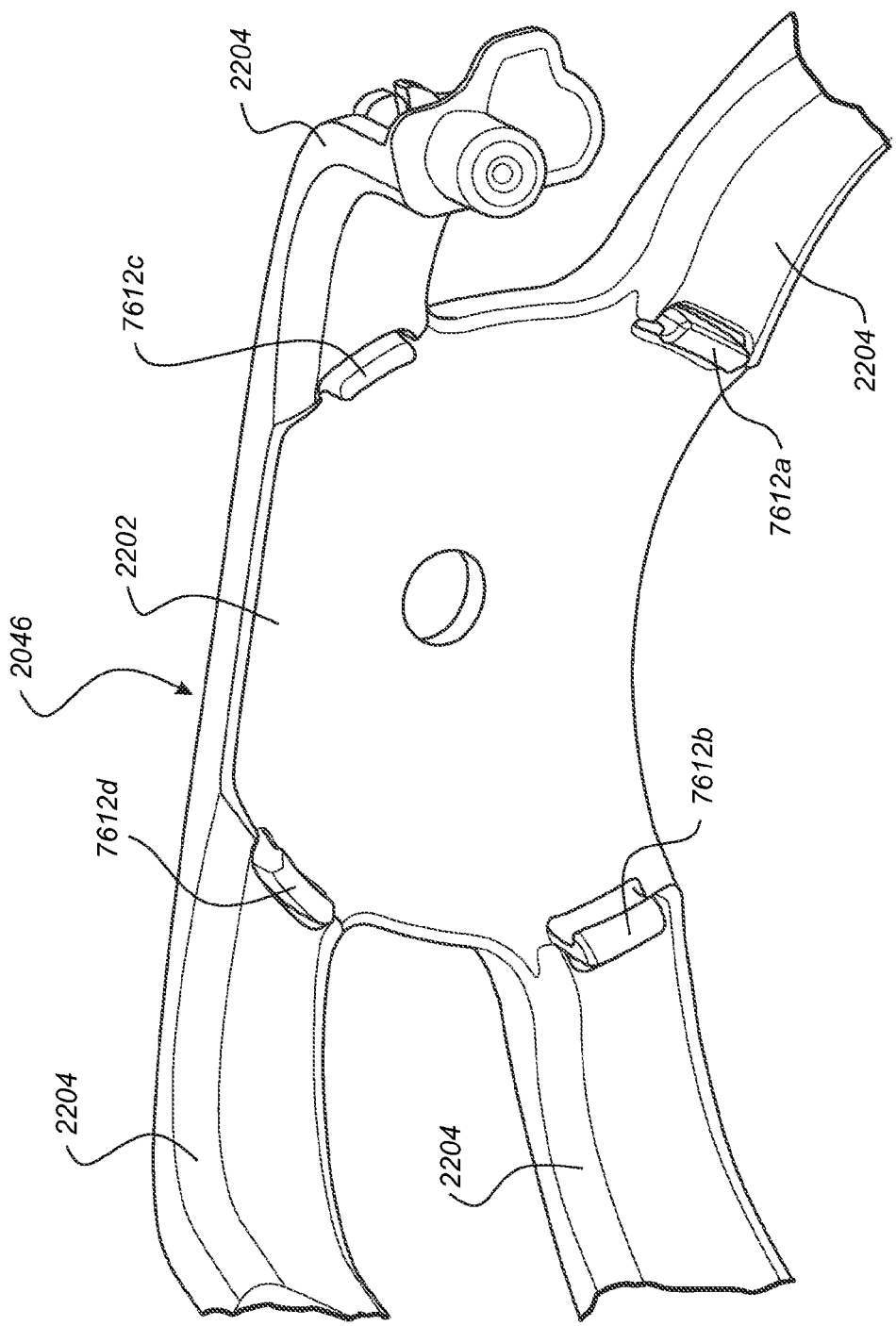
FIG. 78 is a rear view of the yoke illustrating a portion of a first connection arrangement for connecting the yoke to the frame.
Figure 79:
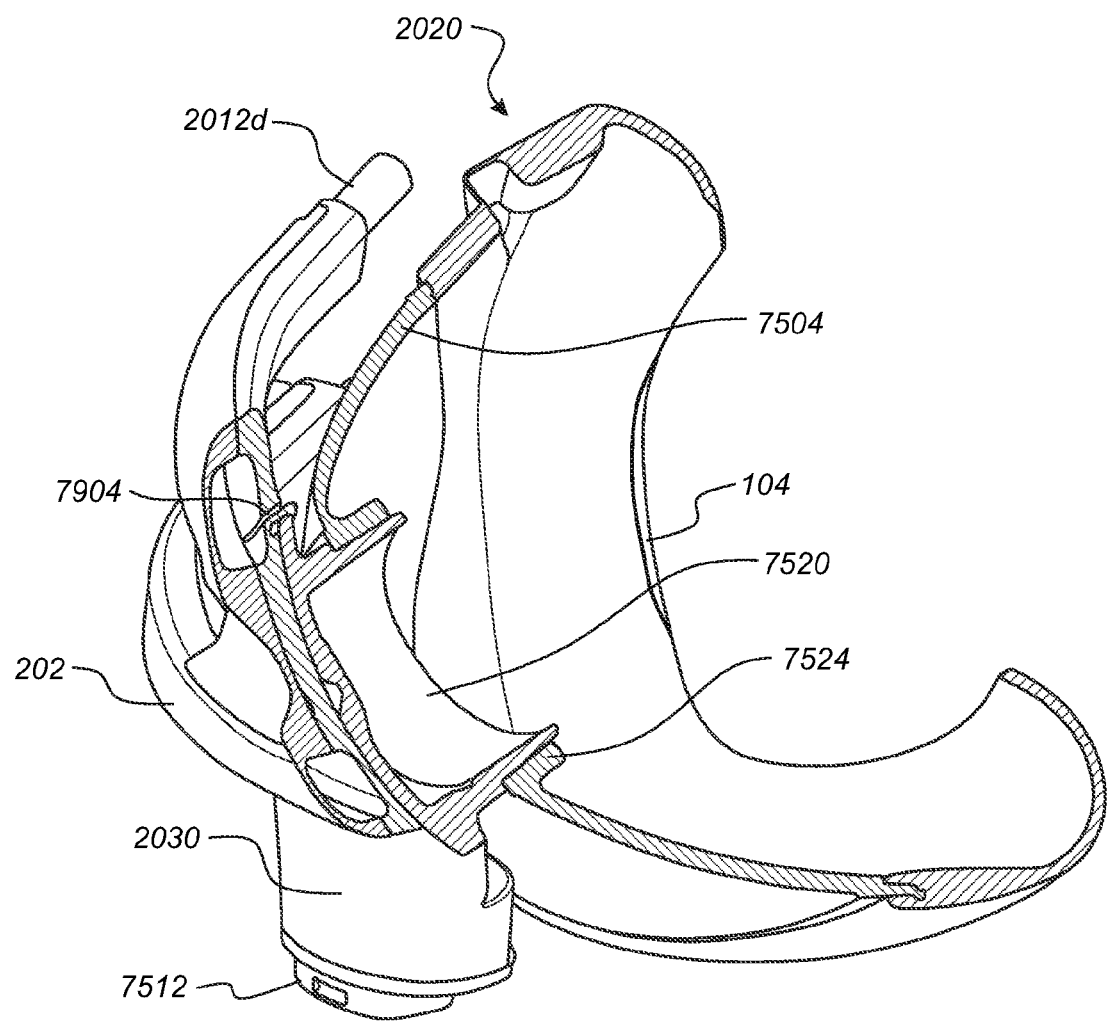
FIG. 79 is a sectional view of the mask assembly of FIG. 75 illustrating the first connection arrangement.
Figure 80:
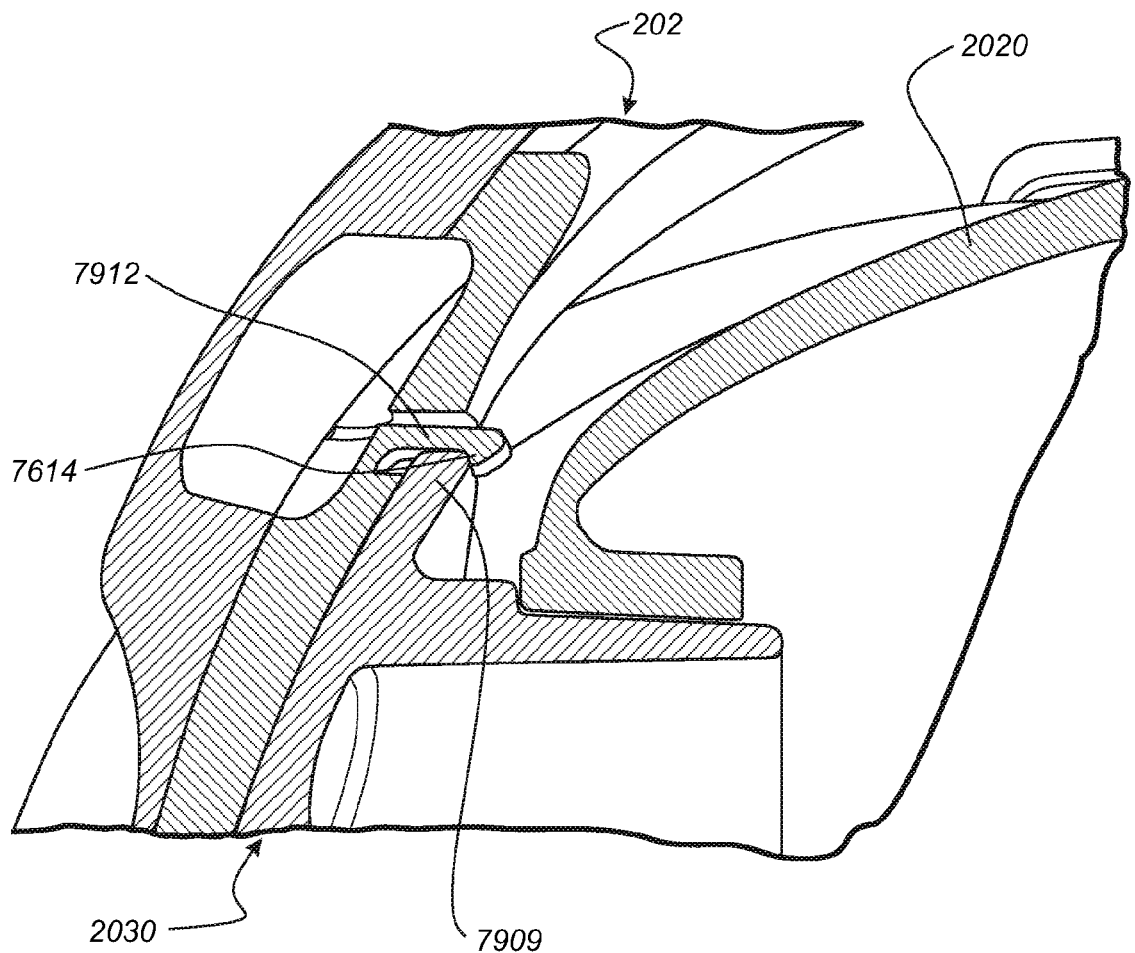
FIG. 80 is an enlarged view of a portion of the sectional view of FIG. 79 illustrating the first connection arrangement.
Figure 81:
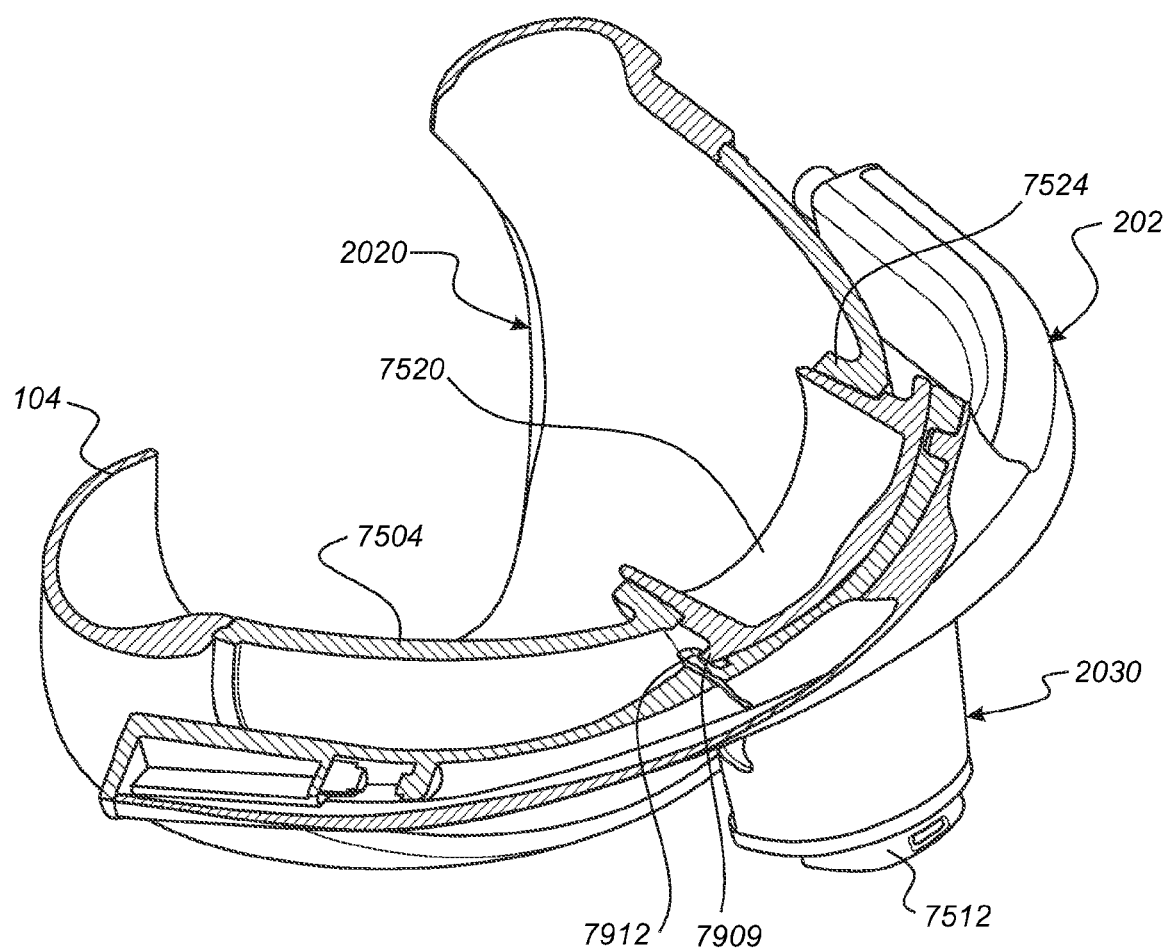
FIG. 81 is another sectional view of the mask assembly of FIG. 75 illustrating the first connection arrangement.
Figure 82A:
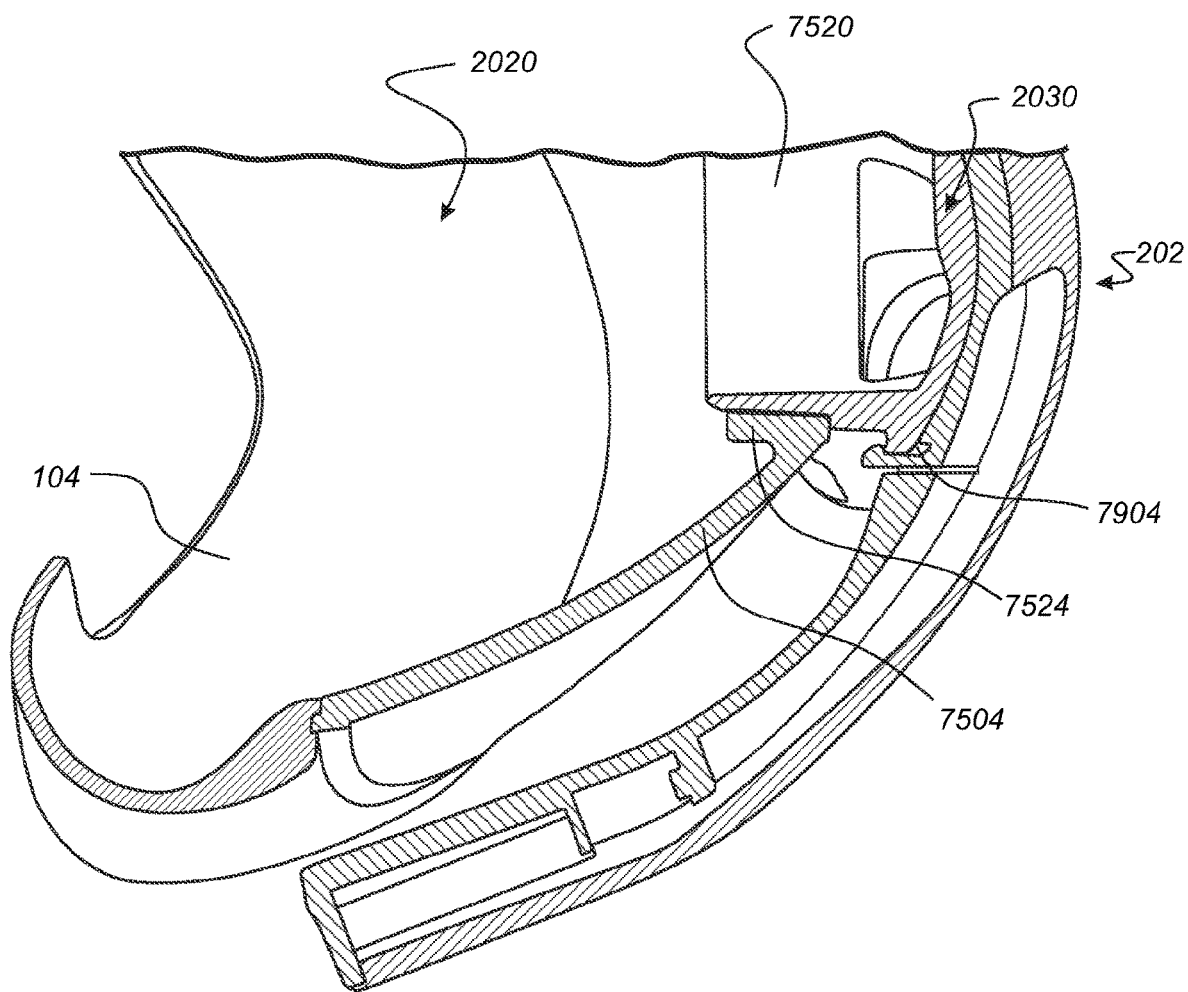
FIG. 82A is a sectional view of the mask assembly of FIG. 75 illustrating the first connection arrangement.
Figure 82B:
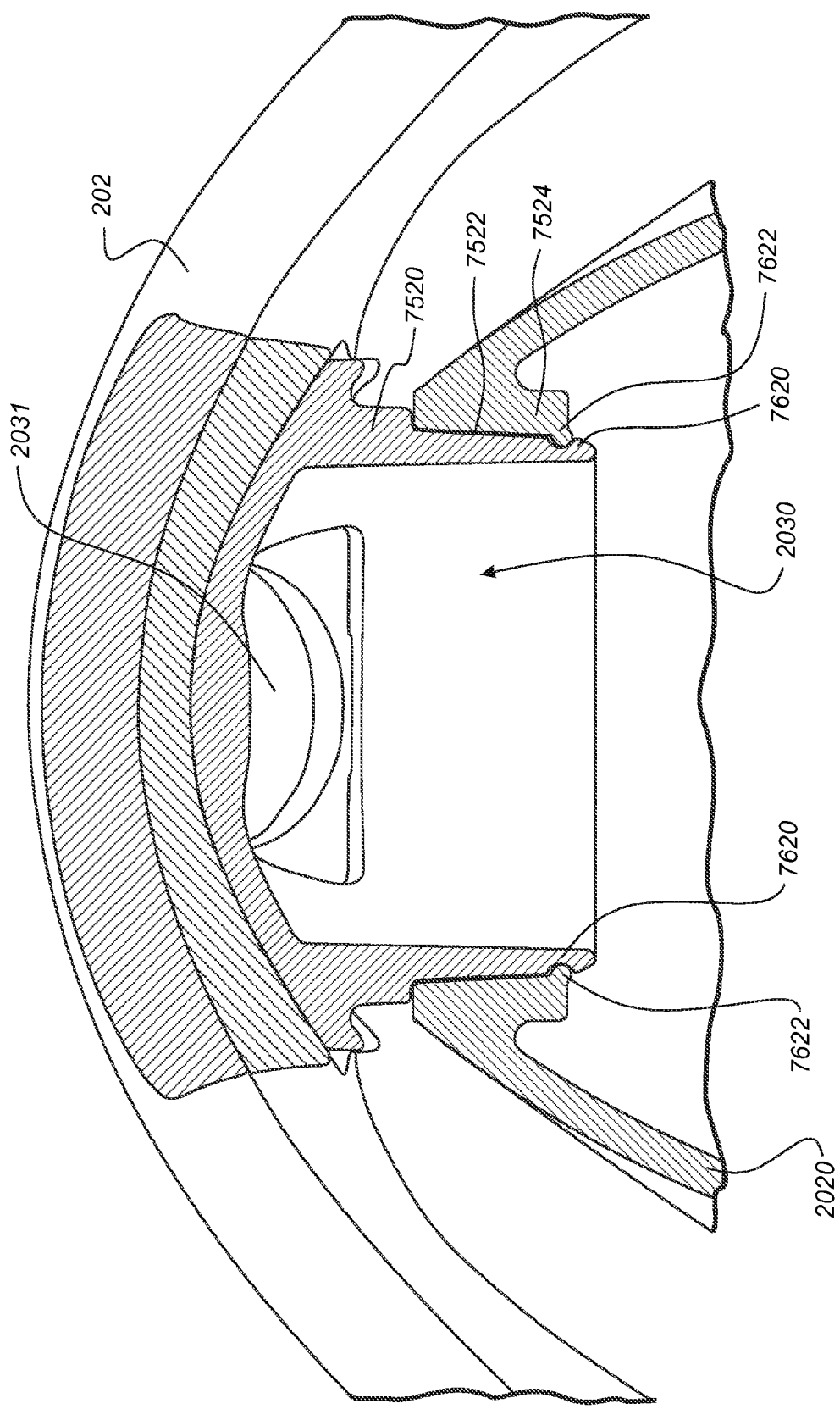
FIG. 82B is a sectional view of the mask assembly of FIG. 75 illustrating a second connection arrangement for connecting the cushion module to the frame.

With particular reference to FIGS. 76-78, as in prior embodiments, the illustrated yoke 202 comprises a first or front piece or portion 2042 and a second or rear piece or portion 2046. The front piece 2042 and the rear piece 2046 can be permanently or removably coupled to one another. The front piece 2042 and the rear piece 2046 cooperate to define one or more interior spaces configured to receive components of a retention or lock arrangement, such as directional locks (1800—FIGS. 25A-D, 2048—FIGS. 26-34, and 2058—FIGS. 51A, 51B). The yoke 202 includes a central portion 2202 and a plurality of arms (e.g., four arms 2204) that sweep rearwardly from the central portion. The arms 2204 are configured to connect to straps of the headgear. In some configurations, each arm 2204 can be connected to a single headgear strap such that the number of straps equals the number of arms 2204. However, in other arrangements, multiple straps can be connected to a single arm 2204 such that the number of straps is greater than the number of arms 2204 or a single strap can be connected to multiple arms 2204 (e.g., a strap can extend from a rear portion of the headgear to a first arm, from the first arm to a second arm and then return to the rear portion of the headgear) such that the number of straps is less than the number of arms 2204.

The illustrated frame 2030 defines an interior passage 2031 configured to communicate the flow of breathing gases from a gas conduit (not shown) to the cushion module 2020. The frame 2030 and/or the interior passage extend in a vertical direction and overlies a central portion of the cushion module 2020 when the mask assembly is viewed from the front. An upper edge of the frame 2030 terminates a relatively short distance above an inlet opening of the cushion module 2020 and can include a downwardly-curved or concave upper surface configured to accommodate a vent 2024 of the cushion module 2020. The mask frame 2030 may be configured for connection to a gas conduit (not shown). In the illustrated arrangement, a conduit connector portion 7512 is permanently or removably coupled to a lower end of the frame 2030 and is configured to be directly or indirectly coupled to a gas conduit. The conduit connector portion 7512 may also secure a valve member of an anti-asphyxiation valve (AAV) within the interior passage of the frame 2030.

FIG. 78 illustrates a rear piece 2046 of the yoke 202, which faces the frame 2030. The rear side of the yoke 202 includes a portion of the first or yoke-to-frame connection arrangement. In particular, the rear piece 2046 of the yoke 202 includes one or more connection features, generally referred to as 7612, which are configured to engage with a portion of the frame 2030, such as the lip 7909. The illustrated connection features 7612 are in the form of deflectable fingers or arms. In the illustrated arrangement, the yoke 202 includes four connection features 7612a, 7612b, 7612c, 7612d spaced around a periphery of a base portion or central portion 2202 of the yoke 202. The connection features 7612a, 7612b, 7612c, 7612d can be substantially similar or identical and, therefore, any description of a particular connection feature 7612a, 7612b, 7612c, 7612d or a connection feature 7612 generally, can be applied to each connection feature 7612a, 7612b, 7612c, 7612d unless otherwise indicated.

Each of the connection features 7612a, 7612b, 7612c, 7612d is associated with one of the arms 2204 of the yoke 202. In particular, each of the connection features 7612a, 7612b, 7612c, 7612d is located at or adjacent a base of the associated arm 2204 at or near a junction between the arm 2204 and the central portion 2202. Such an arrangement hides the connection features 7612a, 7612b, 7612c, 7612d when the yoke 202 is assembled to the frame 2030 and provides a clean and attractive appearance. In other arrangements, other numbers of connection features 7612 may be provided. For example, one, two, three, five, six or more connection features 7612 may be provided. The connection features 7612 can be arranged in a radial configuration about the periphery of the central portion 2202. The connection features 7612a, 7612b, 7612c, 7612d may be unitary with the rear piece 2046 of the made from a material that deforms elastically, such as e.g. polypropylene, high-density polyethylene, or polycarbonate.

The fingers or connection features 7612a, 7612b, 7612c, 7612d are hooked tabs extending in a rearward direction from the rear surface of the rear piece 2046 of the yoke 202. The fingers or tabs 7612a, 7612b, 7612c, 7612d have a first end connected to (e.g., unitarily formed with) the rear piece 2046 of the yoke 202 and a second end that defines an inwardly-extending return, catch or projection 7614 configured to engage the lip 7909 of the frame 2030. In particular, each projection 7614 defines a first interlock surface configured to contact a rearward surface of the lip 7909, which functions as a second interlock surface, such that each projection 7614 and the lip 7909 define a snap-fit or an interlock connection. The rearward-facing surface of projections 7614, or the leading surface relative to the assembly direction, can be chamfered, angled or sloped so that the fingers or connection features 7612a, 7612b, 7612c, 7612d are deflected outwardly by contact with and movement toward the lip 7909 of the frame 2030. Once the projections 7614 move past the lip 7909, the fingers or connection features 7612a, 7612b, 7612c, 7612d can elastically recover and move radially inward until the projections 7614 engage the lip 7909. In alternate arrangements, the illustrated arrangement can be reversed such that the fingers or connection features 7612a, 7612b, 7612c, 7612d are located on the frame 2030 and the lip 7909 is located on the yoke 202. Moreover, other types of structures providing cooperating interlocking surfaces can be used.

Figure 83:
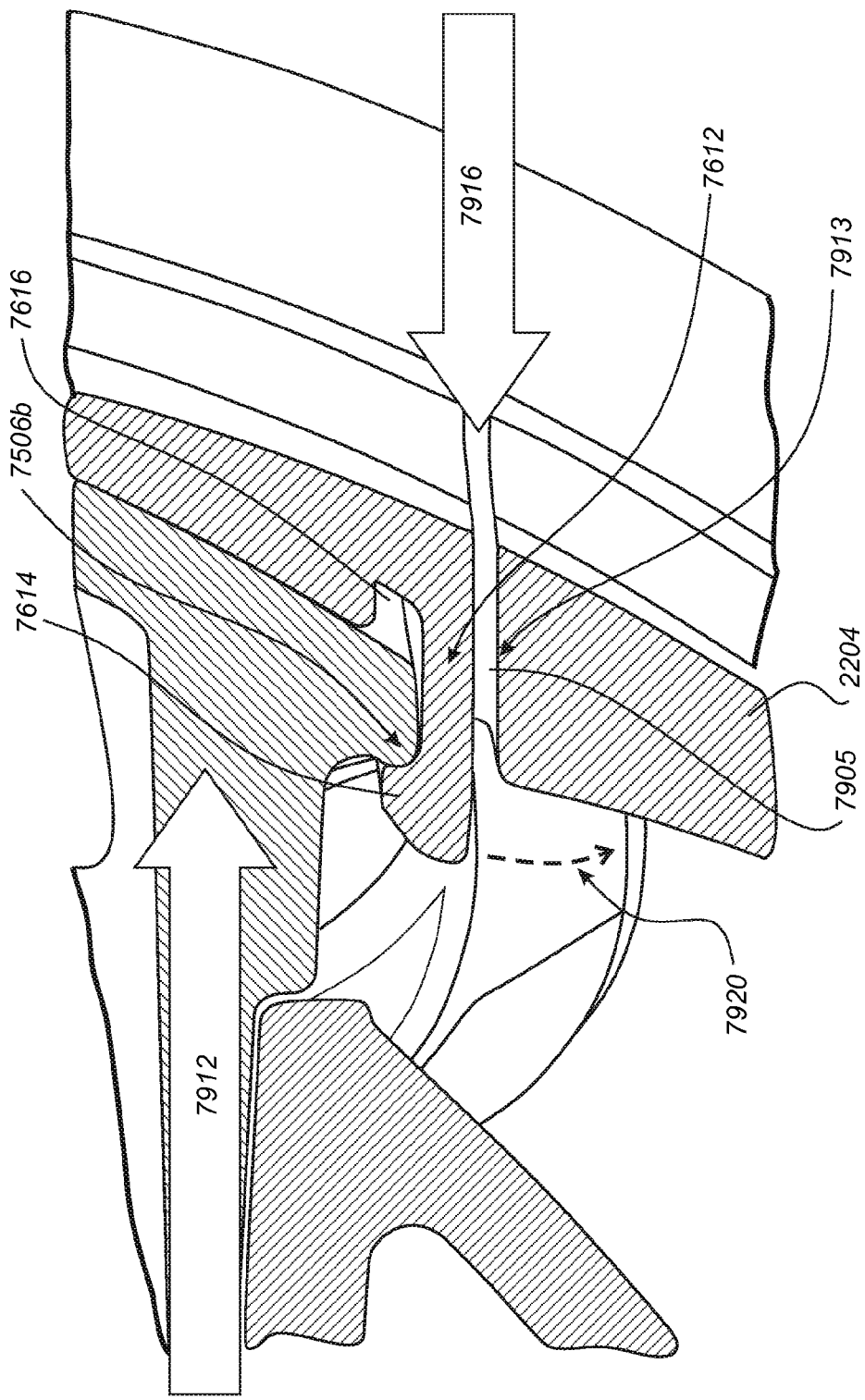
FIG. 83 is an enlarged view of a portion of the sectional view of FIG. 82A illustrating the first connection arrangement and directions of movement to connect the yoke to the frame.

FIG. 83 illustrates the general direction of forces applied to the yoke 202 and the frame 2030 during the connection or assembly process. For example, a first force may be applied on the yoke 202 substantially in the direction of arrow 7916. The first force may be applied through a user's hand pushing or pulling the yoke towards the frame 2030. A second force or counterforce is applied substantially in the opposite direction of the first force, as illustrated by arrow 7912. The connection feature 7612 and lip 7909 are compressed against each other and one or both may lightly deform or deflect (e.g. elastic deformation) to permit the connection feature 7612 to move past the lip 7909. The path of motion of the deflection of connection feature 7612 is substantially radially outward, as illustrated by arrow 7920. The deformation or deflection may be limited by a stop surface 7913, which in the illustrated arrangement is defined by the corresponding arm 2204 of the yoke 202. Advantageously, such an arrangement may limit the deflection of connection feature 7612 to within a range of elastic deformation to reduce the risk of breakage and increase the useful life of the yoke 202 in comparison to arrangements that do not limit deflection of the connection features 7612. The stop surface 7913 may be separated from the connection feature 7612 by a gap 7905, which can extend partially or completely through the rearward wall of the rear piece 2046 of the yoke 202. The gap 7905 can facilitate deflection of the connection feature 7612 and/or decouple movement between the connection feature 7612 and the associated arm 2204 such that movement of the arm 2204 does not move the connection feature 7612 or at least does not result in sufficient movement to cause unintended disconnection of the connection feature 7612 from the lip 7909. After connection feature 7612 has passed lip 7909, the resilient nature of the connection feature 7612 will allow it to elastically recover toward or to its relaxed position such that the projection 7614 engages the lip 7909 to secure the yoke 202 to the frame 2030.

With particular reference to FIGS. 78 and 83, the rear piece 2046 of the yoke 202 can include a recess 7616 associated with each of the fingers or connection features 7612. Each recess 7616 is located adjacent the first end of the associated finger or connection feature 7612 to facilitate deflection of the finger or connection feature 7612. Preferably, the recess 7616 is immediately adjacent the finger or connection feature 7612. However, in other arrangements, the recess 7616 is located close enough to the finger or connection feature 7612 such that the deflection force required is lower than a design that does not include a recess 7616. In an alternative arrangement, a single recess could be associated with, or located adjacent, more than one or all of the fingers or connection features 7612. For example, a single recess could extend along one side of the central portion 2202 and adjacent each of the fingers or connection features 7612 on that side. Or, a single recess could circumscribe the central portion 2202 and be located adjacent all of the fingers or connection features 7612.

The illustrated mask assembly 7500 includes a second or cushion module-to-frame connection arrangement that permits selective connection of the cushion module 2020 to the mask frame 2030. The mask frame 2030 includes a rearwardly-extending cylindrical collar 7520 configured to engage a corresponding opening 7522 defined by a cylindrical wall 7524 of the housing 7504 of the cushion module 2020. The cylindrical wall 7524 can extend inwardly from an outer wall of the housing 7504 toward or into a breathing chamber of the cushion module 2020. In the illustrated arrangement, the collar 7520 and the opening 7522 define a circular or substantially circular perimeter. However, in other arrangements, the collar 7520 and/or the opening 7522 could have non-circular shapes, such as ovate or polygonal, for example. Accordingly, as used herein, the term "cylindrical" can include an extruded closed loop of any perimeter shape, unless indicated otherwise.

The illustrated mask frame 2030 includes one or more recesses 7620 configured to receive a corresponding protrusion 7622 of the cushion module 2020. However, this arrangement could also be reversed such that the mask frame 2030 includes one or more protrusions and the cushion module 2020 includes corresponding recesses. The illustrated mask frame 2030 includes a pair of part-annular recesses 7620, which extend in a circumferential direction and are located on opposing sides of the collar 7520. The cushion module 2020 includes a corresponding pair of protrusions 7622 that engage the recesses 7620 in a snap-fit or interlocking manner. In other arrangements, the mask frame 2030 and the cushion module 2020 can include a lesser number (e.g., a single) or a greater number of recesses 7620 and protrusions 7622. The interlocking connection of the recesses 7620 and the protrusions 7622 provide a retention force tending to inhibit or prevent unintentional separation of the cushion module 2020 from the mask frame 2030. In addition, the recesses 7620 and the protrusions 7622 can provide feedback (e.g., tactile or audible feedback) to the user that connection between the cushion module 2020 and the mask frame 2030 is complete and/or can inhibit or prevent relative rotation between the cushion module 2020 and the mask frame 2030.

Figure 84:
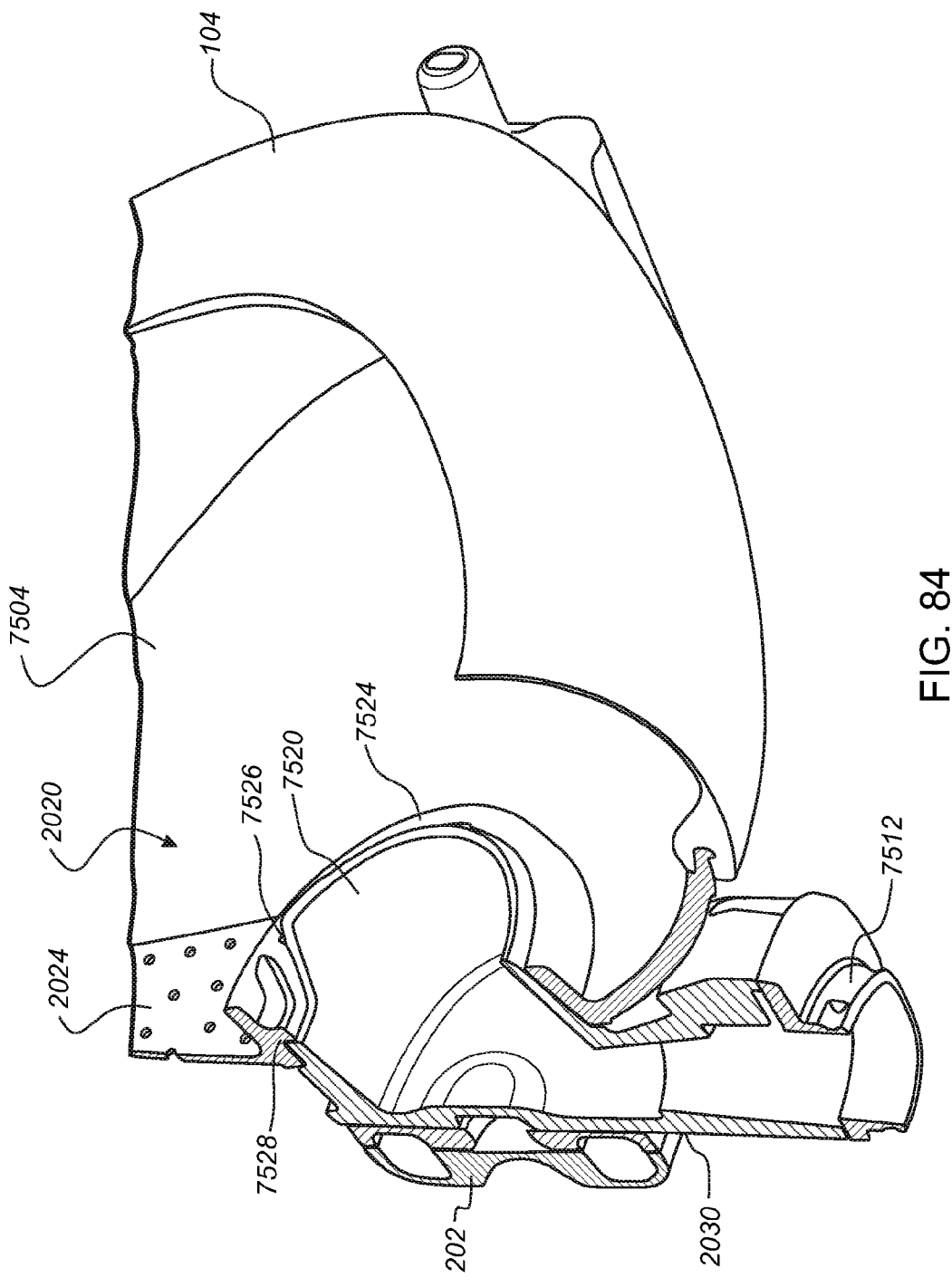
FIG. 84 is a sectional view of the mask assembly of FIG. 75 illustrating an alignment feature that aligns the cushion module with the frame.

In some configurations, the mask assembly 7500 includes an alignment feature that facilitates proper rotational alignment between the cushion module 2020 and the mask frame 2030. In some configurations, the alignment feature can also inhibit or prevent relative rotation between the cushion module 2020 and the mask frame 2030. With reference to FIG. 84, the collar 7520 of the illustrated mask frame 2030 includes a recess 7526 configured to receive a corresponding protrusion 7528 of the cushion module 2020. However, this arrangement could be reversed such that the protrusion is located on the mask frame 2030 and the recess is located on the cushion module 2020.

In the illustrated arrangement, the side surfaces of the protrusion 7528 contact corresponding side surfaces of the recess 7526 to limit rotation of the cushion module 2020 relative to the mask frame 2030. An outer shape defined by at least the side surfaces of the protrusion 7528 substantially corresponds to the size and the shape defined by at least the side surfaces of the recess 7526 such that any significant relative rotational movement is prevented. However, in other arrangements, a gap may be provided between the protrusion 7528 and the recess 7526 such that some amount of rotation may be permitted. In the illustrated arrangement, the recess 7526 and the protrusion 7528 each have a generally trapezoidal shape in the circumferential direction or otherwise have shapes that taper in width in a direction from the rear to the front so that the recess 7526 acts as a lead-in for the protrusion 7528 to ease assembly.

In some configurations, a forward-facing surface of the protrusion 7528 contacts the rearward-facing surface of the recess 7526 when the cushion module 2020 is properly assembled to the mask frame 2030. With such an arrangement, contact between the forward-facing surface of the protrusion 7528 and the rearward-facing surface of the recess 7526 can provide an indication or feedback (e.g., tactile or audible feedback) to the user that the connection is complete. In addition or in the alternative, other portions of the cushion module 2020 and the mask frame 2030 can contact upon complete assembly, such as a forward-facing perimeter surface of the cylindrical wall 7524, for example.

The features of each mask assembly or portions thereof disclosed herein can be utilized with the other mask assemblies or portions thereof disclosed herein. For example, the directional locks, including manually or deliberately disengageable locks and others, can be utilized in any straps (e.g., upper or lower straps, single side straps or double side straps) or any other portions of a headgear arrangement or other portions of an overall mask assembly to allow for adjustment in a length of a headgear portion or an overall closed loop ("circumferential") dimension of the mask assembly. Any of the disclosed release or disengagement mechanisms can be employed with any of the directional locks, or other controllable lock types, at any disclosed location or other suitable locations within the headgear or mask assembly. Furthermore, in some configurations, each directional lock (or other lock or adjustment mechanism) can include 2-6 lock elements, or lock washers, and/or can be capable of exerting a locking force of about 2-8 Newtons. In other configurations, each directional lock (or other lock or adjustment mechanism) can include 3-5 lock elements, or lock washers, and/or can be capable of exerting a locking force of about 4-6 Newtons.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A headgear for a respiratory mask, comprising:
   at least one strap comprising a filament;

a directional lock having an engaged configuration and a disengaged configuration with respect to the filament;

a disengaging member operable to prevent the directional lock from moving to the engaged configuration in response to elongation of the at least one strap; and an actuator configured to act on the disengaging member to cause the disengaging member to hold the directional lock in the disengaged configuration, wherein the actuator is configured to automatically act on the disengaging member when user pulls mask away from a user's face.

2. The headgear of claim 1, wherein the actuator is selectively operable to act on the disengaging member.

3. The headgear of claim 2, wherein the actuator comprises a movable bar, a button, or a handle.

4. The headgear of claim 1, wherein the actuator comprises an arm coupled to the at least one strap and configured to be movable relative to the respiratory mask.

5. The headgear of claim 1, wherein the disengaging member is normally biased away from holding the directional lock in its disengaged configuration.

6. The headgear of claim 1, wherein the at least one strap comprises a first strap portion and a second strap portion, wherein the filament is attached to one of the first strap portion and the second strap portion and the first strap portion and the second strap portion are movable relative to one another to vary a length of the at least one strap.

7. The headgear of claim 1, wherein the at least one strap extends between a head engaging portion and a mask engaging portion of the headgear.

8. A mask assembly comprising the headgear of claim 1, wherein the mask assembly comprises:

a mask, comprising:
a frame; and
a cushion module comprising a housing and a seal;
wherein the mask comprises a connection arrangement configured to connect the cushion module to the frame, the connection arrangement comprising at least one protrusion located on one of the cushion module and the frame and at least one recess located on the other of the cushion module and the frame, the at least one protrusion configured to engage the at least one recess to secure the cushion module to the frame.

9. The mask assembly of claim 8, wherein the cushion module comprises a cylindrical wall defining an opening that receives a collar of the frame.

10. The mask assembly of claim 9, wherein the at least one protrusion extends in a circumferential direction on the cylindrical wall and the at least one recess extends in a circumferential direction on the collar.

11. The mask assembly of claim 9, wherein the cylindrical wall extends into a breathing chamber of the cushion module from an outer wall of the housing.

12. The mask assembly of claim 9, further comprising an alignment feature comprising a recess defined by one of the cushion module and the frame and a protrusion defined by the other of the cushion module and the frame, wherein the protrusion is configured to engage the recess to facilitate rotational alignment of the cushion module relative to the frame.

13. The mask assembly of claim 8, wherein the headgear comprises a yoke configured to connect the headgear to the mask.

14. The mask assembly of claim 13, wherein the yoke comprises a central portion and at least one arm extending from the central portion, wherein the at least one arm is configured to connect to the at least one strap of the headgear.

15. The mask assembly of claim 14, wherein the frame comprises a lip and the yoke comprises at least one hooked connection finger configured to selectively engage the lip to secure the yoke to the frame.

16. The mask assembly of claim 15, wherein the lip extends along a perimeter of the frame.

17. The mask assembly of claim 15, wherein the lip extends from a front surface of the frame.

18. The mask assembly of claim 15, wherein the at least one hooked connection finger is located adjacent a junction between the at least one arm and the central portion.

19. The mask assembly of claim 15, further comprising a recess located adjacent to and configured to facilitate deflection of the at least one hooked connection finger.

20. The mask assembly of claim 18, further comprising a gap located adjacent to and configured to facilitate deflection of the at least one hooked connection finger and/or to decouple movement of the at least one arm and the at least one hooked connection finger.

21. The mask assembly of claim 20, wherein the gap extends entirely through a rear wall of the yoke.

22. The mask assembly of claim 14, wherein the at least one strap comprises a plurality of straps and the at least one arm comprises a plurality of arms.

23. The mask assembly of claim 22, wherein a number of straps of the headgear is different than a number of arms of the headgear.

* * * * *